United States Patent [19]

Howard et al.

[11] Patent Number: 5,597,826
[45] Date of Patent: Jan. 28, 1997

[54] COMPOSITIONS CONTAINING SERTRALINE AND A 5-HT$_{1D}$ RECEPTOR AGONIST OR ANTAGONIST

[75] Inventors: Harry R. Howard; John E. Macor; Bertrand L. Chenard; Jeffrey S. Sprouse; David W. Schulz, all of New York, N.Y.

[73] Assignee: Pfizer Inc., New York, N.Y.

[21] Appl. No.: 306,230

[22] Filed: Sep. 14, 1994

[51] Int. Cl.$^6$ .................... A01N 43/60; A61K 31/495
[52] U.S. Cl. .................... 514/255; 514/247; 514/256; 514/303; 514/319; 514/357; 514/428; 514/429; 514/647; 514/657; 514/811
[58] Field of Search .................... 514/255, 357, 514/247, 428, 429, 303, 256, 319, 647, 657, 811

[56] References Cited

U.S. PATENT DOCUMENTS

| | | | |
|---|---|---|---|
| 4,940,731 | 7/1990 | Bick | 514/657 |
| 4,962,128 | 10/1990 | Doogan et al. | 514/647 |
| 5,130,338 | 7/1992 | Bacopoulos | 514/640 |

OTHER PUBLICATIONS

CA (116): 128,683.
CA (118): 169,115.
CA (111): 77800.
Luciana Giardino, "Modulation of GABAergic System by the SSRI Sertraline", Neuropsychopharmacology, vol. 10, No. 3S/P, p. 6S, May 1994.
Pierre Blier and Claude de Montigney, "Current Advances and Trends in the Treatment of Depression", Trends in Pharmacological Sciences, vol. 15, No. 7, p. , (Jul. 1994).
Patrick Martin and Alain J. Puech, "Is there a relationship between 5-HT$_{1B}$ receptors and the mechanisms of action of antidepressant drugs in the learned helplessness paradigm in rats?", European Journal of Pharmacology, 192 (1991) 193–196.

B. Kenneth Koe, et al., "Sertraline, a selective inhibitor of serotonin uptake, induces subsensitivity of β-adrenoceptor system of rat brain", European Journal of Pharmacology, 141 (1987) 187–194.

Mike Briley and Chantal Moret, "Neurobiological Mechanisms Involved in Antidepressant Therapies", Clinical Neuropharmacology, vol. 16, No. 5, pp. 387–400 (1993).

Primary Examiner—Samuel A. Acquah
Attorney, Agent, or Firm—Peter C. Richardson; Paul H. Ginsburg; Garth Butterfield

[57] ABSTRACT

The present invention relates to novel compositions containing the serotonin selective re-uptake inhibitor (SSRI), preferably (1S-cis)-4-(3,4-dichlorophenyl)-1,2,3,4-tetrahydro-N-methyl-1-naphthalenamine, and an agonist or antagonist of the serotonin 1 (5-HT$_1$) receptor and to the use of such compositions for treating or preventing a condition selected from mood disorders, including depression, seasonal affective disorders and dysthmia, anxiety disorders including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa; obesity; cluster headache; migraine; pain; Alzheimer's disease; chronic paroxysmal hemicrania; headache associated with vascular disorders; Parkinson's disease, including dementia in Parkinson's disease, neuroleptic-induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies.

13 Claims, No Drawings

COMPOSITIONS CONTAINING SERTRALINE AND A 5-HT$_{1D}$ RECEPTOR AGONIST OR ANTAGONIST

BACKGROUND OF THE INVENTION

The present invention relates to novel compositions containing the serotonin selective re-uptake inhibitor (SSRI) (1S-cis)-4-(3,4- dichlorophenyl)-1,2,3,4-tetrahydro-N-methyl-1-naphthalenemine (hereinafter sertraline) and an agonist or antagonist of the serotonin 1 (5-HT$_1$) receptor and to the use of such compositions for treating or preventing a condition selected from mood disorders, including depression, seasonal effective disorders and dysthmia, anxiety disorders including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa; obesity; cluster headache; migraine; pain; Alzheimer's disease; chronic paroxysmal hemicrania; headache associated with vascular disorders; Parkinson's disease, including dementia in Parkinson's disease, neuroleptic-induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies.

U.S. Pat. No. 4,536,518 issued Aug. 20, 1985 refers to sertraline and derivatives thereof and states that these compounds are useful as antidepressant agents.

U.S. Pat. No. 4,940,731 issued Jul. 10, 1990 refers to a method of treating premature ejaculation using sertraline.

U.S. Pat. No. 4,962,128 issued Oct. 9, 1990 refers to a method of treating anxiety related disorders using sertraline.

U.S. Pat. No. 5,130,338 issued Jul. 14, 1992 refers to a method of treating chemical dependencies using sertraline.

U.S. Pat. No. 4,772,288 issued Oct. 11, 1988, U.S. Pat. No. 4,839,104 issued Jun. 13, 1989, U.S. Pat. No. 4,855,500 issued Aug. 8, 1989, U.S. Pat. No. 5,082,970 issued Jan. 21, 1992, and U.S. Pat. No. 5,196,607 issued Mar. 23, 1993, and U.S. patent application Ser. No. 08/178,272 filed Jul. 3, 1992, U.S. patent application Ser. No. 08/178,240 filed Jul. 3, 1992, U.S. patent application Ser. No. 07/806,519 filed Dec. 13, 1991 and U.S. patent application Ser. No. 08/159,156 filed Nov. 30, 1993 all refer to improved processes for the preparation of sertraline.

U.S. Pat. No. 5,248,699 issued Sep. 28, 1993 refers to a novel polymorph of sertraline.

U.S. patent application Ser. No. 08/032,042 filed Mar. 16, 1993 refers to 5HT$_{1D}$ receptor antagonists of formula I, described below, to methods for their preparation, to pharmaceutical compositions containing them and to their use for the treatment or prevention of hypertension, depression, anxiety, eating disorders, obesity, drug abuse, cluster headache, migraine, pain, Alzheimer's disease, chronic paroxysmal hemicrania and headache associated with vascular disorders.

European Patent Application No. 0533268 published Mar. 24, 1993 refers to 5HT$_{1D}$ receptor antagonists.

SUMMARY OF THE INVENTION

The present invention relates to a pharmaceutical composition for treating or preventing disorders arising from deficient or excessive serotonergic neurotransmission in a mammal, preferably a human, comprising:

a) a pharmaceutically acceptable carrier;

b) a compound of the formula

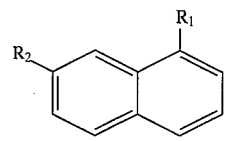

I where R$_1$ is of the formulae

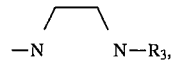

II

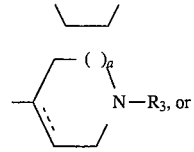

III

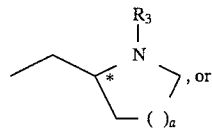

IV

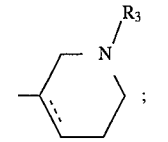

V

R$_2$ is —R$_4$, —O—R$_4$, —O—S(O)$_2$—R$_4$, —NR$_4$R$_5$, R$_4$—(CH$_2$)$_b$, R$_4$—(CH$_2$)$_b$—NH(C=X)—(CH$_2$)$_c$—, R$_4$—(CH$_2$)$_b$—O(C=O)NH—(CH$_2$)$_c$—(C=O)NH—, R$_4$—(C=O)NH—(C=O)NH—, —(CH$_2$)$_b$—NH(C=X)—(CH$_2$)$_c$—R$_4$, R$_4$—(CH$_2$)$_b$—O(C=O)—(CH$_2$)$_c$—,—(CH$_2$)$_b$—O(C=O)—(CH$_2$)$_c$—R$_4$, —NH(C=X)NH—R$_4$, R$_4$—O(C=O)O—, —O(C=O)NH—R$_4$, R$_4$—O(C=O)NH—, —(CH$_2$)$_b$—(C=O)—(CH$_2$)$_c$—R$_4$, —NH—S(O)$_2$—R$_4$, —C(OH)R$_4$R$_5$, —CH(OH)—R$_4$, —(C=O)—NR$_4$R$_5$, —CN —NO$_2$, substituted C$_1$ to C$_6$ alkyl, substituted or unsubstituted C$_1$ to C$_6$ alkenyl, or substituted or unsubstituted C$_1$ to C$_6$ alkynyl, said substituted moieties substituted with a moiety of the formulae —R$_4$, —R$_4$R$_5$, —O—R$_4$, or —S(O)$_d$—R$_4$;

R$_3$ is hydrogen, CH$_3$OCH$_2$CH$_2$, C$_1$ to C$_6$ alkyl, C$_1$ to C$_6$ alkylaryl, or aryl;

R$_4$ and R$_5$ are each independently

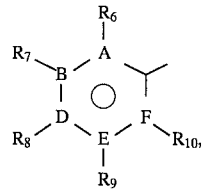

XV

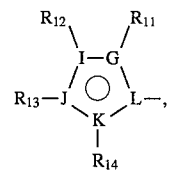

XVI

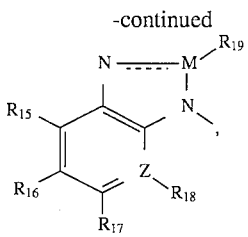

XVII hydrogen, —CF$_3$, C$_1$ to C$_6$ alkyl, C$_1$ to C$_6$ alkylaryl, with the proviso that when R$_2$ is —R$_4$ or —OR$_4$, R$_4$ is not hydrogen or C$_1$ to C$_6$ alkyl;

R$_6$, R$_7$, R$_8$, R$_9$, R$_{10}$, R$_{11}$, R$_{12}$, R$_3$, R$_{14}$, R$_{15}$, R$_{16,}$ R$_7$, and R$_{18}$ are each independently H, halogen, —CF$_3$, —(C=O)R$_{20}$, —CN, —OR$_{20}$, —NR$_{20}$R$_{21}$, —NR$_{20}$SO$_2$R$_{22}$, —N$_{20}$CO$_2$R$_{22}$, —N=C—N(CH$_3$)$_2$, —S(O)$_6$R$_{20}$, —SO$_2$NR$_{20}$R$_{21}$, —NO$_2$, aryl, C$_1$ to C$_6$ alkylaryl, —(C=O)OR$_{20}$, —(C=O)NR$_{20}$R$_{21}$, C$_1$ to C$_6$ alkyl, C$_1$ to C$_6$ alkenyl, and C$_1$ to C$_6$ alkynyl;

R$_6$ and R$_7$, R$_7$ and R$_8$, R$_8$ and R$_9$, R$_9$ and R$_{10}$, R$_{11}$ and R$_{12}$, R$_{12}$ and R$_{13}$, R$_{13}$ and R$_{14}$, R$_{15}$ and R$_{16}$, R$_{16}$ and R$_{17}$ and R$_{18}$ may be taken together to form a five-to-seven-membered alkyl ring, a six-membered aryl ring, a five to seven membered heteroalkyl ring having one heteroatom of N, O, or S, or a five-to six-membered heteroaryl ring have 1 or 2 heteroatoms of N, O, or S;

R$_{19}$ is hydrogen or C$_1$ to C$_3$ alkyl;

R$_{20}$ and R$_{21}$ are each independently hydrogen, C$_1$ to C$_6$ alkyl, aryl, or C$_1$ to C$_6$ alkylaryl, or may be taken together to form a C$_4$ to C$_7$ alkyl ring;

R$_{22}$ is C$_1$ to C$_6$ alkyl, aryl, or C$_1$ to C$_6$ alkylaryl;

A, B, D, E, and F are each independently C, N, or (C=O);

G, I, J, and K are each independently C, N, O, S, or (C=O), with the proviso that there is at most one of O, (C=O), or S per ring;

L and Z are each independently C or N;

M is C, N, or (C=O);

X is O or S;

a is 0, 1 or 2;

e is 0, 1 or 2;

d is 0, 1, or 2;

b and c are each independently 0, 1, 2, 3, 4, 5, or 6, with b+c being at most 6;

a broken line indicates the presence optionally of a double bond and the above aryl groups and the aryl moieties of the above alkylaryl groups are independently selected from phenyl and substituted phenyl, wherein said substituted phenyl may be substituted with one to three groups selected from C$_1$ to C$_4$ alkyl, halogen, hydroxy, cyano, carboxamido, nitro, and C$_1$ to C$_4$ alkoxy, and pharmaceutically acceptable salts thereof; and c) a 5-HT re-uptake inhibitor, preferably sertraline, or a pharmaceutically acceptable salt thereof;

wherein the amounts of the active compounds is such that the combination is effective in treating or preventing such condition.

The present invention also relates to a method for treating or preventing disorders arising from deficient or excessive serotonergic neurotransmission in a mammal, preferably a human, comprising administering to said mammal requiring such treatment or prevention:

a) a compound of the formula I defined above, and pharmaceutically acceptable salts thereof; and b) a 5-HT re-uptake inhibitor, preferably sertraline, or a pharmaceutically acceptable salt thereof;

wherein the amounts of the active compounds is such that the combination is effective in treating or preventing such condition.

The present invention relates to a pharmaceutical composition for treating or preventing a condition selected from mood disorders, including depression, seasonal affective disorders and dysthmia, anxiety disorders including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa; obesity; cluster headache; migraine; pain; Alzheimer's disease; chronic paroxysmal hemicrania; headache associated with vascular disorders; Parkinson's disease, including dementia in Parkinson's disease, neuroleptic-induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies in a mammal, preferably a human, comprising:

a) a pharmaceutically acceptable carrier;

b) a compound of the formula I defined above, and pharmaceutically acceptable salts thereof; and c) sertraline or a pharmaceutically acceptable salt or polymorph thereof;

wherein the amounts of the active agents is such that the combination is effective in treating or preventing such condition.

The present invention also relates to a method for treating or preventing a condition selected from mood disorders, including depression, seasonal affective disorders and dysthmia, anxiety disorders including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa; obesity; cluster headache; migraine; pain; Alzheimer's disease; chronic paroxysmal hemicrania; headache associated with vascular disorders; Parkinson's disease, including dementia in Parkinson's disease, neuroleptic-induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies in a mammal, preferably a human, comprising administering to said mammal requiring such treatment or prevention:

a) a compound of formula I as defined in claim 1 or a pharmaceutically acceptable salt thereof; and b) sertraline or a pharmaceutically acceptable salt or polymorph thereof;

wherein the amounts of the active agents is such that the combination is effective in treating or preventing such condition.

The present invention also relates to a pharmaceutical composition for treating or preventing a condition selected from mood disorders, including depression, seasonal affective disorders and dysthmia, anxiety disorders including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa;

obesity; cluster headache; migraine; pain; Alzheimer's disease; chronic paroxysmal hemicrania; headache associated with vascular disorders; Parkinson's disease, including dementia in Parkinson's disease, neuroleptic induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies in a mammal, preferably a human, comprising:

a) a pharmaceutically acceptable carrier;

b) a serotonin 1 (5-HT$_1$) receptor agonizing or antagonizing effective amount of a compound of formula I as defined above or a pharmaceutically acceptable salt thereof; and c) a serotonin re-uptake inhibiting effective amount of sertraline or a pharmaceutically acceptable salt or polymorph thereof.

The present invention also relates to a method of treating or preventing a condition selected from mood disorders, including depression, seasonal affective disorders and dysthmia, anxiety disorders including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa; obesity; cluster headache; migraine; pain; Alzheimer's disease; chronic paroxysmal hemicrania; headache associated with vascular disorders; Parkinson's disease, including dementia in Parkinson's disease, neuroleptic-induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies in a mammal, preferably a human, comprising administering to said mammal:

a) a serotonin 1 (5-HT$_1$) receptor agonizing or antagonizing effective amount of a compound of formula I as defined above or a pharmaceutically acceptable salt thereof; and b) a serotonin re-uptake inhibiting effective amount of sertraline or a pharmaceutically acceptable salt or polymorph thereof.

"Serotonergic neurotransmission" when used herein refers to the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Vallium (trademark)). "Treating a chemical dependency," as used herein, means reducing or alleviating such dependency.

The compounds of formula I include all optical isomers of formula 1 (e.g. R and S enantiomers) and their racemic and diastereomeric mixtures. When R$_1$ is

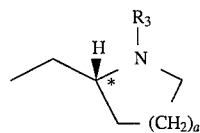

the R enantiomers at the chiral carbon designated by an asterisk in formula 1 are preferred. These compounds are useful as intermediates in preparing compounds of formula I.

Unless otherwise indicated, the alkyl and alkenyl groups referred to herein, as well as the alkyl moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties. Unless otherwise indicated, halogen includes fluorine, chlorine, bromine, and iodine.

Sertraline, (1S-cis)-4-(3,4- dichlorophenyl)-1,2,3,4-tetrahydro-N-methyl-1-naphthalenamine, as used herein has the chemical formula $C_{17}H_{17}NCl_2$ and the following structural formula

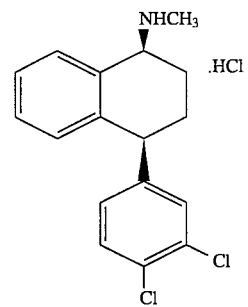

Its synthesis is described in U.S. Pat. No. 4,536,518, assigned to Pfizer Inc. Sertraline hydrochloride is useful as an antidepressant and anorectic agent, and is also useful in the treatment of depression, chemical dependencies, anxiety-related disorders and premature ejaculation.

Preferred embodiments of the present invention include pharmaceutical compositions comprising and methods of administering compounds of formula I, or pharmaceutically acceptable salts of these compounds with a 5-HT re-uptake inhibitor, preferably sertraline, or pharmaceutically acceptable salts or polymorphs thereof; wherein said compound of formula 1 is a compound wherein R$_1$ is formula II; R$_2$ is —R$_4$, —OR$_4$, R$_4$—(CH$_2$)$_b$—NH(C=X)—(CH$_2$)$_c$—, or —(CH$_2$)$_b$—NH(C=O)—(CH$_2$)$_c$—R$_4$; R$_3$ is hydrogen or C$_1$ to C$_6$ alkyl; R$_4$ is formula XV or formula XVII; A, B, D, E, and F are each independently C or N; R$_6$, R$_7$, R$_8$, R$_9$, R$_{10}$, R$_{15}$, R$_{16}$, R$_{17}$, R$_{18}$, and R$_{19}$ are each independently hydrogen, halogen, —CN, or —OR$_{20}$; and R$_{20}$ is C$_1$ to C$_6$ alkyl.

Preferred embodiments of the present invention include pharmaceutical compositions comprising and methods of administering compounds of formula I, or pharmaceutically acceptable salts of these compounds with a 5-HT re-uptake inhibitor, preferably sertraline, or pharmaceutically acceptable salts or polymorphs thereof; wherein said compound of formula I is a compound wherein R$_1$ is formula III; R$_2$ is —R$_4$, —OR$_4$, R$_4$—(CH$_2$)$_b$—NH(C=X)—(CH$_2$)$_c$—, or —(CH$_2$)$_b$—NH(C=)—(CH$_2$)$_c$—R$_4$; R$_4$ is formula XV or formula XVII; R$_3$ is hydrogen or C$_1$ to C$_6$ alkyl; A, B, D, E, and F are each independently C or N; R$_6$, R$_7$, R$_8$, R$_9$, R$_{10}$, R$_{15}$, R$_{16}$, R$_{17}$, R$_{18}$, and R$_{19}$ are each independently hydrogen, halogen, —CN, or —OR$_{20}$; and R$_{20}$ is C$_1$ to C$_6$ alkyl.

Preferred embodiments of the present invention include pharmaceutical compositions comprising and methods of administering compounds of formula I, or pharmaceutically acceptable salts of these compounds with a 5-HT re-uptake inhibitor, preferably sertraline, or pharmaceutically acceptable salts or polymorphs thereof; wherein $R_1$ is

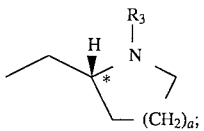

$R_2$ is —$R_4$, —$OR_4$, $R_4$—$(CH_2)_b$—NH(C=X)—$(CH_2)_c$—, or —$(CH_2)_b$—NH(C=O)—$(CH_2)_c$—$R_4$; $R_3$ is hydrogen or $C_1$ to $C_6$ alkyl; $R_4$ is formula XV or formula XVII; A, B, D, E, and F are each independently C or N; $R_6$, $R_7$, $R_8$, $R_9$, $R_{10}$, $R_{15}$, $R_{16}$, $R_{17}$, $R_{18}$, and $R_{19}$ are each independently hydrogen, halogen, —CN, or —$OR_{20}$; and $R_{20}$ is $C_1$ to $C_6$ alkyl.

Preferred embodiments of the present invention include pharmaceutical compositions comprising and methods of administering compounds of formula I, or pharmaceutically acceptable salts of these compounds with a 5-HT re-uptake inhibitor, preferably sertraline, or pharmaceutically acceptable salts or polymorphs thereof; wherein said compound of formula I is a compound wherein $R_1$ is formula II, formula III, or formula IV; $R_2$ is —$R_4$; $R_3$ is hydrogen or $C_1$ to $C_6$ alkyl; $R_4$ is formula XVII; G, I, J, and K are each independently C, N, or O; L is C; $R_{11}$, $R_2$, $R_{13}$, and $R_{14}$ are each independently hydrogen, $C_1$ to $C_6$ alkyl, or $C_1$ to $C_6$ alkylaryl.

Preferred embodiments of the present invention include pharmaceutical compositions comprising and methods of administering the following compounds of formula I, or pharmaceutically acceptable salts of these compounds with sertraline or pharmaceutically acceptable salts or polymorphs thereof:

7-Benzamido-1-(4-methyl-1-piperazinyl)-naphthalene;
7-(1-Naphthylcarboxamido)-1-(4-methyl-1-piperazinyl)-naphthalene;
7-Benzamido-1-(1-piperazinyl)-naphthalene;
7-Acetamido-1-(4-methyl-1-piperazinyl)-naphthalene;
7-Hexanamido-1-(4-methyl-1-piperazinyl)-naphthalene;
7-(Phenylaminocarbonylamino)-1-(4-methyl-1-piperazinyl)-naphthalene;
7-(Benzyloxycarbonylamino)-1-(4-methyl-1-piperazinyl)-naphthalene;
7-(3-Nitro-2-pyridinylamino)-1-(4-methyl-1-piperazinyl)-naphthalene;
7-(5-Nitro-2-pyridylamino)-1-(4-methyl-1-piperazinyl)-naphthalene;
7-(3-Hydroxy-3-methyl-1-butynyl)-1-(4-methyl-1-piperazinyl)-naphthalene;
7-(2-Ethylsulfonyl)ethenyl-1-(4-methyl-1-piperazinyl)-naphthalene;
7-(4-Chlorobenzyloxy)-1-(4-methyl-1-piperazinyl)-naphthalene;
7-(3-Methylaminosulfonylphenyl)-1-(4-methyl-1-piperazinyl)naphthalene;
7-(3-Methylsulfonylaminophenyl)-1-(4-methyl-1-piperazinyl)-naphthalene;
7-Benzoyl-1-(4-methyl-1-piperazinyl)naphthalene;
7-(3-Methoxycarbonylphenyl)-1-(4-methyl-1-piperazinyl)-naphthalene;
7-(3-Fluorophenyl)-1-(4-methyl-1-piperazinyl)-naphthalene;
7-(Benzyloxy)-1-(4-methyl-1-piperazinyl)-naphthalene;
7-(4-Chlorobenzoyloxy)-1-(4-methyl-1-piperazinyl)-naphthalene;
7-(Imidazolo[4,5-b]pyridin-1-yl)-1-(4-methyl-1-piperazinyl)-naphthalene;
7-(Benzimidazol-1-yl)-1-(4-methyl-1-piperazinyl)-naphthalene;
7-(5-Cyanobenzimidazol-1-yl)-1-(4-methyl-1-piperazinyl)-naphthalene;
7-(1,2,3-Triazolo[4,5-b]pyridin-1-yl)-1-(4-methyl-1-piperazinyl)-naphthalene;
7-(5-Trifluoromethylbenzimidazol-1-yl)-1-(4-methyl-1-piperazinyl)-naphthalene;
7-(6,7-Dichlorobenzimidazol-1-yl)-1-(4-methyl-1-piperazinyl)-naphthalene;
2-[8-(4-Methylpiperazin-1-yl)naphthalen-2-yloxymethyl]quinoline;
1-Methyl-4-{7-[2-(4-chlorophenyl)thiazol-5-ylmethoxy]naphthalen-1-yl}piperazine;
1-Methyl-4-[7-(5-chloro-thiophen-2-ylmethoxy)napthalen-1-yl]piperazine;
8-(4-Methylpiperazin-1-yl)naphthalene-2-carboxylic acid phenylamide;
7-Amino-1-(1-methyl-4-piperidinyl)-naphthalene;
7-(3-Nitro-2-pyridylamino)-1-(1-methyl-4-piperidinyl)-naphthalene;
7-(Imidazolo[4,5-b]pyridin-1-yl)-1-(1-methyl-4-piperidinyl)-naphthalene;
7-(4-Chlorobenzamido-1-(1-methyl-4-piperidinyl)-naphthalene;
7-Amino-1-(1-methyl-3-piperidinyl)-naphthalene;
7-(3-Nitro-2-pyridylamino)-1-(1-methyl-3-piperidinyl)-naphthalene;
7-(Imidazolo[4,5-b]pyridin-1-yl)-1-(1-methyl-3-piperidinyl)-naphthalene;
7-Benzamido-1-(1-methyl-3-piperidinyl)-naphthalene;
7-(4-Chlorobenzamido)-1-(4-methoxyethyl-1-piperazinyl)-naphthalene;
7-(4-Chlorobenzamido)-1-(4-propyl-1-piperazinyl)-naphthalene;
7-(4-Chlorobenzamido)-1-(4-ethyl-1-piperazinyl)-naphthalene;
7-Amino-1-(1-methyl-3-pyrrolidinyl)-naphthalene;
7-Benzamido-1-(1-methyl-3-pyrrolidinyl)-naphthalene;
7-Formamido-1-(pyrrolidin-2-(R)-ylmethyl)-naphthalene hydrochloride;
7-Amino-1-(1-piperazinyl)-naphthalene;
7-(Imidazolo-[4,5-b]-pyridin-1-yl)-1-(1-piperazinyl)-naphthalene; and
7-(1,2,3-Triazolo-[4,5-b]-pyridin-1-yl)-1-(1-piperazinyl)-naphthalene;

The following compounds are particularly preferred:
7-(Imidazolo[4,5-b]pyridin-1-yl)-1-(1-methylpyrrolidin-3-yl)naphthalene;
7-(4-Chlorobenzamido)-1-(pyrrolidin-2-(R)-ylmethyl)naphthalene;
2-[8-(4-Methylpiperazin-1-yl)naphthalen-2-yloxy]nicotinonitrile;
1-(4-Methylpiperazin-1-yl)-7-pyrimidin-5-yl)naphthalene;
7-(5-Cyanopyridin-3-yl)-1-(4-methylpiperazin-1-yl)naphthalene;
1-(Piperazin-1-yl)-7-(pyrimidin-5-yl)naphthalene;
7-(4-Chlorobenzamido-1-(4-methylpiperazin-1-yl)naphthalene;
7-(3-Methoxyphenyl)-1-(4-methylpiperazin-1-yl)naphthalene;
7-(Imidazolo[4,5-b]pyridin-1-yl)-1-(4-methylpiperazin-1-yl)naphthalene;
8-(4-Methylpiperazin-1-yl)naphthalene-2-carboxylic acid 4-chlorobenzylamide;

7-Pyrimidin-2-yloxy-1-(4-methylpiperazin-1-yl)naphthalene;

7-(4-Methoxyphenyl)-1-(4-methylpiperazin-1-yl)-naphthalene;

7-(Benzimidazol-1-yl)-1-(4-methylpiperazin-1-yl)naphthalene; and 8-(1-Methylpiperidin-4-yl)naphthalene-2-carboxylic acid 4-chlorobenzylamide.

DETAILED DESCRIPTION OF THE INVENTION

Compounds of formula I of this invention where $R^1$ is of the formula II are prepared by the following reaction of an α-tetralone of formula V with a suitable piperazine of formula VI.

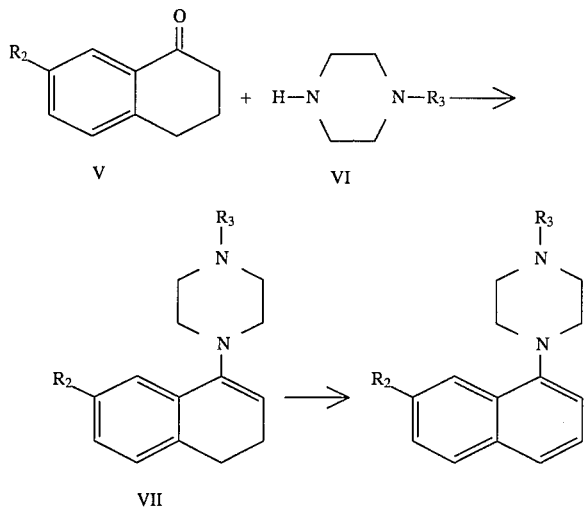

The so called enamines of formula VII are generally prepared by this reaction in the presence of an acid catalyst such as, for example, p-toluenesulfonic acid or titanium tetrachloride. If desired, the water formed as a by-product of the reaction may be effectively removed from the reaction as it is formed by the use of a reagent such as molecular sieves or calcium sulfate, or by azeotropic removal employing a Dean Stark trap with a refluxing solvent. The reaction is typically run in a reaction inert solvent such as benzene, toluene, tetrahydrofuran, or methylene chloride, at a temperature of from about −78° C. to about 150° C. When titanium tetrachloride is used as the acid catalyst, the preferred temperature for the reaction is from about −78° C. to about 25° C. When azeotropic water separation is employed, the preferred reaction temperature is the boiling temperature of the particular reaction solvent.

In general, the α tetralones of formula V, for example, where $R_2$ is —OH, —NO$_2$, or —NH$_2$ are known in the literature and can be readily prepared by those skilled in the art, such as, for example 7-amino-α-tetralone, (J. Med. Chem., 1976, 19, 472) and 7-hydroxy-α-tetralone, (Tetrahedron Lett., 1981, 22,603). Other α tetralones of formula V are readily prepared using the alkylation, acylation, and organometallic reactions described herein and in standard synthesis texts, for example *Organic Synthesis*, Wiley, New York). The piperazines of formula VI are commercially available or can be made using methods known in the art.

The enamines of formula VII may be converted to compounds of formula I by an oxidative process. The reaction may be carried out using a variety of methods known in the art. Among the acceptable oxidizing agents are noble metal catalysts, such as, palladium or platinum on activated carbon if desired, chloranil, and sulfur. The reactions can be carried out in a reaction inert solvent for example, toluene, xylene, tetrahydrofuran, methylene chloride, preferably toluene or xylene, however a solvent is not always necessary, especially for oxidations carried out with elemental sulfur. The oxidation reactions generally proceed at a temperature of about 0° C. to about 250° C. Preferred temperatures for the oxidation depend on the particular oxidant in use and are about 60° C. to about 150° C. for noble metal catalytic oxidation, about 150° C. to about 250° C. for sulfur oxidation and about 0° C. to about 100° C. for chloranil oxidations. From 1 to 5 equivalents, preferably 2–4 equivalents, of an additive such as dicyclopentadiene or [2,2,2] bicyclooctene may be added to the reaction to reduce the amounts of enamine reduction side products which may form competitively with the desired naphthalene product.

Additional compounds of formula 1 may also be formed using standard chemical transformations on other compounds of formula I. For example, when $R_2$ is $R_4(C=O)NH—$ or $R_4(C=O)O—$, these groups may be hydrolyzed in the presence of aqueous acid or base to form —NH$_2$ and —OH groups, respectively. These standard hydrolysis reactions may be carried out in water with any of a variety of acids or bases (for example HCl, HBr, NaOH, or KOH, preferably acid for amidehydrolysis and base for ester hydrolysis) and a cosolvent (methanol or tetrahydrofuran, for example) may be used if desired to promote dissolution of I in the medium. The reaction may be carried out at a temperature of from about 0° C. to about 150° C. The preferred reaction temperature is about 20° C. to about 40° C. for basic hydrolysis and about the boiling temperature of the mixture for acidic hydrolysis.

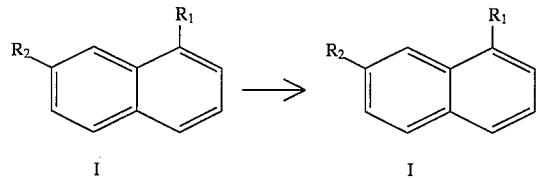

$R_2 = R_4(C=O)O—,$
$R_4(C=O)NH—$ $R_2 = OH, NH_2$

Additional compounds of formula 1 may be prepared by a reaction using an alkylating or acylating agent (alkyl halide, mesylate, triflate, etc., or arylalkyl halide, mesylate, triflate, etc., or an alkyl or aryl anhydride, or an alkyl or aryl carboxylic acid chloride, etc.) with compounds of formula 1 where $R_2=$—NH$_2$ or —OH. Suitable alkylating agents could include compounds of the formulae $R_4—(CH_2)_b—Y$ or $R_5—(CH_2)_b—Y$ where b is 0 to 3 and Y is a suitable leaving group, such as, for example, Br, I, or triflate. Suitable acylating agents could include acid chlorides (e.g. $R_4—(CH_2)_b—(C=O)—Cl$ or $R_5—(CH_2)_b—(C=O)—Cl)$ or acid anhydrides (e.g. $(R_4—(CH_2)_b—(C=O))_2—O$ or $(R_5—(CH_2)_b—(C=O))_2—O$, where b is 0 to 3). The reaction may be carried out in a reaction inert solvent such as tetrahydrofuran and dichloroethane for the alkylating and acylating reactions. Preferred solvents depend on the solubility of the reagents and the selection thereof would be known to one skilled in the art. These alkylation or acylation reactions are carried out at temperatures of between about 0° C. to about 200° C. depending on the nature of the reaction. Preferred temperatures are between about 0° C. to about 75° C. for the acylation reactions and between about 25° C. to about 100° C. for the alkylation reactions.

Additional compounds of formula I may be prepared by the well known reductive alkylation reaction of the compounds of formula I where $R_2$ is —$NH_2$ with aldehydes and ketones in the presence of hydrogen gas and a platinum or palladium catalyst or in the presence of a reducing agent such as sodium cyanoborohydride.

Other compounds of formula I can be synthesized using an activated aromatic or heterocylic compound, which are either commercially available or can be produced using methods known in the art. To form the additional compounds, these reactants are reacted with compounds of formula 1 where $R_2$ is OH or $NH_2$. As shown below, the term activated aromatic or heterocyclic compound implies a ring compound of formulae VIII or IX;

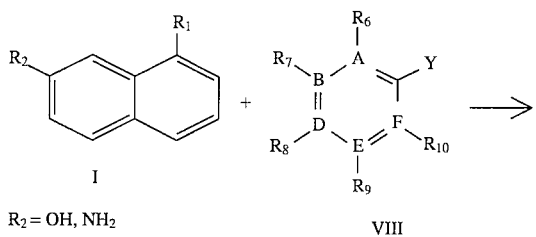

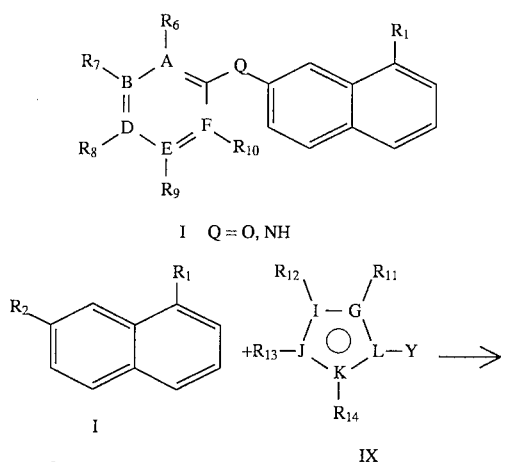

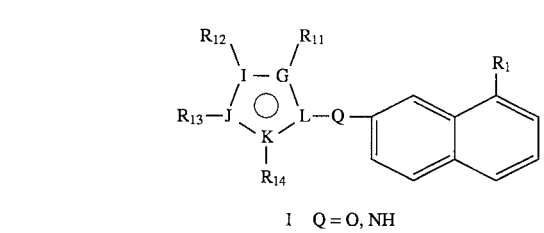

where Y is a suitable leaving group (for example halogen or trifluoromethanesulfonyloxy) and the ring is rendered susceptible to nucleophilic attack by the presence of one or more nitrogen atoms in the ring or by the presence of one or more electron withdrawing groups (in other words one or more of $R_6$, $R_7$, $R_8$, $R_9$, $R_{10}$, $R_{11}$, $R_{12}$, $R_{13}$, or $R_{14}$ are halogen, —$CF_3$, nitro, cyano, alkoxycarbonyl, amidocarbonyl, etc.) attached to the ring. Values for A, B, D, E, F, G, I, J, K, and $R_6$, $R_7$, $R_8$, $R_9$, $R_{10}$, $R_{11}$, $R_{12}$, $R_{13}$, and $R_{14}$ may be selected from those described previously. Solvents suitable for use with the activated aromatic or heterocylic compounds include, for example, dimethylformamide, N-methypyrrolidinone, or methylene chloride and a base (for example triethylamine, 4-dimethylaminopyridine, sodium or potassium carbonate, sodium hydride) may be used to facilitate the process if desired. Preferred solvents depend on the solubility of the reagents and the selection thereof would be known to one skilled in the art. These alkylation or acylation reactions are carried out at temperatures of between about 0° C. to about 200° C. depending on the nature of the reaction. Preferred temperatures are between about 50° C. to about 125° C. for these reactions.

The alkylation and acylation procedures described above can also be useful in synthesizing of intermediates of formula V.

Compounds of formula I where $R_2$ is one of the claimed alkyl, alkenyl, or alkynyl moieties can be prepared by reaction of compounds of formula I where $R_2$ is $CF_3SO_3$ with an appropriate olefin or acetylene compound in the presence of a palladium catalyst. The selection of appropriate olefin or acetylene depends on the alkyl, alkenyl, or alkynyl moiety desired in the end product, as would be appreciated by one skilled in the art. The alkenyl and alkynyl substituted compounds can be produced using the following reaction scheme:

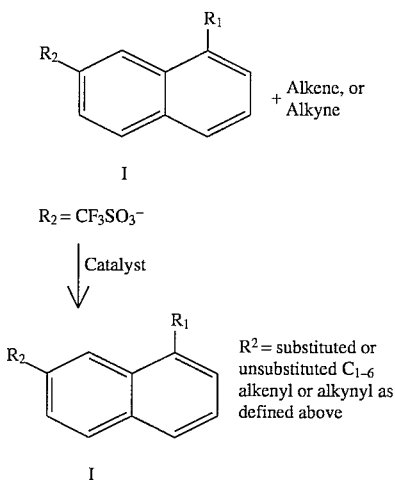

The catalyst may be selected from those typically employed for the so-called Heck reaction (palladium acetate, palladium chloride, bis (acetonitrile) palladium chloride, for example). The reaction is carried out neat or in a reaction inert solvent such as acetonitrile, dimethylformamide, or N-methylpyrrolidinone. The reaction is conveniently run at 20° C. to 160° C., preferably 60° C. to 130° C. The details of reactions of this type have been well described in the literature (Organic Reactions 1982, 27, 345).

The synthesis of compounds having the claimed alkyl moieties require the additional step of reducing the product of the reaction discussed in the previous paragraph. The reduction is performed using standard methods known in the art.

The Heck reaction can also be useful in the synthesis of intermediates of formula V, as is known in the art.

The compounds of formulae I and intermediates of formula V where $R_2$ is $CF_3SO_3$ can be prepared by reacting the corresponding $R_2$ substituted hydroxy compounds of formulae I or V with an activated form of triflic acid, for example, triflic anhydride, acid chloride, N-phenyltrifluoromethanesulfonimide, preferably triflic anhydride, typically in the presence of a base, such as, for example, triethylamine or diisopropylethylamine, preferably triethylamine. The reaction may be run in an inert solvent, such as, tetrahydrofuran or methylene chloride, at a temperature of from about −78° C. to about 25° C., preferably below about 0° C. This procedure is known in the art, as shown, for example, in J. Amer. Chem. Soc., 1987, 109, 5478.

A method to prepare the compounds of formula I where $R_2$ is $R_4$ or $R_4(CH_2)_b(C=O)(CH_2)_c-$ is accomplished by reacting compounds of formula I where $R_2$ is trimethylstannyl or tributylstannyl with an aryl or vinyl halide, or an aryl or vinyl triflate, or an aryl or alkyl acid chloride or a heteroaryl halide or triflate in the presence of a catalyst, preferably tetrakis(triphenylphosphine)palladium or tris-(dibenzylideneacetone)dipalladium, and is shown in the following reaction scheme:

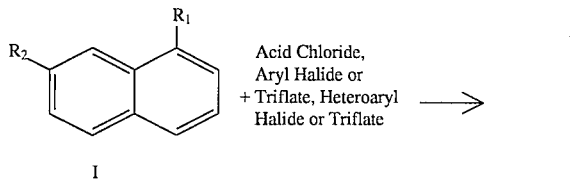

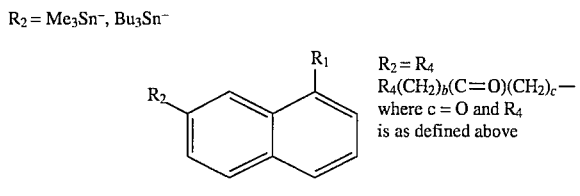

The procedures and conditions to carry out this reaction are known to those in the art, for example, in Angew. Chem. Int. Ed. Engl., 1986, 25, 508. The triflate variant of this reaction is also known in the art, for example, in J. Amer. Chem. Soc., 1987, 109, 5478. A further variation of this type of process which uses an alkyl or aryl halide in the presence of carbon monoxide gas and a palladium catalyst is also known, for example, in J. Amer. Chem. Soc., 1988, 110, 1557.

It will be recognized by one skilled in the art that the coupling reactions described above may also be used to prepare the intermediates of formula V.

The stannane compounds I and V may be prepared from the compound I ($R_2$ being $CF_3SO_3$) following known literature procedures (J. Amer. Chem. Soc., 1987, 109, 5478).

A method to prepare compounds of formula I where $R_2$ is $R_4$ is accomplished by reacting compounds of formula I where $R_2$ is bromo, iodo, or $-OSO_2CF_3$ with an arylstannane, arylboronic acid, heteroaryl boronic acid, or heteroarylstannane in the presence of a catalyst, preferably tetrakis(triphenylphosphine)palladium, in an inert solvent, and is shown in the following scheme:

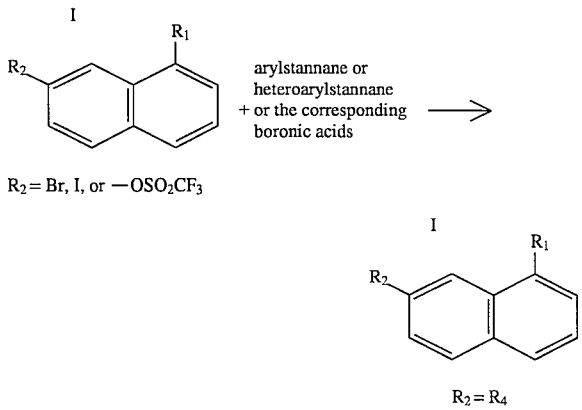

The procedures and conditions to carry out this reaction are known to those skilled in the art, for example, in Angew. Chem. Int. Ed. Engl., 1986, 25, 508. The triflate variant of this reaction is also known in the art, for example, in J. Am. Chem. Sot., 1987, 109, 5478. The required arylstannanes or heteroarylstannanes are available by methods known to one skilled in the art, for example, in J. Am. Chem. Soc, 1987, 109, 5478. The procedure and conditions for boronic acid couplings are described in J. Org. Chem. 1993, 58, 2208.

A method of preparing compounds of formula I and intermediates of formula V where $R_2$ is $-O-R_4$ is to react corresponding compounds of formula I or intermediates of formula V where $R_2$ is $-OH$ with alcohols, for example, ethanol or benzyl alcohol, in the presence of triphenylphosphine and diethyl azodicarboxylate in a Mitsunobu reaction. Mitsunobu reactions are known in the art, for example, as disclosed in Synthesis 1981, 1.

Further compounds of formula 1 where $R_2$ is $R_4-(CH_2)_b-O-(C=O)-(CH_2)_c-$ or $R_4(CH_2)_b-NH-(C=X)-(CH_2)_c-$ and c is 0 may be prepared by reaction of compounds of the formula I where $R_2$ is $OSO_2CF_3$ with an alcohol or an amine and carbon monoxide in the presence of a palladium catalyst. Hydrolysis of the resulting esters or amides to the corresponding acids and treatment following the general procedures outlined in EP 0 438 230 A2 further allow the preparation of additional compounds of formula I where $R_2$ is $-R_4$ and $R_4$ is of formula XVI [e.g., a (1,2,4-oxadiazol-5-yl)-naphthalene].

Compounds of formula 1 may also be prepared using standard functional group manipulations known in the art and which are disclosed in various standard synthetic chemistry texts. Examples of these are discussed below.

When $R_2$ is $R_4(CH_2)_b(C-O)(CH_2)_c-$, it may be reacted with a reducing agent, to yield the corresponding alcohol. Standard methods known in the art can be used. Useful reducing agents include sodium borohydride, lithium aluminum hydride, or borane (or any of its complexes).

Compounds of formula I where the $R_2$ substituent includes a ketone or ester carbonyl moiety may be treated with organometallic agents, such as alkyl- and aryl lithiums, or Grignard reagents using methods known in the art. In this reaction, the resulting compounds will be tertiary alcohols ($R_2=-C(OH)R_4R_5$).

When $R_2$ contains an amide group, treatment with a reducing agent, such as, for example, lithium aluminum hydride or borane using known methods, produces the corresponding alkylated (or aralkylated) secondary or tertiary amines.

Another example of the interconversion of compounds of formula I is the reduction of a nitro group of an $R_2$ substituent including a nitrophenyl or nitropyridyl group to the corresponding amine. For example, as shown below,

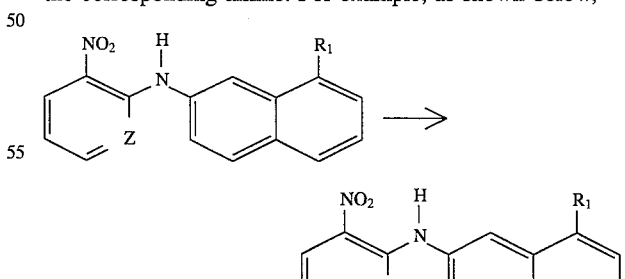

where $R_1$ and Z are as defined above, the reaction may be carried out using known nitro group reducing agents and methods, for example, hydrogenation over noble metal catalysts (palladium or platinum on a support, such as carbon, if desired) or by dissolving metal reduction.

In a further example of the interconversion of the compounds of formula I, the product of the previous reaction scheme may be cyclized with, for example, dimethylformamide dimethyl acetal or triethyl orthoformate to produce fused imidazole compounds of formula I, as shown below,

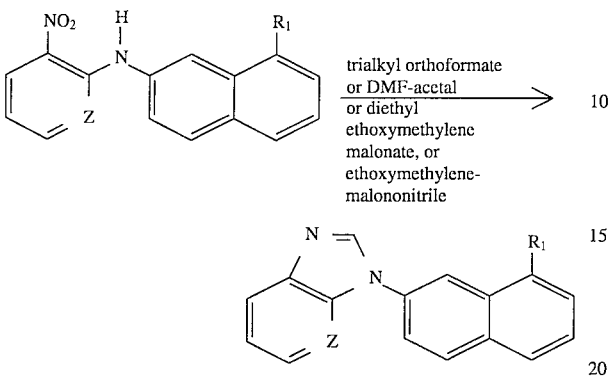

The reaction may be carried out in an inert solvent, such as, for example, dimethylformamide, ethanol, or dimethyl sulfoxide, preferably dimethylformamide. The reaction is run at a temperature of from about 20° C. to about 125° C. If desired, an acid catalyst, such as, p-toluenesulfonic acid or camphor sulfonic acid, preferably p-toluenesulfonic acid, may also be used to facilitate the reaction. In some cases the amidine compounds of formula I can be isolated, especially when the acid catalyst is not used.

Another method to carry out the reaction shown in the previous scheme employs diethyl ethoxymethylenemalonate, ethoxymethylenemalononitrile, or related reagents preferably ethoxymethylenemalononitrile, as the cyclization reagent. This reaction may be run in an inert solvent, such as, acetic acid, ethanol, or isopropanol, preferably isopropanol or acetic acid. The reaction temperature should be from about 25° C. to about 150° C. The preferred temperature is the reflux temperature of the solvent for convenience and to decrease the reaction time.

Compounds of formula I where $R_1$ is tetrahydropyridine, piperidine, or azacycloalkylmethyl may be prepared from 8-bromo-β-tetralone, which is known in the art, for example in U.S. Pat. No. 4,897,405, as shown in the following reaction scheme:

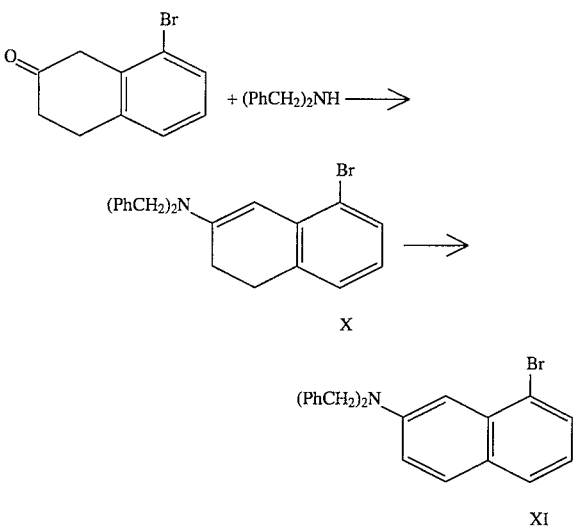

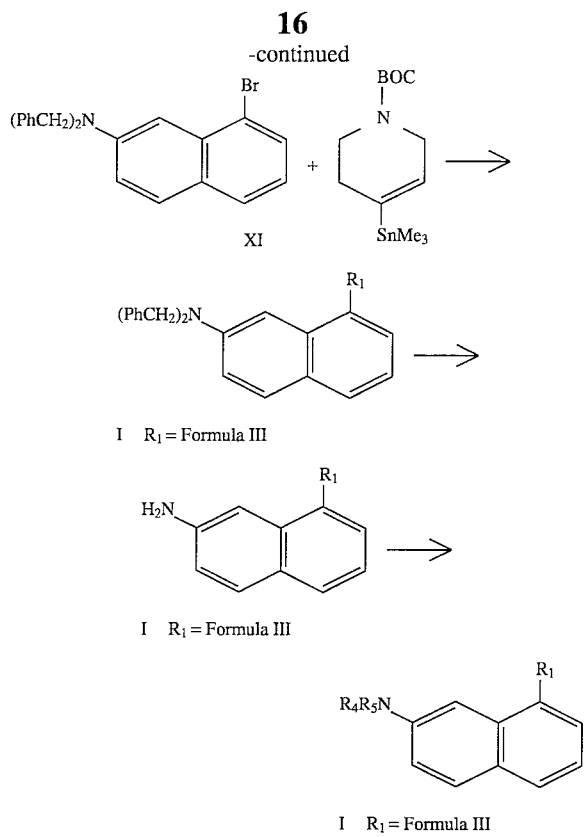

The 8-bromo-β-tetralone is first reacted with an amine, for example, dibenzylamine to form an enamine X using the same procedure disclosed previously on page 8. The enamine X can be dehydrogenated as described above on page 9, chloranil being the preferred reagent with these particular reactants, to yield 1-bromo-7-amine substituted naphthalenes XI. Selection of an appropriate amine for the enamine-forming step would be apparent to one skilled in the art, for example, diallylamine and dibenzylamines for instance. Compounds XI can be then treated with vinylstannanes, for example, 1-BOC-4-trimethylstannyl-1,2,5,6-tetrahydropyridine (BOC=tertbutyloxycarbonyl), shown in the above scheme, in the presence of a catalyst. Palladium is the preferred catalyst, for example $(Ph_3P)_4Pd$ or $Pd_2(dba)_3$ and the reaction follows the same procedures as described above on pages 12 to 14, where $R_1$ is tetrahydropyridine in a so-called Stille and Heck reactions.

Compounds of formula I where $R_1$ is piperidine can be prepared by catalytic hydrogenation of the tetrahydropyridine from the previous paragraph, using standard methods known in the art, generally with palladium on carbon as the catalyst. Compounds I where $R_1$ is piperidine or tetrahydropyridine can be produced, for example, by removal of the benzyl groups (when $R_2$ is dibenzylamino) by catalytic hydrogenolysis, using a suitable catalyst such as palladium hydroxide, palladium on carbon, or platinum on carbon, preferably palladium hydroxide. The reaction is performed in an inert solvent, such as ethanol or ethyl acetate, either with or without a protic acid, such as acetic acid or HCl. The preferred acid is acetic acid. In this case, the resulting compounds are of formula I where $R_2$ is amino. The amino group can be derivatized using standard techniques known in the art and as described previously on pages 10 to 16 to afford further compounds of formula I with substituted amines.

Compounds of formula XI from the previous reaction scheme may also be treated with alkyllithium reagents, for example, butyllithium, sec-butyllithium or tertbutyllithium, preferably butyllithium in an inert solvent, as shown below,

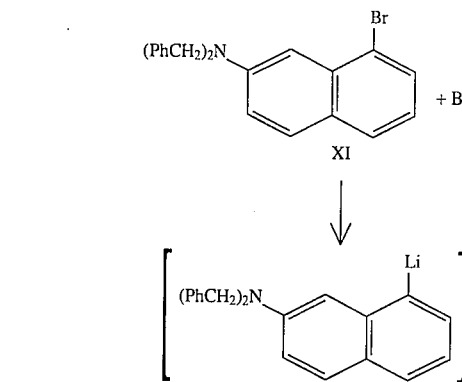

Suitable solvents include, for example, ether or tetrahydrofuran, preferably tetrahydrofuran. Reaction temperatures range from about −110° C. to about 0° C. The intermediate lithium anions of formula XII thus formed may then be further reacted with a suitable electrophile, selection of which depends on the desired substituent at the $R_1$ position. Suitable electrophiles to prepare compounds I where $R_1$ is formula III or IV include, for example, carbonyl derivatives or alkylating agents (e.g., 1-BOC-4-piperidone, 1-BOC-prolinal or 1-FMOC-2-chloromethylpyrrolidine (FMOC= fluorenylmethoxycarbonyl)).

In the case where an aldehyde or ketone is used as the electrophile, the intermediates XIII, XIV, or XX which are formed require that the hydroxy group be removed so as to result in compounds of formula I as shown below,

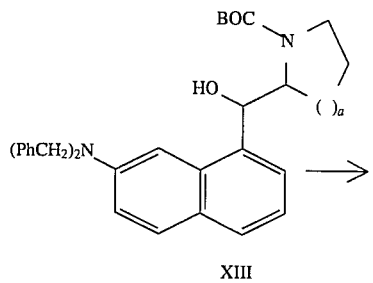

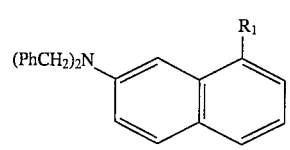

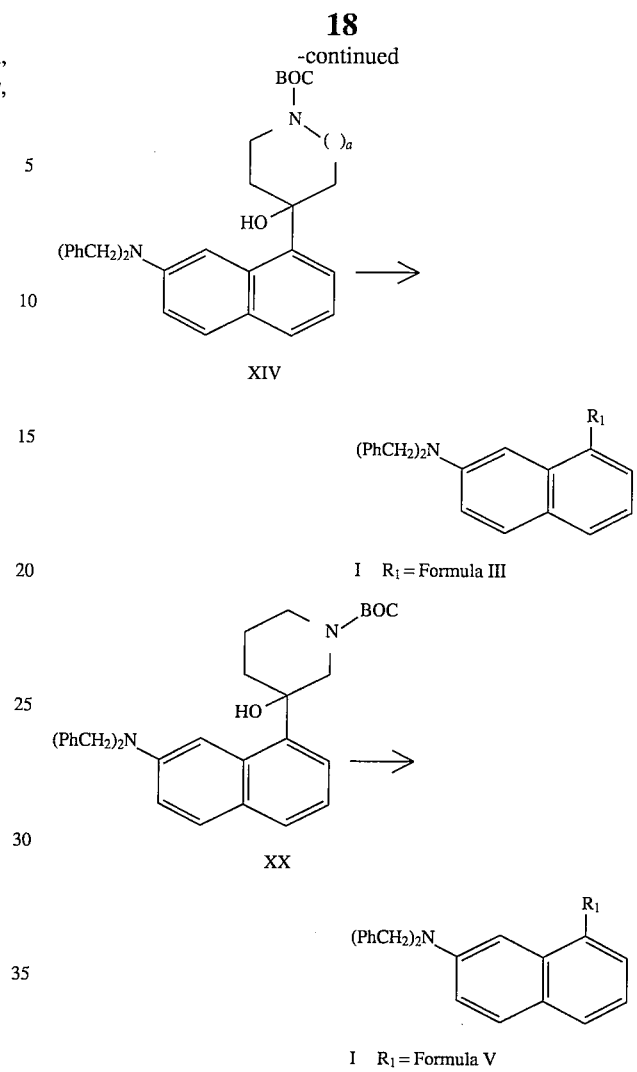

This step may be accomplished by one of several standard methods known in the art. For example, a thiocarbonyl derivative (for example a xanthate) may be prepared and removed by a free radical process, both of which are known to those skilled in the art. Alternatively, the hydroxyl group may be removed by reduction with a hydride source such as triethylsilane under acidic conditions, using such as, for example, trifluoroacetic acid or boron trifluoride. The reduction reaction can be performed neat or in a solvent, such as methylene chloride. A further alternative would be to first convert the hydroxyl group to a suitable leaving group, such as rosylate or chloride, using standard methods. The leaving group is then removed with a nucleophilic hydride, such as, for example, lithium aluminum hydride. This last reaction is performed typically in an inert solvent, such as ether or tetrahydrofuran. Also, a reducing agent may be used to reductively remove of the benzylic substituent. Suitable reducing agents include, for example, Raney nickel in ethanol, or sodium or lithium in liquid ammonia. Another alternative method for removing the hydroxyl group is to first dehydrate the alcohol XIII, XIV, or XX to an olefin with a reagent such as Burgess salt (*J. Org. Chem.*, 1973, 38, 26) followed by catalytic hydrogenation of the double bond under standard conditions with a catalyst such as palladium on carbon. The alcohol may also be dehydrated to the olefin by treatment with acid such as p-toluenesulfonic acid. For XIII the free radical procedure is preferred because it preserves the stereochemical integrity of the chiral center.

For XIV or XX the Burgess salt or acid dehydration procedures are preferred.

In the case where $R_2$ is, for example, dibenzylamino, additional compounds of formula I may be prepared by hydrogenolysis and derivatization as described above on pages 10 to 16.

8-bromo-β-tetralone, discussed earlier, may also be utilized to form other compounds of formula I, as shown below,

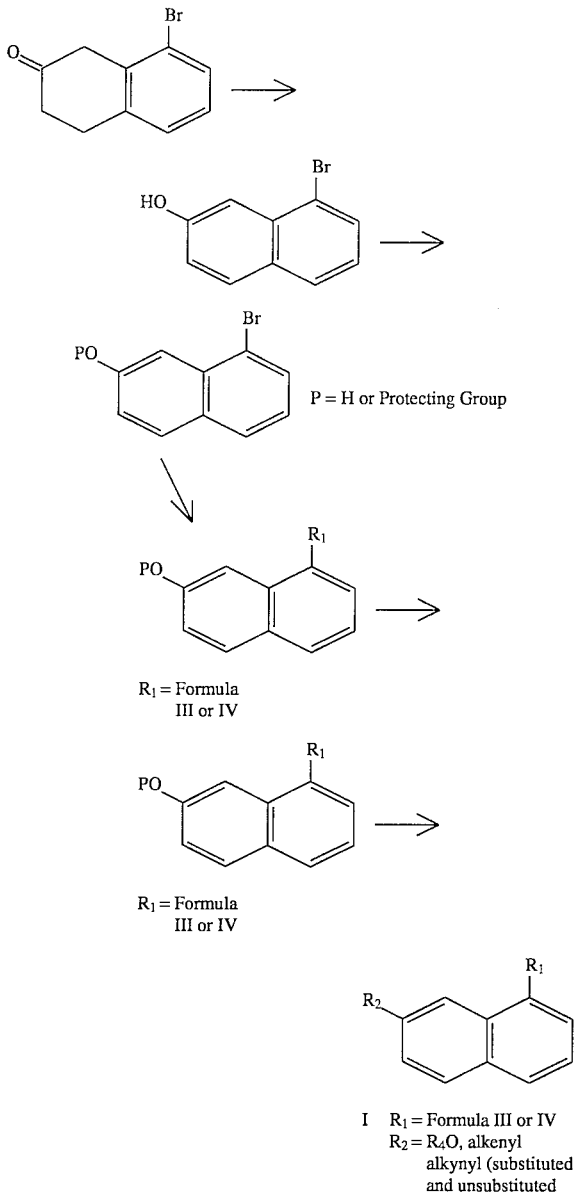

8-Bromo-β-tetralone is first dehydrogenated to form 1-bromo-7-hydroxynaphthalene using an oxidizing reagent, such as, for example, elemental sulfur as described above on page 8 or N-bromosuccinimide. An appropriate protecting group is then used to protect the hydroxyl group if desired, formation and selection being within the knowledge of one skilled in the art (e.g., Greene and Wuts, Protective Groups in Organic Synthesis, 2nd edition, Wiley, New York, 1991). This is followed by subsequent replacement of the bromo substituent using methods described previously on pages 16 to 18. After replacement of the bromo substituent, the hydroxyl protecting group may be removed using standard chemistry, and the free hydroxyl group may be derivatized as described above on pages 10 to 14 to afford compounds of formula I wherein $R_2$ is attached to the naphthalene ring via a carbon or oxygen atom. In some cases the protecting group may also serve as an activating group for further transformations, $CF_3SO_3$ for example, as described earlier on pages 12 to 14 or may simply be the final $R_2$ moiety.

Unless indicated otherwise, the pressure of each of the above reactions is not critical. Generally, the reactions will be conducted at a pressure of about one to about three atmospheres, preferably at ambient pressure (about one atmosphere).

U.S. Pat. No. 4,536,518 describes the synthesis, pharmaceutical composition and use of sertraline for depression and is hereby incorporated by reference in its entirety. Sertraline hydrochloride has the chemical formula $C_{17}H_{17}NCl_2$ and the following structural formula

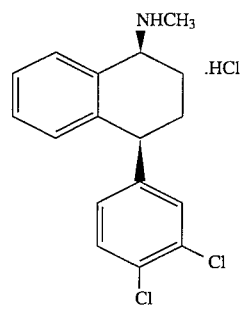

Its synthesis is described in U.S. Pat. No. 4,536,518, assigned to Pfizer Inc. Sertraline hydrochloride is useful as an antidepressant or an anorectic agent, and is also useful in the treatment of depression, chemical dependencies, anxiety-related disorders and premature ejaculation. U.S. Pat. No. 4,536,518 is hereby incorporated by reference in its entirety.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of formula I are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R_2$ contains a carboxylate, are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of the compounds of formula I are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of formula I may advantageously be used in conjunction with one or more other therapeutic agents, for instance, different antidepressant agents such as tricylic antidepressants (e.g., amitripyline, dothiepin, doxepin, trimipramine, butripyline, clomipramine, despramine, imipramine, iprindole, Iofepramine, nortriptyline or protriptyline), monoamine oxidase inhibitors (e.g., isocarboxazid, phenelzine or tranylcyclopramine) or 5-HT re-uptake inhibitors (e.g., fluvoxamine, sertraline, fluoxetine or paroxetine), and/or antiparkinsonian agents such as dopaminergic antiparkinsonian agents (e.g., levodopa, preferably in combination with a peripheral decarboxylase inhibitor e.g. benserazide or carbidopa, or a dopamine agonist e.g. bromocriptine, lysuride or pergolide). It is to be understood that the present invention covers the use of a compound of general formula (I) or a physiologically acceptable salt or solvate thereof in combination with one or more other therapeutic agents.

Preferably the compounds of the formula I and the pharmaceutically acceptable salts thereof in combination with a 5-HT re-uptake inhibitor (e.g., fluvoxamine, sertraline, fluoxetine or paroxetine), preferably sertraline, or pharmaceutically acceptable salts or polymorphs thereof (herein, the combination of a compound of formula I with a 5-HT re-uptake inhibitor is collectively referred to as "the active compounds") are useful psychotherapeutics and may be used in the treatment of a condition selected from mood disorders, including depression, seasonal affective disorders and dysthmia, anxiety disorders including generalized anxiety disorder and panic disorder; agoraphobia, avoidant personality disorder; social phobia; obsessive compulsive disorder; post-traumatic stress disorder; memory disorders including dementia, amnestic disorders and age-associated memory impairment; disorders of eating behavior, including anorexia nervosa and bulimia nervosa; obesity; cluster headache; migraine; pain; Alzheimer's disease; chronic paroxysmal hemicrania; headache associated with vascular disorders; Parkinson's disease, including dementia in Parkinson's disease, neuroleptic-induced parkinsonism and tardive dyskinesias; endocrine disorders such as hyperprolactinaemia; vasospasm (particularly in the cerebral vasculature); hypertension; disorders in the gastrointestinal tract where changes in motility and secretion are involved; sexual dysfunction, including premature ejaculation; and chemical dependencies. The compounds can also be used as centrally acting antihypertensives and vasodilators.

The affinities of the compounds of formula I for the various serotonin 1 receptors are evaluated using standard radioligand binding assays as described in the literature. The $5\text{-HT}_{1A}$ affinity is measured using the procedure of Hoyer et al. (Brain Res., 1986, 376, 85). The $5\text{-HT}_{1C}$ affinity is measured using the procedure of Pazos et al. (Eur. J. Pharmacol., 1985, 106, 539). The $5\text{-HT}_{1D}$ affinity is measured using the procedure of Heuring and Peroutka (J. Neurosci., 1987, 7, 894).

5-HT re-uptake inhibitors, preferably sertraline, exhibit positive activity against depression, chemical dependencies, anxiety disorders including panic disorder, generalized anxiety disorder, agoraphobia, simple phobias, social phobia, post-traumatic stress disorder, obsessive-compulsive disorder and avoidant personality disorder; premature ejaculation in mammals, including humans, due in part to their ability to block the synaptosomal uptake of serotonin.

Activity of the combination of the active compounds as antidepressants and related pharmacological properties are determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, (4) their ability to block the uptake of serotonin, norepinephrine and dopamine by synaptosomal rat brain cells in vitro by the method of Koe, B., *Journal of Pharmacology and Experimental Therapeutics*, 199 (3), pp. 649–661 (1976), and (5) their ability to counteract reserpine hypothermia in mice in vivo (see U.S. Pat. No. 4,029,731 ).

The compositions of the present invention may be formulated in a conventional manner using one or more pharmaceutically acceptable carriers. Thus, the active compounds may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds may be formulated for parenteral administration by injection, including using conventional catheterization techniques or infusion. Formulations for injection may be presented in unit dosage form, e.g. in ampules or in multi-dose containers, with an added preservative, The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds may also be formulated in rectal compositions such as suppositories or retention enemas, e.g., containing conventional suppository bases such as cocoa butter or other glycerides.

For intranasal administration or administration by inhalation, the active compounds are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of an active compound and a suitable powder base such as lactose or starch.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg. to about 100 mg. per kg. of body weight per day of a 5-HT re-uptake inhibitor, preferably sertraline, preferably from about 0.3 mg. to about 10 mg. per kg. of body weight per day of sertraline; with from about 0.01 mg. to about 100 mg. per kg. of body weight per day of a compound of formula I, preferably from about 0.1 mg. to about 3 mg. per kg. of body weight per day of a compound of formula I, although variations will necessarily occur depending upon the conditions of the subject being treated and the particular route of administration chosen.

In connection with the use of the compounds of formula I with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active compounds can be administered in a wide variety of different dosage forms, i.e., they may be combined with various pharmaceutically-acceptable inert carriers in the form of tablets, capsules, lozenges, troches, hand candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage. The compounds of this invention may exist in different polymorphic forms, i.e., different crystalline forms.

A proposed dose of the compounds of formula I in the combination formulation for oral, parenteral, rectal or buccal administration to the average adult human for the treatment of the conditions referred to above (e.g., migraine) is from about 0.01 mg. to about 2000 mg., preferably from about 0.1 mg. to about 200 mg of the active ingredient of formula I per unit dose which could be administered, for example, 1 to 4 times per day.

A proposed dose of a 5-HT re-uptake inhibitor, preferably sertraline, in the combination formulation for oral, parenteral or buccal administration to the average adult human for the treatment of the conditions referred to above (e.g., migraine) is from about 0.1 mg. to about 2000 mg., preferably from about 10 mg. to about 200 mg. of the 5-HT re-uptake inhibitor per unit dose which could be administered, for example, 1 to 4 times per day.

A preferred dose ratio of sertraline to a compound of formula I in the combination formulation for oral, parenteral or buccal administration to the average adult human for the treatment of the conditions referred to above (e.g., migraine) is from about 0.00005 to about 20,000, preferably from about 0.25 to about 2,000.

Aerosol combination formulations for treatment of the conditions referred to above (e.g., migraine) in the average adult human are preferably arranged so that each metered dose or "puff" of aerosol contains from about 0.01 mg to about 2000 mg of the compound of formula I, preferably from about 0.1 mg. to about 200 mg. of the compound of formula I. Administration may be several times daily, for example 2, 3, 4 or 8 times, giving for example, 1, 2 or 3 doses each time.

Aerosol formulations for treatment of the conditions referred to above (e.g., migraine) in the average adult human are preferably arranged so that each metered dose or "puff" of aerosol contains from about 0.01 mg. to about 2000 mg. of a 5-HT re-uptake inhibitor, preferably sertraline, preferably from about 10 mg. to about 200 mg of sertraline. Administration may be several times daily, for example 2, 3, 4 or 8 times, giving for example, 1, 2 or 3 doses each time.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to dimethylformamide. Chromatography refers to column chromatography performed using 32–63 µm silica gel and executed under nitrogen pressure (flash chromatography) conditions. Room or ambient temperature refers to 20°–25° C. All non-aqueous reactions were run under a nitrogen atmosphere for convenience and to maximize yields. Concentration at reduced pressure implies the use of a rotary evaporator.

The terms 1-piperazinyl and piperazin-1-yl, 1-piperidinyl and piperidin-1-yl, and 3-pyrrolidinyl and pyrrolidin-3-yl are used interchangeably throughout this document. Triflate refers to —$OSO_2CF_3$ or $CF_3SO_3$.

EXAMPLE 1

7-Benzamido-1-(4-methyl-1-piperazinyl)-naphthalene

7-Amino-α-tetralone (42.15 g, 0.262 mol) was dissolved in dry THF (1000 mL) and triethylamine (38.3 mL, 0.288 mol) was added. The mixture was chilled to 0° C. and benzoyl chloride (33.4 mL, 0.288 mol) was added dropwise with a THF (10 mL) rinse. The mixture was mechanically stirred overnight, then the solvent was removed with a nitrogen stream. The residues were taken up in methylene chloride and extracted with 1N HCl, water, saturated sodium bicarbonate, and brine. The organic phase was further dried over calcium sulfate and concentrated to a solid mass. Recrystallization from ethanol (650 mL) yielded 52 g of 7-benzamido-α-tetralone. Concentration of the mother liquors yielded another 6 g for a total yield of 58.9 g (85%): mp 153°–156° C. Analysis calculated for $C_{17}H_{14}NO_2$: C, 77.25; H, 5.34; N, 5.30. Found: C, 77.05; H, 5.57; N, 5.30.

7-Benzamido-α-tetralone (5.0 g, 18.95 mmol) was dissolved in dry THF (107 mL) and N-methyl-piperazine (6.3 mL, 56.8 mmol) was added. The solution was cooled to −78° C. and titanium tetrachloride (2.5 mL, 22.75 mmol) in methylene chloride (30 mL) was added dropwise. The mixture was stirred overnight and during this time a fine green precipitate formed. The solvent was removed under a stream of nitrogen and the residue was stirred vigorously in a mixture of ethyl acetate and 5N ammonium hydroxide for 2 hours. The solid which formed was collected, washed with ethyl acetate and then ether, and dried in vacuo. The filtrate was discarded. The solid was vigorously stirred with 1N sodium hydroxide (100 mL) and methylene chloride (100 mL) for 2 hours. The solid which did not dissolve was removed by filtration. The phases were separated from the filtrate and the organic layer was washed with brine, dried over calcium sulfate and concentrated to give 1.01 g of product. The solid was now stirred with dimethyl sulfoxide (DMSO, 150 mL) for 2 hours and filtered again. The undissolved material was discarded. The DMSO was removed at reduced pressure and the residue was taken up in methylene chloride. This organic solution was treated with brine which removed the last traces of DMSO from the organic phase and caused immediate precipitation of 2.29 g more product which was collected and dried. The phases were separated from the filtrate. The organic layer was dried over sodium sulfate and concentrated to leave 2.13 g of light tan solid product. In this fashion 5.43 g, 83% of 7-benzamido-1-(4-methyl-1-piperazinyl)-3,4-dihydronaphthalene was obtained; $^1$H NMR (CDCl$_3$) δ 7.88 (dd, J=1.5, 8 Hz, 2H), 7.77 (br s, 1H), 7.59 (d, J=2 Hz, 1H), 7.56–7.46 (m, 4H), 7.16 (d, J=8 Hz, 1H), 5.32 (t, J=4.5 Hz, 1H), 2.88 (br s, 4H), 2.69–2.55 (m, 6H), 2.36 (s, 3H), 2.27–2.17 (m, 2H).

A mixture of xylene (500 mL) and 10% Palladium on carbon (2.0 g) was refluxed overnight with azeotropic removal of water by means of a Dean-Stark trap containing 4 Å molecular sieves. The mixture was cooled to room temperature and 7-benzamido-1-(4-methyl-1-piperazinyl)-3,4-dihydronaphthalene (5.44 g, 15.67 mmol) was added. The mixture was heated at reflux for 2 hours, cooled, and filtered through a Celite pad. The filtrate was concentrated in vacuo and purified by silica gel flash chromatography (1.5×4 inches). Elution with 50 to 85% ethyl acetate/hexane gave 7-benzamido-α-tetralone (0.636 g). Continued elution with 95% ethyl acetate/hexane and pure ethyl acetate gave 1.37 g of title product followed by 1.95 g of a 2:1 mixture of title product and 7-benzamido-1-(4-methylpiperazinyl)-1,2,3,4-tetrahydronaphthalene. The 1.95 g mixture was rechromatographed as above to yield 1.0 g more pure title product. In this manner 2.37 g, 43% was obtained: mp 173°–175° C. Analysis calculated for $C_{22}H_{23}N_3O$; C 76.49; H, 6.71; N, 12.16. Found: C, 75.94; H, 6.39; N, 11.95.

EXAMPLE 2

7-Amino-1-(4-methyl-1-piperazinyl)-naphthalene

7-Benzamido-1-(4-methyl-1-piperazinyl)-naphthalene (the product from example 1, 3.75 g, 10.87 mmol) was slurried in 6N HCl (a mixture of concentrated HCl (25 mL) and ethanol (25 mL)) (50 mL) and refluxed for 3.5 hours. The mixture was cooled and brought to pH 10 with 1N sodium hydroxide. The aqueous mixture was extracted with methylene chloride. The organic layer was washed with brine, dried over calcium sulfate and concentrated to afford 2.44 g (92%) of the title product which was suitable for use in further reactions without purification. A sample was recrystallized from isopropyl alcohol for analysis: mp 157°–159° C.; $^1$H NMR δ 7.65 (d, J=8.5 Hz, 1H), 7.44 (d, J=8 Hz, 1H), 7.35 (d, J=2 Hz, 1H), 7.17 (t, J=8 Hz, 1H), 7.04 (d with long range coupling, J=7 Hz, 1H), 6.94 (dd, J=2.5, 8.5 Hz, 1H), 3.88 (br s, 3H), 3.12 (br s, 4H), 2.42 (s, 3H). Analysis calculated for $C_{15}H_{19}N_3$: C, 74.65; H, 7.94; N, 17.41. Found: C, 74.79; H, 8.14; N, 17.41.

EXAMPLE 3

7-(2-Naphthylcarboxamido)-1-(4-methyl-1-piperzinyl)-naphthalene

A solution of 7-amino-1-(4-methyl-1-piperazinyl)-naphthalene (0.197 g, 0.817 mmol) and triethylamine (0.217 mL, 1.63 mmol) in acetonitrile (10 mL) was chilled to 0° C. and 2-naphthoyl chloride (0.311 g, 1.63 mmol) was added. The solution was refluxed overnight. The solvent was removed at reduced pressure and the residue was taken up in methylene chloride. The mixture was stirred vigorously with saturated sodium bicarbonate for 2 hours and the phases were separated. The organic layer was dried over calcium sulfate and concentrated to a tan foam which was purified by flash chromatography on silica gel (1×3 inches). Ethyl acetate/hexane gradient elution of from 25:75 to 75:25 followed by ethyl acetate and finally 5% ethanol/ethyl acetate gave 0.31 g of light yellow foam. Trituration with hexane yielded 0.235 g (72%) of the title product as an amorphous solid: mp 95°–130° C. High resolution mass Spectrum (HRMS) m/e calculated for $C_{26}H_{25}N_3O$; 395.1994. Observed m/e: 395.1981.

EXAMPLE 4

7-(3-Nitrobenzamido)-1-(4-methyl-1-piperazinyl)-naphthalene

The title product was prepared following the procedure of example 3 from 7-amino-1-(4-methylol-piperazinyl)-naphthalene (0.15 g, 0.622 mmol) and triethylamine (0.09 mL, 0.68 mmol) and 3-nitrobenzoyl chloride (0.127 mL, 0.684 mmol) in acetonitrile (10 mL) with an overnight reflux. The product was purified by silica gel flash chromatography followed by recrystallization from ethyl acetate to yield 0.116 g (47%) of the title product: mp 182°–184° C. Analysis calculated for $C_{22}H_{22}N_4O_3$: C, 67.68; H, 5.68; N, 14.35. Found: C, 67.47; H, 5.64; N, 14.08.

EXAMPLE 5

7-(1-Naphthylcarboxamido)-1-(4-methyl-1-piperazinyl)-naphthalene

The title product was prepared following the procedure of example 3 from 7-amino-1-(4-methylol-piperazinyl)-naphthalene (0.227 g, 0.94 mmol) and triethylamine (0.133 mL, 0.1.32 mmol) and 1-naphthalenecarboxylic acid chloride (0.25 g, 1.32 mmol) in acetonitrile (10 mL) with stirring overnight at room temperature. The product was purified and after chromatography and recrystallization from ethyl acetate yielded 0.213 g (57%) of the title compound and had; mp 217°–218° C. Analysis calculated for $C_{26}H_{25}N_3O$: C, 78.96, H, 6.37; N, 10.62. Found: C, 78.66; H, 6.33; N, 10.48.

EXAMPLE 6

7-(3-Chlorobenzamido)-1-(4-methyl-1-piperazinyl)-naphthalene

The title product was prepared following the procedure of example 3 from 7-amino-1-(4-methyl-1-piperazinyl)-naphthalene (0.24 g, 0.995 mmol) and triethylamine (0.146 mL, 1.09 mmol) and 3-chlorobenzoyl chloride (0.138 mL, 1.09 mmol) in acetonitrile (10 mL) with overnight stirring at room temperature. The product was isolated using flash chromatography and trituration from hexane and recrystallization from ethyl acetate (with a seed crystal) to yield 0.076g (20%) of the title compound: mp 147°–148° C. HRMS m/e calculated for $C_{22}H_{22}ClN_3O$; 379.1448. Observed m/e: 379.14473. Analysis calculated for $C_{22}H_{22}ClN_3O$: C, 69.56; H, 5.84; N, 11.06. Found: C, 68.95; H, 5.81; N, 10.96.

EXAMPLE 7

7-(3,5-Dinitrobenzamido)-1-(4-methyl-1-piperazinyl)-naphthalene

The title product was prepared following the procedure of example 3 from 7-amino-1-(4-methyl-1-piperazinyl)-naphthalene (0.15 g, 0.622 mmol) and triethylamine (0.09 mL, 0.68 mmol) and 3,5-dinitrobenzoyl chloride (0.158 g, 0.684 mmol) in acetonitrile (10 mL) with overnight stirring at room temperature. The product was purified using chromatography and recrystallization from acetonitrile to yield 0.17 g (63%) of the title compound: mp 254°–256° C. Analysis calculated for $C_{22}H21N_5O_5$: C, 60.68; H, 4.86; N, 16.08. Found: C, 60.59; H, 4.73; N, 15.88.

EXAMPLE 8

7-(4-Chlorobenzamido)-1-(4-methyl-1-piperazinyl)-naphthalene

The title product was prepared following the procedure of example 3 from 7-amino-1-(4-methyl-1-piperazinyl)-naphthalene (0.249 g, 1.03 mmol) and triethylamine (0.151 mL, 1.14 mmol) and 4-chlorobenzoyl chloride (0.241 g, 1.14 mmol) in acetonitrile (10 mL) with overnight stirring at room temperature. The product was purified using chromatography and recrystallization from ethyl acetate to yield 0.17 g (43%) of the title compound as a white solid mp 174°–175° C. HRMS m/e calculated for $C_{22}H_{22}ClN_3O$: 379.1448. Observed m/e: 379.1465. Analysis calculated for $C_{22}H_{22}ClN_3O$: C, 69.56; H, 5.84; N, 11.06. Found: C, 69.38; H, 5.80; N, 10.96.

EXAMPLE 9

7-(3-Cyanobenzamido) -1-(4-methyl-1-piperazinyl)-naphthalene

The title product was prepared following the procedure of example 3 from 7-amino-1-(4-methyl-1-piperazinyl)-naphthalene (0.213 g, 0.883 mmol) and triethylamine (0.258 mL, 1.94 mmol) and 3-cyanobenzoyl chloride (0.322 g, 1.94 mmol) in acetonitrile (10 mL) with stirring at reflux for 2 hours and then at room temperature overnight. The mixture was concentrated and the residue was taken up in methylene chloride. This organic solution was washed with 0.5N sodium hydroxide, dried over calcium sulfate and concentrated. The product was isolated by silica gel flash chromatography and recrystallization from isopropyl alcohol to yield 0.184 g of (60%) of the title compound: mp 220°–222° C. Analysis calculated for $C_{23}H_{22}N_4O$: C, 74.57; H, 5.99; N, 15.12. Found: C, 74.42; H, 5.78; N, 14.96.

EXAMPLE 10

7-(4-Hydroxybenzamido)-1-(4-methyl-1-piperazinyl)-naphthalene

A mixture of 7-amino-1-(4-methyl-1-piperazinyl)-naphthalene (0.118 g, 0.489 mmol) and triethylamine (0.13 mL, 0.98 mmol) in acetonitrile (10 mL) was chilled to 0° C. and 4-triisopropylsilyloxybenzoyl chloride (0.16 g, 0.51 mmol) dissolved in methylene chloride was added all at once. The mixture was gently refluxed overnight; then 7-amino-1-(4-methyl-1-piperazinyl)-naphthalene (0.038 g, 0.16 mmol), 4-triisopropylsilyloxybenzoyl chloride (0.5 g, 1.6 mmol), and triethylamine (0.13 mL, 0.93 mmol) were added. The reaction was refluxed for an additional 24 hours, cooled and the solvent was removed at reduced pressure. The residue was partitioned between methylene chloride and saturated aqueous sodium bicarbonate and stirred vigorously for 5 hours. The phases were separated and the organic layer was washed with brine, dried over calcium sulfate and concentrated to a tan foam which was purified by flash chromatography on silica gel (1×3.5 inches). Elution with 25% ethyl acetate/hexane removed unweighed recovered acid chloride. Continued elution with an ethyl acetate/hexane gradient of from 1:3 to 3:1 followed by 100% ethyl acetate gave 0.238 g of 7-(4-triisopropylsilyloxybenzamido)-1-(4-methyl-1-piperazinyl)-naphthalene as a viscous tan oil.

The product of the above reaction was dissolved in dry THF (10 mL) and tetrabutylammonium fluoride (0.47 mL, 0.47 mmol, 1M in THF solution) was added dropwise. The solution darkened and was stirred 2 hours followed by addition of 0.2 mL more tetrabutylammonium fluoride. After stirring an additional 3 hours, the solvent was removed and the residue was taken up in ethyl acetate. This organic phase was washed with water and brine, dried over calcium sulfate and concentrated to a white foam. This foam was flash chromatographed on silica gel (1×4 inches). Gradient elution with ethyl acetate/hexane of from 1:3 to 3:1 gave nil. Continued elution with 5% ethanol/ethyl acetate gave first the title product (0.04 g) which was about 80% pure followed by an additional 0.02 g of pure product. The 0.02 g sample was triturated with ether/hexane and yielded 0.006 g (1.9%) of title product as a tan solid: mp 156°–160° C. HRMS m/e calculated for $C_{22}H_{23}N_3O_2$: 361.1789. Observed m/e: 361.1787.

EXAMPLE 11

7-Benzamido-1-(1-piperazinyl)-naphthalene

The title product from Example 1 (0.50 g, 1.45 mmol) was dissolved in methylene chloride (10 mL) and chilled to 0° C. 1-chloroethyl chloroformate (0.156 mL, 1.45 mmol) was added via syringe. The mixture was allowed to come to room temperature and then refluxed 3 hours. Additional 1-chloroethyl chloroformate (0.1 mL, 0.93 mmol) was added and the mixture was further refluxed overnight. Methanol (10mL) was added and the reaction was refluxed for 2 hours. The mixture was concentrated and the residue was taken up in methylene chloride and extracted with 1N NaOH and brine. The organic phase was dried, concentrated onto silica gel, and flash chromatographed (1×4 inches silica gel). Gradient elution with ethyl acetate/hexane of from 1: 1 to 100% ethyl acetate followed by elution with 2 to 10% ethanol/0.1% ammonium hydroxide/ethyl acetate gave recovered unweighed starting material. Continued elution with 15% methanol/0.1% ammonium hydroxide/ethyl acetate gave 0.32 g of the title product as a clear colorless oil which partially crystallized on standing. Trituration with ether gave 0.13 g (27%) of the title compound as white crystals: mp 141.5°–144° C.; $^1$H NMR δ 8.58 (br s, 1H), 8.04 (br s, 1H), 7.95 (dd, J=8, 1.5 Hz, 2H), 7.84 (d, J=9 Hz, 1H), 7.68 (dd, J=2, 9 Hz, 1H), 7.62–7.49 (m, 4H), 7.37 (t, J=8 Hz, 1H), 7.12 (d, J=7 Hz, 1H), 3.32–3.22 (m, 5H), 3.16 (br s, 3H), 2.40 (br s, 1H, exchanges with D$_2$O). HRMS m/e calculated for C$_{21}$H$_{21}$N$_3$O: 331.1680. Observed m/e: 331.1682.

EXAMPLE 12

7-(4-Chlorobenzamido-1-(1-piperazinyl)-naphthalene

The title product of example 8 (1.69 g, 4.62 mmol) and 1,8-bis (dimethylamino)naphthalene (3.47 g, 16.2 mmol) were dissolved in dichloroethane (160 mL) and chilled to 0° C. 1-Chloroethyl chloroformate (0.8 mL, 7.4 mmol) was added and the solution was refluxed overnight. The mixture was concentrated and flash chromatographed on silica gel (2×3 inches). Elution with 10 to 25% ethyl acetate/hexane gave first an unweighed impurities and then 1.56 g of a mixture of 1,8-bis (dimethylamino)naphthalene and the urethane intermediate (1:1.2 ratio). The mixture was dissolved in methylene chloride and extracted repeatedly with pH 5.8 buffer. The organic layer was dried over calcium sulfate and concentrated to give 0.98g of base free intermediate urethane suitable for subsequent reaction.

The intermediate was dissolved in methanol (40 mL) and refluxed 5 hours. The mixture was concentrated and the residues were taken up in methylene chloride. The organic phase was washed with 0.5N NaOH and brine, dried over calcium sulfate and concentrated. The residue was flash chromatographed on silica gel (1×2 inches). Elution with 5 to 15% methanol/0.1% ammonium hydroxide/ethyl acetate gave 0.667 g of oily solid. This semi-solid recrystallized from methanol to give 0.54 g (32%) of the title compound as tan crystals in two crops: mp 210°–211 ° C. HRMS m/e calculated for C$_{21}$H$_{20}$ClN$_3$O: 365.1290. Observed m/e: 365.1294.

EXAMPLE 13

7-(1-Naphthylmethylamino)-1-(4-methyl-1-piperazinyl)-naphthalene

To a cold (−78° C.) mixture of lithium aluminum hydride (0.012 g, 0.316 mmol) in THF (5 mL) was added the product of example 5 (0.10 g, 0.256 mmol) all at once. The mixture was allowed to warm to ambient temperature and stir 5 hours. The mixture was refluxed overnight. The mixture was cooled to 0° C. and additional lithium aluminum hydride (0.014 g, 0.368 mmol) was added and the mixture was refluxed 5 hours more. The mixture was again cooled to 0° C. and carefully quenched with water and the solvent was removed. The residue was taken up in ethyl acetate, dried over sodium sulfate, concentrated, and flash chromatographed on silica gel (1×2.5 inches). Elution with a gradient of 50 to 85% ethyl acetate/hexane gave 0.05 g of title product. Recrystallization from ether gave 0.018 g (18.5%) of title product as a white solid: mp 140°–141 ° C. HRMS m/e calculated for C$_{26}$H$_{27}$N$_3$: 381.2199. Observed m/e: 381.2217.

EXAMPLE 14

7-(Benzylamino)-1-(4-methyl-1-piperazinyl)-naphthalene

The title product of example 1 (0.12 g, 0.348 mmol) was dissolved in toluene (4 mL) and borane-dimethyl sulfide (0.3 mL, 3 mmol) was added. The mixture was refluxed 3 hours and cooled. 6N HCl and ethyl acetate were added and the mixture was refluxed until all the solids had dissolved. The organic phase was separated and discarded. The aqueous phase was made basic with 4N NaOH and extracted with methylene chloride. This organic phase was washed with brine, dried over calcium sulfate and concentrated. The crude product was purified by flash chromatography on silica gel (0.5×4 inches). Elution with 50% and then 75% ethyl acetate/hexane gave 0.053 g of product. This material was further purified by trituration with hexane to provide 0.03 g, (26%) of the title product as a tan powder: mp 115°–117° C.; $^1$H NMR δ 7.64 (d, J=8.5 Hz, 1H), 7.46–7.24 (m, 6H), 7.14 (t, J=7.5 Hz, 1H), 7.0 (d, J=2.5 Hz, 1H), 7.00 (ss, J=1, 7.5 Hz, 1H), 6.94 (dd, J=2.5, 8.5 Hz, 1H), 4.50 (br s, 2H), 4.34 (br m, 1H), 3.01 (br s, 4H), 2.53 (br s, 4H), 2.38 (s, 3H). Analysis calculated for C$_{22}$H$_{25}$N$_3$·0.5 H$_2$O: C, 77.61; H, 7.70; N, 12.34. Found: C, 77.78; H, 7.48; N, 12.07.

EXAMPLE 15

7-Trifluoroacetamido-1-(4-methyl-1-piperazinyl)-naphthalene

A solution of 7-amino-1-(4-methyl-1-piperazinyl)-naphthalene (0.25 g, 1.04 mmol) and triethylamine (0.15 mL, 1.14 mmol) in dry THF was chilled to 0° C. and treated with trifluoroacetic anhydride (0.16 mL, 1.14 mmol). The mixture was allowed to warm to ambient temperature and stir overnight. Triethylamine (0.25 mL, 1.88 mmol) and trifluoroacetic anhydride (0.16 mL, 1.14 mmol) were added and the solution was stirred another 24 hours. Triethylamine (0.15 mL, 1.14 mmol) was added and the solution was stirred 2 hours more. The solvent was removed at reduced pressure and the residue was taken up in methylene chloride. The organic solution was washed with saturated sodium bicarbonate and brine, then it was dried over calcium sulfate and concentrated. The product was purified by silica gel flash chromatography (1×2 inches). Ethyl acetate/hexane gradient elution of from 1:1 to 3:1 gave 0.15 g of oily product. Trituration with hexane gave 0.11 g (31%) of the title product. A sample recrystallized from methyl cyclohexane was submitted for analysis: mp 159°–160° C. HRMS m/e calculated for C$_{17}$H$_{18}$F$_3$N$_3$O: 337.1400. Observed m/e: 337.13867. Analysis calculated for C$_{17}$H$_{18}$F$_3$N$_3$O: C, 60.53; H, 5.38; N, 12.46. Found: C, 60.04; H, 5.27; N, 12.05.

EXAMPLE 16

7-Acetamido-1-(4-methyl-1-piperazinyl)-naphthalene

A solution of 7-amino-1-(4-methyl-1-piperazinyl)-naphthalene (0.238 g, 0.986 mmol) and triethylamine (0.144 mL, 1.08 mmol) in acetonitrile (12 mL) was chilled to 0° C. and acetyl chloride (0.077 mL, 1.08 mmol) was added all at once. The mixture was heated to reflux for 7 hours and cooled to room temperature. (TLC with 40% methanol/ethyl acetate indicated that the reaction was complete.) The solvent was removed at reduced pressure and the residue was taken up in methylene chloride. The organic solution was extracted with saturated sodium bicarbonate and brine, then it was dried over calcium sulfate and concentrated to a light tan solid (0.115 g). Trituration with hexane gave 0.09 g (33%) of the title product as a tan solid: mp 173°–177° C. A sample recrystallized from ethyl acetate was submitted for analysis: mp 177°–180° C. HRMS m/e calculated for C$_{17}$H$_{29}$N$_3$O: 283.1682. Observed m/e: 283.1678.

EXAMPLE 17

7-Hexanamido-1-(4-methyl-1-piperazinyl)-naphthalene

The title product was prepared following the procedure of example 16 from 7-amino-1-(4-methyl-1-piperazinyl)-naphthalene (0.182 g, 0.755 mmol) and triethylamine (0.201 mL, 1.51 mmol) and hexanoyl chloride (0.211 mL, 1.51 mmol) in acetonitrile (10 mL) with an overnight reflux. The product was purified by recrystallization from ethyl acetate/hexane to yield 0.097g (37%) of the title compound: mp 144°–146° C. Analysis calculated for $C_{21}H_{29}N_3O$: C, 74.30; H, 8.61; N, 12.38. Found: C, 73.91; H, 8.52; N, 12.22.

EXAMPLE 18

7-(p-Toluenesulfonamido)-1-(4-methyl-1-piperazinyl)-naphthalene

A solution of 7-amino-1-(4-methyl-1-piperazinyl)-naphthalene (0.205 g, 0.85 mmol) and triethylamine (0.124 mL, 0.935 mmol) in dry THF (3 mL) was chilled to 0° C and para toluenesulfonyl chloride (0.178 g, 0.935 mmol) was added all at once. The mixture was allowed to warm to room temperature and stirred overnight (TLC with 40% methanol/ethyl acetate indicated that the reaction was complete.) The solvent was removed at reduced pressure and the residue was taken up in methylene chloride. The organic solution was extracted with saturated sodium bicarbonate and brine, then it was dried over calcium sulfate and concentrated. Flash chromatography on silica gel (1×3 inches) with ethyl acetate/hexane gradient elution of from 50% to 100% gave 0.21 g of a light tan solid. The solid was further purified by two recrystallizations from ethyl acetate to yield 0.07 g (20%) of the title product: mp 180°–1 81.5° C. Analysis calculated for $C_{22}H_{25}N_3O_2S$: C, 66.81; H, 6.37; N, 10.62. Found: C, 66.55; H, 6.31; N, 10.20.

EXAMPLE 19

7-(Phenylaminocarbonylamino)-1-(4-methyl-1-piperazinyl)-naphthalene

7-Amino-1-(4-methyl-1-piperazinyl)-naphthalene (0.216 g, 0.896 mmol) and phenyl isocyanate (0.222 g, 1.86 mmol) were combined in acetonitrile (14 mL) and refluxed overnight. Phenyl isocyanate (0.106 g, 0.896 mmol) was added and the reaction was refluxed 2 hours more. Upon cooling a tan solid precipitated which was collected and recrystallized from methanol/ethyl acetate to give 0.202 g (62%) of the title product; mp 213°–214° C. Analysis calculated for $C_{22}H_{24}N_4O$: C, 73.31; H, 6.71; N, 15.54. Found: C0 73.03; H, 6.55; N, 15.22.

EXAMPLE 20

7-(Benzyloxycarbonylamino)-1-(4-methyl-1-piperazinyl)-naphthalene

7-Amino-1-(4-methyl-1-piperazinyl)-naphthalene (0.225 g, 0.933 mmol), benzyl chloroformate (0.147 mL, 1.03 mmol), and potassium carbonate (0.142 g, 1.03 mmol) were combined in a two phase mixture of methylene chloride (10 mL) and water (3 mL) and the mixture was stirred at room temperature overnight. Benzyl chloroformate (0.147 mL, 1.03 mmol) was added and the reaction was stirred 5 hours more. The reaction was diluted with methylene chloride and the phases were separated. The organic layer was washed with brine, dried over calcium sulfate and concentrated to a brown oil which was flash chromatographed on silica gel (1×4 inches). Gradient elution with ethyl acetate/hexane of from 50% to 100% followed by gradient ethanol/ethyl acetate elution of from 5% to 10% gave 0.29 g of a brown foam. This residue was recrystallized from ethyl acetate to give 0.095 g (27%) of the title product in two crops; mp 143°–144° C. Analysis calculated for $C_{23}H_{25}N_3O_2$: C, 73.58; H, 6.71; N, 11.19. Found: C, 73.46; H, 6.71; N, 11.05.

EXAMPLE 21

7-[(2-Benzyloxycarbonylamino)-acetamido]-1-(4-methyl-1-piperazinyl)naphthalene

N-benzyloxycarbonylglycine (0.69 g, 3.32 mmol) was dissolved in methylene chloride (10 mL) and carbonyl diimidazole (0.54 g, 3.32 mmol) was added. The solution was stirred for 2 hours; then 7-amino-1-(4-methyl-1-piperizinyl)-naphthalene (0.2 g, 0.83 mmol) was added. The solution was stirred overnight. The reaction was extracted with saturated aqueous potassium carbonate and brine, dried over calcium sulfate and concentrated to give white crystals. Recrystallization from ethyl acetate gave 0.187 g (52%) of the title product as white crystals: mp 187°–188° C. Analysis calculated for $C_{25}H_{28}N_4O_3$: C, 69.42; H, 6.52; N, 12.95. Found: C, 69.21; H, 6.50; N, 12.79.

EXAMPLE 22

7-(Benzoylaminothiocarbonylamino)-1-(4-methyl-1-piperazinyl)-naphthalene

To a mixture of ammonium thiocyanate (0.376 g, 4.94 mmol) in acetone (5 mL) was added benzoyl chloride (0.57 mL, 4.94 mmol) dropwise. The mixture (white precipitate) was refluxed 45 minutes which resulted in a yellow heterogeneous solution. A solution of 7-Amino-1-(4-methyl-1-piperazinyl)-naphthalene (1.0 g, 4.14 mmol) in acetone (25 mL) was added dropwise (10 mL acetone rinse also added). The mixture was refluxed 4 hours and allowed to stir overnight at ambient temperature. The mixture was concentrated onto silica gel and flash chromatographed (2×3.5 inches). Gradient elution with ethyl acetate/hexane of from 50% to 100% gave an unweighed forerun. Continued gradient elution with 10 to 40% ethanol/ethyl acetate gave 1.3 g (77%) of title product as a yellow foam which was suitable for use without further purification. The compound was found to slowly decompose at room temperature. A sample recrystallized from ethyl acetate/methylene chloride for analysis: mp 160°–250° C. $^1$H NMR (DMSO$_{d6}$, $D_2O$) δ 8.74 (s, 1H), 7.97 (d, J=7.5 Hz, 1H), 7.91 (d, J=9 Hz, 1H), 7.70–7.51 (m, 5H), 7.42 (t, J=8 Hz, 1H), 7.12 (d, J=7 Hz, 1H), 3.11 (m, 4 H), 2.79 (br s, 4H), 2.39 (s, 3H). HRMS m/e calculated for $C_{23}H_{24}N_4OS$: 404.1661. Observed m/e: 404.1633.

EXAMPLE 23

7-(Aminothiocarbonylamino)-1-(4-methyl-1-piperazinyl)-naphthalene

The title product of example 22 (1.09 g, 2.7 mmol) was slurried in ethanol (10 mL) and a solution of 1.4 g NaOH in water (14 mL) was added. The mixture was refluxed 3 hours; then the ethanol was removed with a stream of nitrogen. The aqueous residue was extracted with methylene chloride. The organic phase was washed with brine, dried over calcium sulfate, and concentrated to leave 0.39 g (48%) of the title product. A sample was recrystallized from acetonitrile for analysis: mp 194°– 195° C. Analysis calculated for $C_{16}H_{20}N_4S \cdot CH_3CN \cdot 0.5\ H_2O$; C, 62.96; H, 6.67; N, 19.32. Found: C, 62.86; H, 6.71; N, 19.69.

EXAMPLE 24

4-Benzyl-2-[-1-(4-methyl-1-piperazinyl)-7-naphthylamino]-thiazole

A mixture of the title product of example 23 (0.225 g, 0.75 mmol) and 1-chloro-3-phenylacetone (0.188 g, 1.12 mmol) in isopropanol (6 mL) was refluxed 3 hours. The solvent was removed and the residue was taken up in methylene chloride. The organic phase was washed with saturated aqueous sodium bicarbonate and brine, dried over calcium sulfate, and concentrated onto silica gel for flash chromatography (1×3 inches). Gradient elution with 50% to 100% ethyl acetate/hexane gave an unweighed forerun. Continued elution with ethyl acetate gave 0.283 g of a yellow foam. Trituration with ethyl acetate gave 0.137 g (44%) of the title product as yellow crystals: mp 157°–160° C. Analysis calculated for $C_{25}H_{26}N_4S$: C, 72.43; H, 6.32; N, 13.51. Found: C, 72.55; H, 6.51; N, 13.72.

EXAMPLE 25

7-(3-Nitro-2-pyridinylamino)-1-(4-methyl-piperazinyl)-naphthalene

7-Amino-1-(4-methyl-1-piperazinyl)-naphthalene (0.247 g, 1.02 mmol), 2-chloro-3-nitropyridine (0.325 g, 2.05 mmol), and 4-dimethylaminopyridine (0.062 g, 0.51 mmol) were combined in dry DMF (0.15 mL). The solution was refluxed 4 hours then 0.5 mL more DMF was added and the mixture was allowed to stir at ambient temperature overnight. 2-Chloro-3-nitropyridine (0.105 g, 0.69 mmol), and 4-dimethylaminopyridine (0.062 g, 0.51 mmol) were added and the mixture was refluxed 2 hours more. The solvent was removed in vacuo and the residue was taken up in methylene chloride. This organic phase was washed with 0.5N sodium hydroxide and brine; then it was dried over calcium sulfate and concentrated to a red oil which was flash chromatographed on silica gel (1×4 inches). Gradient elution with 50% to 75% ethyl acetate/hexane followed by elution with 100% ethyl acetate gave a dark colored oil which crystallized upon addition of ether (2 mL) to yield 0.19 g (51%) as a dark red solid: mp 127.5°–129° C. Analysis calculated for $C_{20}H_{21}N_5O_2$; C, 66.10; H, 5.82; N, 19.27. Found: C, 66.04; H, 5.81; N, 19.02.

EXAMPLE 26

7-(2,4-Dinitrophenylamino)-1-(4-methyl-1-piperazinyl)-naphthalene

A mixture of 7-amino-1-(4-methyl-1-piperazinyl)-naphthalene (0.05 g, 0.207 mmol) and 2,4-dinitrochlorobenzene (0.75 g, 0.373 mmol) in dry DMF (2 mL) was refluxed 2 hours. The solvent was removed in vacuo and the residue was taken up in methylene chloride. The organic phase was washed with saturated sodium bicarbonate and brine, dried over calcium sulfate and concentrated. The residue was recrystallized from ether to give 0.045g (54%) of the title compound: mp 153°–154° C. Analysis calculated for $C_{21}H_{21}N_5O_4$; C, 61.91; H, 5.20; N, 17.19. Found: C, 61.42; H, 5.10; N, 16.79.

EXAMPLE 27

7-(5-Nitro-2-pyridylamino)-1-(4-methyl-1-piperazinyl)-naphthalene

A mixture of 7-amino-1-(4-methyl-1-piperazinyl)-naphthalene (0.212 g, 0.88 mmol), 5-nitro-2-chloropyridine (0.314 g, 1.98 mmol), and 4-dimethylaminopyridine (0.085 g, 0.7 mmol) in dry DMF (2 mL) was refluxed 8 hours. The solvent was removed in vacuo and the residue was taken up in methylene chloride. The organic phase was washed with saturated 0.5N NaOH and brine, dried over calcium sulfate and concentrated. The residue was flash chromatographed on silica gel (1×4 inches). Gradient elution with from 50% to 90% ethyl acetate/hexane gave an unweighed forerun. Continued elution with ethyl acetate gave 0.136 g of orange oil. Recrystallization from isopropanol followed by recrystallization from nitromethane gave 0.005 g (1.4%) of the title product as orange crystals: mp 121°–125° C. Analysis calculated for $C_{20}H_{21}N_5O_2 \cdot H_2O$; C, 62.98; H, 6.08; N, 18.36. Found: C, 62.86; H, 5.84; N, 18.13.

EXAMPLE 28

7-(2-Nitrophenylamino)-1-(4-methyl-1-piperazinyl)-naphthalene

The title product was obtained following the procedure of example 27 by reacting 7-amino-1-(4-methyl-1-piperazinyl)-naphthalene (0.225 g, 0.93 mmol), 2-fluoronitrobenzene (0.255 g, 1.8 mmol), and 4-dimethylaminopyridine (0.167 g, 1.37 mmol) in dry DMF (5 mL) with an overnight reflux. The product was isolated by silica gel flash chromatography and recrystallization from ethyl acetate/ether to yield 0.024 g (7%) of the title compound as orange crystals: mp 87°–94° C.; $^1$H NMR δ 9.70 (br s, 1H), 8.26 (dd, J=1.5, 8.5 Hz, 1H), 8.07 (d, J=2 Hz, 1H), 7.87 (d, J=8.5 Hz, 1H), 7.57 (s, J=8 Hz, 1H), 7.44–7.32 9m, 4H), 7.16 (dd, J=1,7.5 Hz, 1H), 6.82 (dd, J=6.5, 8.5 Hz, 1H), 3.15 (br s, 4H), 2.70 (br s, 4H), 2.41 (s, 3H). HRMS m/e calculated for $C_{21}H_{22}N_4O_2$; 362.1738. Observed m/e: 362.1736.

EXAMPLE 29

7-(3-Amino-2-pyridylamino)-1-(4-methyl-1-piperazinyl)-naphthalene

To a slurry of 10% palladium on carbon (0.56 g) in ethanol (30 mL) was added the title product from example 25 (3.38 g, 9.3 mmol) was dissolved in a mixture of ethanol (20 mL), methanol (50 mL), and ethyl acetate (100 mL). The mixture was hydrogenated at 50 psi for 3 hours. A total of 36 psi of $H_2$ was taken up (35 psi is theory). The mixture was filtered through celite and the filter pad was rinsed well with ethyl acetate. The filtrate was concentrated to give 3.4 g (100%) of brown crystals which was an ethanolate of the title product which was suitable for further reaction without purification. A sample recrystallized from ethanol for analysis: mp 198°–200° C. Analysis calculated for $C_{20}H_{23}N_5$: C, 72.04; H, 6.95; N, 21.00. Found: C, 71.72; H, 6.87; N, 20.84.

EXAMPLE 30

7-(3-Benzamido-2-pyridylamio)-1-(4-methyl-1-piperazinyl)-naphthalene

The title product from example 29 (0.2 g, 0.6 mmol) and triethylamine (0.15 mL, 1.1 mmol) were dissolved in THF (8 mL) and the solution was chilled to 0° C. Benzoyl chloride (0.09 mL, 0.78 mmol) was added and the mixture was stirred 24 hours at room temperature. The solvent was removed and the residue was taken up in methylene chloride. The organic phase was washed with 1N NaOH and brine; then it was dried through phase separating paper and concentrated onto silica gel for flash chromatography (1×3.5 inches). Elution with methylene chloride then 3% methanol/methylene chloride was not productive. Continued elution with 6% methanol/methylene chloride gave first 0.108 g of an impurity and second 0.128 g of product as a tan foam. The foam was further purified by recrystallization from ethyl acetate to yield 0.078 g (30%) of the title product as tan crystals: mp 205°–207° C. Analysis calculated for $C_{27}H_{27}N_5O$; C; 74.12; H, 6.22; N, 16.01. Found: C, 73.59; H, 5.93; N, 15.54.

EXAMPLE 31

7-(3-Acetamido-2-pyridylamino)-1-(4-methyl-1-piperazinyl)-naphthalene

The title compound was prepared following the procedure of example 30 from the product of example 29 (0.25 g, 0.75 mmol), acetyl chloride (0.045 mL, 0.80 mmol) and triethylamine (0.11 mL, 0.803 mmol) in tetrahydrofuran (8 mL) with stirring at room temperature for 3 hours. The product was isolated by flash chromatography and recrystallization from methylene chloride to yield 0.18g (64%) of the title compound: mp 110°–114° C. (dec.). $^1$H NMR (DMSO$_{d6}$) δ 9.47 (s, 1H), 8.65 (d, J=1.5 Hz, 1H), 8.35(s, 1H), 8.03 (dd, J=1.5, 5 Hz, 1H), 7.77–7.70 (m, 2H), 7.53 (dd, J=2, 9 Hz, 1H), 7.46 (d, J=8 Hz, 1H), 7.22 (t, J=8 Hz, 1H), 7.00 (d, J=7.5 Hz, 1H), 6.88 (dd, J=5, 8 Hz, 1H), 3.07 (br s, 4H), 2.63 (br s, 4H), 2.29 (s, 3H), 2.14 (s, 3H). HRMS m/e calculated for $C_{22}H_{25}N_5O$: 375.2054. Observed m/e: 375.2023.

EXAMPLE 32

1-(4-Methyl-1-piperazinyl)-7-(1-pyridotriazolo)-naphthalene

The title product from example 29 (0.21 9 g, 0.657 mmol) was dissolved in 5% sulfuric acid (1.5 mL) and chilled to 0° C. Sodium nitrite (0.048 g, 0.69 mmol) was dissolved in water (0.25 mL) and added dropwise with a water rinse (2×0.25 mL). The mixture was allowed to stir overnight. The reaction was poured onto ice and neutralized with 1N NaOH. The aqueous mixture was extracted 3 times with methylene chloride and the combined organic layer was washed with saturated sodium bicarbonate and brine. The organic phase was dried through phase separating paper and concentrated to a brown foam. The foam was recrystallized from methanol to afford 0.124 g (55%) of the title product as tan crystals: mp 162°–164° C. $^1$H NMR δ 9.28 (d, J=2 Hz, 1H), 8.82 (dd, J=1.5, 4.5 Hz, 1H), 8.52 (dd, J=1.5, 8.5 Hz, 1H), 8.39 (dd, J=2, 9 Hz, 1H), 8.05 (d, J=9 Hz, 1H), 7.63 (d, J=8 Hz, 1H), 7.52–7.45 (m, 2H), 7.19 (d, J=7.5 Hz, 1H), 3.27 (br s, 4H), 2.80 (br s, 4H), 2.45 (s, 3H). Analysis calculated for $C_{20}H_{20}N_6$: C, 69.75; H, 5.85; N, 24.40. Found: C, 69.69; H, 5.72; N, 24.15.

EXAMPLE 33

7-(Imidazol-2-ono-[4,5-b ]pyridin-1-yl)-1-(4-methyl-1-piperazinyl)naphthalene

A mixture of the title product of example 29 (0.260 g, 0.78 mmol) and triethylamine (0.21 mL, 1.56 mmol) in methylene chloride (12 mL) was chilled to 0° C. and triphosgene (0.09 g, 0.30 mmol) was added all at once. The mixture became homogeneous and was stirred overnight at ambient temperature. Additional triphosgene (0.02 g, 0.07 mmol) was added and the mixture was stirred 4 hours more. Saturated sodium bicarbonate was added and the reaction was stirred 30 minutes to decompose any unreacted triphosgene. The phases were separated and the organic layer was washed with brine and dried through phase separating paper. The solution was concentrated and flash chromatographed on silica gel (1×4 inches). Gradient elution with from 60% to 100% methylene chloride/hexane was not productive. Continued elution with a gradient of from 2 to 4% methanol/methylene chloride gave 0.032 g of an oil which was discarded. Further elution with a gradient of 4 to 7% methanol/methylene chloride gave 0.23 g of crystalline solid product. The solid was triturated with methylene chloride and filtered to afford 0.079 g (28%) of the title product as a white powder: mp 260°–262° C. (dec.). $^1$H NMR (DMSO$_{d6}$) δ 11.44 (br s, 1H), 8.49 (d, J=1.5 Hz, 1H), 8.01 (d, J=9 Hz, 1H), 7.97 (dd, J=1.5, 5 Hz, 1H), 7.86 (dd, J =2, 9 Hz, 1H), 7.64 (d, J=8 Hz, 1H), 7.49–7.42 (m, 2H), 7.16–7.11 (m, 2H), 3.10 (br s, 4H), 2.58 (br s, 4H), 2.25 (s, 3H). HRMS m/e calculated for $C_{21}H_{21}N_5O$: 359.1742. Observed m/e: 359.1705. Analysis calculated for $C_{21}H_{21}N_5O \cdot H_2O$; C, 68.46; H, 6.02; N, 19.01. Found: C, 68.38; H, 5.47; N, 18.66.

EXAMPLE 34

1-(4-Methyl-1-piperazinyl)-7-(3-(3,3-dimethylformamidino)-2-pyridylamino)naphthalene To a solution of the title product of example 29 (0.453, 1.36 mmol) in dry dimethyl formamide (5 mL) was added dimethyl formamide dimethyl acetel (5 mL, 35.4 mmol). The resulting solution was refluxed 4 hours and allowed to stir at room temperature overnight. The solvent was removed in vacuo and the residue was flash chromatographed on silica gel (1×7 inches). Gradient elution with from 50 to 100% of ethyl acetate/hexane then a gradient of from 1 to 6% ethanol/ethyl acetate gave 0.352 g (67%) of the title product as a yellow foam which was suitable for further reaction. A sample was recrystallized from ether gave the bright yellow crystalline title product for analysis: mp 108°–111° C. $^1$H NMR δ 9.00 (d, J=2 Hz, 1H), 8.03–7.97 (m, 2H), 7.73 (d, J=9 Hz, 1H), 7.53–7.42 (sym m, 2H), 7.23 (t, J=8 Hz, 1H), 7.05–6.98 (sym m, 2H), 6.69 (dd, J=5, 7.5 Hz, 1H), 3.24 (br s, 4H), 3.13 (br s, 6H), 2.80 (br s, 4H), 2.46 (s, 3H). Analysis calculated for $C_{23}H_{28}N_6$; C, 71.10; H, 7.26; N, 21.63. Found: C, 71.16; H, 7.17; N, 21.59.

EXAMPLE 35

7-(Imidazolo[4,5-b]pyridin-1-yl)-1-(4-methyl-1-piperazinyl)-naphthalene

The title product of example 34 (0.25 g, 0.64 mmol) was slurried in toluene and a catalytic amount of para toluenesulfonic acid (a couple of crystals) was added. The mixture was refluxed 4 hours, cooled and concentrated. The residue was taken up in methylene chloride and washed with saturated sodium bicarbonate and brine; then it was dried over calcium sulfate and concentrated to a yellow oil (0.165 g). The oil was further purified by recrystallization from ether to afford 0.057 g (26%) of the title product as yellow crystals: mp 107°–112° C; $^1$H NMR δ 8.65 (d, J=2 Hz, 1H), 8.52–8.48 (m, 2H), 8.21 (dd, J=1.5, 8 Hz, 1H), 8.04 (d, J=8.5 Hz, 1H), 7.87 (dd, J=2, 8 Hz, 1H), 7.64 (d, J=8 Hz, 1H), 7.46 (t, J=8 Hz, 1), 7.36 (dd, J=5, 8 Hz, 1H), 7.20 (d, J=7 Hz, 1H), 3.24 (br s, 4H), 2.75 (br s, 4H), 2.43 (s, 3H). Analysis calculated for $C_{21}H_{21}N_5 \cdot H_2O$: C, 71.57; H, 6.29; N, 19.87. Found: C, 71.32; H, 6.32; N, 19.44.

EXAMPLE 36

7-(Imidazolo[4,5-b]pyridin-1-yl)-1-(4-methyl-1-piperazinyl)-naphthalene

The title product of example 29 (0.217 g, 0.65 mmol) was dissolved in acetic acid (3 mL) and diethyl ethoxymethylenemalonate (0.138 mL, 0.68 mmol) was added. The mixture was stirred at 55° C. for 5 hours. The reaction was cooled and diethyl ethoxymethylenemalonate (0.04 mL, 0.2 mmol) was added. The reaction was heated to 100° C. overnight. The solvent was removed in vacuo and the residue was taken up in chloroform and neutralized with ice cold saturated sodium bicarbonate and washed with brine. The organic layer was dried over calcium sulfate, concentrated and flash chromatographed on silica gel (1×2.5 inches). Elution with methylene chloride and then 2% methanol/0.05% ammonium hydroxide/methylene chloride gave an unweighed forerun. Continued elution with 4% methanol/0.05% ammonium hydroxide/methylene chloride gave a tan oil which crystallized upon scratching. The crystals were collected, rinsed with ether, and dried to afford 0.066 g, (30%) of the title compound: mp 107°–112° C.; $^1$H NMR δ 8.65 (d, J=2 Hz, 1H), 8.52–8.48 (m, 2H), 8.21 (dd, J=1.5, 8 Hz, 1H), 8.04 (d, J=8.5 Hz, 1H), 7.87 (dd, J=2, 8 Hz, 1H), 7.64 (d, J=8 Hz, 1H), 7.46 (t, J=8 Hz, 1), 7.36 (dd, J=5, 8 Hz, 1H), 7.20 (d, J=7 Hz, 1H), 3.24 (br s, 4H), 2.75 (br s, 4H), 2.43 (s, 3H).

EXAMPLE 37

7-(Benzimidazol-1-yl)-1-(4-methyl-1-piperazinyl)-naphthalene

To a slurry of 10% palladium on carbon (0.022 g) in ethanol (5 mL) was added the product of example 28 (0.091 g, 0.25 mmol in 25 mL of dioxane). Methanol (5 mL) was added and the mixture was hydrogenated at 50 psi for 6 hours. The reaction was filtered through celite and concentrated to afford a residue which was used without purification.

The above residue was dissolved in acetic acid (1.5 mL) and diethyl ethoxymethylenemalonate (0.058 mL, 0.29 mmol) was added. The mixture was stirred at 95° C. for 2 hours. The mixture was chilled to 0° C. and neutralized with 1 N NaOH. The mixture was extracted with methylene chloride and this organic layer was washed with brine, dried through phase separating paper, and concentrated for flash chromatography on silica gel (1×2 inches). 50 to 100% ethyl acetate/hexane gradient elution was not productive. Continued elution with 1 and 2% ethanol/ethyl acetate gave an unweighed forerun. Further elution with a gradient of from 4 to 15% ethanol/ethyl acetate gave 0.083 g of a brown oil. The oil was recrystallized from ether to yield 0.039 g (47%) of the title compound as tan crystals: mp 148°–150° C. $^1$H NMR δ 8.35 (d, J=2 Hz, 1H), 8.25 (s, 1H), 8.04 (d, J=8.5 Hz, 1H), 7.94 (sym m, 1H), 7.69–7.60 (m, 3H), 7.52 (t, J=8 Hz, 1H), 7.38 (sym m, 2H), 7.24 (d, J=7.5 Hz, 1H), 3.19 (br s, 4H), 2.70 (br s, 4H), 2.40 (s, 3H). HRMS m/e calculated for $C_{22}H22N4$: 342.1840. Observed m/e: 342.1863.

EXAMPLE 38

7-(3-Hydroxy-3-methyl-1-butynyl)1-(4-methyl-1-piperazinyl)-naphthalene p-toluene sulfonate 7-trifluoromethylsulfonyloxy-1-(4-methyl-1-piperazinyl)-naphthalene (0.285 g, 0.761 mmol), 3-hydroxy-3-methylbutyne (0.12 mL, 1.24 mmol), triethylamine (0.52 mL, 3.73 mmol), and bis (triphenylphosphine) palladium chloride (0.03 g, 0.04 mmol) were combined in dry dimethyl formamide (3 mL) and heated to 70° to 80° C. After 40 min the reaction was cooled and poured into 30 mL of 1N aqueous lithium chloride and extracted with ether (3×15 mL). The combined ether layer was washed with water and brine; then it was dried over magnesium sulfate and concentrated to an orange oil. The oil was purified by flash chromatography on silica gel (1×6 inches). Elution with a gradient of ethyl acetate and hexane followed by 100% ethyl acetate gave 0.15 g of orange oily product (65%). The oil was dissolved in ether (5 mL) and p-toluene sulfonic acid (0.093 g, 0.489 mmol in ether) was added. An orange solid formed which was collected, rinsed well with ether and ethyl acetate. Recrystallization from ethanol/ether gave 0.113 g (30%) of the title product as a dark orange solid; mp 194.5°–195.5° C. $^{13}$C NMR (DMSO d$_6$) δ 147.46, 145.70, 137.86, 133.54, 128.99, 128.66, 128.17, 127.75, 126.90, 125.59, 125.53, 124.23, 120.07, 116.59, 96.66, 81.06, 63.78, 53.02, 42.33, 31.70, 20.80.

EXAMPLE 39

7-(2-Ethylsulfonyl)ethenyl-1-(4-methyl-1-piperazinyl)-naphthalene (L) tartrate

The title product was prepared following the procedure of example 1 from 7-trifluoromethylsulfonyloxy-1-(4-methyl-1-piperazinyl)-naphthalene (0.25 g, 0.67 mmol), 2-ethylsulfonyl-1-chloroethane (0.11 g, 0.7 mmol), triethylamine (0.47 mL, 3.37 mmol), and bis (triphenylphosphine) palladium chloride (0.025 g, 0.036 mmol) in dimethyl formamide (10 mL), the reaction being carried out at reflux for 4 hours followed by stirring at ambient temperature overnight. The product was purified by flash chromatography on silica gel (1×4 inches). Elution with 50 and 75% ethyl acetate/hexane gave recovered starting material (0.07 g, 28%). Continued elution with ethyl acetate and then 10% methanol/ethyl acetate gave 0.06 g (26%) of product; $^1$H NMR δ 8.31 (d, J=1 Hz, 1H), 7.85–7.77 (m, 2H), 7.62–7.44 (m, 3H), 7.15 (dd, J=1.3, 7.2 Hz, 1H), 6.90 (d, J=15.5 Hz, 1H), 3.19–3.10 (m, 6H), 2.75 (m, 4H), 2.45 (s, 3H), 1.42 (t, J=7.5 Hz, 3H). The (L) tartrate salt was formed in methanol with 1 equivalent of (L) tartaric acid. Concentration of the methanolic solution and recrystallization from ethyl acetate/ether gave 0.035 g of light yellow hygroscopic solid title product: mp 110°–120° C. Analysis calculated for $C_{19}H_{24}N_2O_2S \cdot C_4H_6O_6 \cdot 2H_2O$: C, 52.07; H, 6.46; O, 5.27. Found: C, 51.70; H, 5.89; N, 5.11.

EXAMPLE 40

7-(4-Chlorobenzyloxy)-1-(4-methyl-1-piperazinyl)-naphthalene

7-Hydroxy-α-tetralone (1.0 g, 6.17 mmol), 4-chlorobenzyl bromide (1.27 g, 6.18 mmol), and potassium carbonate (1.7 g, 12.3 mmol) were combined in acetone (50 mL) and refluxed 4.5 hours. The mixture was cooled to room temperature, filtered and concentrated to a yellow solid. This material was recrystallized from ether to yield 1.28 g (72%) of 7-(4-chlorobenzyloxy)-a-tetralone as a light yellow solid: mp 91°–92° C. Analysis calculated for $C_{17}H_{15}ClO_2$: C, 71.20; H, 5.27. Found: C, 71.22; H, 5.20.

The product of the above reaction (1.0 g, 3.49 mmol) was combined with N-methylpiperazine (1.25 mL, 11.27 mmol) in dry tetrahydrofuran (THF, 50 mL) and chilled to −78° C. A solution of titanium tetrachloride (0.52 mL, 4.74 mmol) in methylene chloride (2 mL) was added dropwise over 3 minutes resulting in a milky green solution. The reaction was warmed to ambient temperature and stirred 2.5 hours; then it was quenched with 50 mL of a 2/1 mixture of water and ammonium hydroxide. The THF was removed with a stream of nitrogen. The residual aqueous phase was extracted with ethyl acetate (2x). The organic extracts were dried over magnesium sulfate and concentrated in vacuo to give 1.22 g (95%) of 7-(4-chlorobenzyloxy)-1-(4-methyl-1-piperazinyl)-3,4-dihydronaphthalene as a light yellow solid: mp 115°–116.5° C. Analysis calculated for $C_{22}H_{25}ClN_2O$: C, 71.63; H, 6.83; N, 7.59. Found: C, 71.54; H, 6.56; N, 6.95.

The product of the above reaction (1.2 g) was combined with 10% palladium on carbon (0.62 g, predried)in dry toluene (50 mL) and refluxed. After several hours of reflux, 0.5 g more catalyst was added and the reaction was further refluxed overnight. The reaction was cooled to room temperature and filtered through celite. The pad was rinsed well with ethyl acetate. Concentration yielded an orange oil which was purified by flash chromatography on silica gel (1×4 inches). Elution with 50% ethyl acetate/hexane gave unweighed recovered starting material. Continued elution as above gave 0.54 g of 7-hydroxy-1-(4-methyl-1-piperazinyl)-naphthalene. Further elution with ethyl acetate gave the title product (0.06 g). The title product was recrystallized from ether to afford 0.033 g (2.7%) of light yellow solid: mp 111.5°–112° C. Analysis calculated for $C_{22}H_{23}ClN_2O$: C, 72.02; H, 6.32; N, 7.64. Found: C, 71.92; H, 6.27; N, 7.69.

EXAMPLE 41

7-(3-Methylaminosulfonylphenyl)-1-(4-methyl-1-piperazinyl)naphthalene

7-Trimethylstannyl-1-(4-methyl-1-piperazinyl)-naphthalene (0.25 g, 0.67 mmol), 3-methylaminosulfonyl-1-bromobenzene (0.18 g, 0.72 mmol), triethylamine (0.45 mL, 3.23 mmol), lithium chloride (0.088 g, 2.07 mmol), and bis (triphenylphosphine) palladium chloride (0.025 g, 0.036 mmol) were combined in DMF (12.5 mL) and heated to 110° to 110° C. for 45 minutes. The reaction was cooled to room temperature and 1 N aqueous lithium chloride (20 mL) was added. The mixture was extracted with ether (2x). The combined organic layer was washed with 1N lithium chloride and brine; then it was dried over magnesium sulfate and concentrated to an orange oil. Flash chromatography on silica gel (1×6 inches) with an ethyl acetate/hexane gradient of from 50 to 75% followed by continued elution with ethyl acetate and finally 5% methanol/ethyl acetate 0.11 g (42%) of the title product. The sample was recrystallized from ethyl acetate for analysis: mp 147.5°–148° C. Analysis calculated for $C_{22}H_{25}N_3O_2S$: C, 66.81; H, 6.31; N, 10.62. Found: C, 66.32; H, 6.16; N, 10.41.

EXAMPLE 42

7-(3-Methylsulfonylaminophenyl)-1-(4-methyl-1-piperazinyl)-naphthalene

The title product was prepared following the procedure of example 41 from 7-trimethylstannyl-1-(4-methyl-1-piperazinyl)-naphthalene (0.25 g, 0.67 mmol), 3-methylsulfonylamino-1-bromobenzene (0.18 g, 0.72 mmol), triethylamine (0.45 mL, 3.23 mmol), lithium chloride (0.088 g, 2.07 mmol), and bis (triphenylphosphine) palladium chloride (0.025 g, 0.036 mmol) in DMF (12.5 mL) with a heating time of 1.5 hours. The product was obtained in 35% yield. A sample was obtained by recrystallization from ethyl acetate for analysis: mp 100°–101 ° C. Analysis calculated for $C_{22}H_{25}N_3O_2S \cdot 1.5\ H_2O$: C, 62.54; H, 6.68; N, 9.94. Found: C, 62.70; H, 6.46; N, 9.89.

EXAMPLE 43

7-Benzoyl-1-(4-methyl-1-piperazinyl)naphthalene

7-Trimethylstannyl-1-(4-methyl-1-piperazinyl)-naphthalene (0.1 g, 0.27 mmol), benzoyl chloride (0.031 mL, 0.27 mmol) and bis (acetonitrile) palladium chloride (0.007 g, 0.027 mmol) were combined in chloroform (5 mL) and heated to 60° to 65° C. for 15 minutes. The reaction was cooled to room temperature and saturated aqueous ammonium chloride (10 mL) and chloroform (10 mL) were added, Phases were separated and the organic layer was washed with brine, dried over magnesium sulfate, and concentrated to a milky oil. The oil was purified by flash chromatography on silica gel (1×6 inches), the product eluting with 5% methanol/ethyl acetate as a yellow oil (0.07 g, 79%). The oil was crystallized from ether to obtain a bright yellow solid: mp 124°–124.5° C. Analysis calculated for $C_{22}H_{22}N_2O$: C, 79.97; H, 6.71; N, 8.48. Found: C, 79.74; H, 6.69; N, 8.46.

EXAMPLE 44

7-(α-Hydroxybenzyl)-1-(4-methyl-1-piperazinyl)-naphthalene

The title product of example 43 (0.121 g, 0.366 mmol) was dissolved in ethanol (3 mL) and sodium borohydride (0.025 g, 0.66 mmol) was added. The mixture was stirred 1 hour at ambient temperature, then it was concentrated at reduced pressure at 40° C. The residue was partitioned between ethyl acetate and water and the phases were separated. The organic layer was washed with water and brine; then it was dried over magnesium sulfate and concentrated to a light yellow oil. The oil was purified by flash chromatography on silica gel (1×4 inches). Elution with 50% ethyl acetate/hexane removed a fast moving component which was not identified. Continued elution with ethyl acetate gave 0.066 mg of the title product as a light tan oil which solidified. This solid was recrystallized from chloroform/ether to afford 0.033 mg (27%) of the title product as a light tan solid: mp 162.5°–163° C. Analysis calculated for $C_{22}H_{24}N_2O \cdot 0.25\ H_2O$: C, 78.42; H, 7.33; N, 8.31. Found: C, 78.52; H, 7.06; N, 8.31.

EXAMPLE 45

7-(Diphenylhydroxymethyl)-1-(4-methyl-1-piperazinyl)-naphthalene

The title product of example 43 (0.072 g, 0.218 mmol) was dissolved in dry THF (10 mL) and chilled to 0° C. Phenyl magnesium bromide (3 M in ether, 0.08 mL, 0.24 mmol) was added dropwise. The mixture turned greenish and then returned to a yellow color. The reaction was allowed to warm to room temperature for 30 minutes and then refluxed for 45 minutes. Additional phenyl magnesium bromide (0.1 mL, 0.26 mmol) was added and the mixture was refluxed 1 hour more. Saturated aqueous ammonium chloride was added and the mixture was extracted with ethyl acetate. The organic phase was washed with brine, dried over magnesium sulfate and concentrated to a light yellow oil. The product was purified by silica gel flash chromatography (1×6 inches). Elution with 50% ethyl acetate/hexane followed by ethyl acetate gave 0.082 g (92%) of the title product. A sample was recrystallized from chloroform/ether for analysis: mp 217.5°–218.5° C. Analysis calculated for $C_{28}H_{28}N_2O \cdot 0.5\ H_2P$: C, 80.54; H, 7.00; N, 6.71. Found: C, 80.47; H, 6.63; N, 6.78.

EXAMPLE 46

7-(p-Biphenyl)-1-(4-methyl-1-piperazinyl)-naphthalene

The title product was prepared following the procedure of example 41 from 7-trimethylstannyl-1-(4-methyl-1-piperazinyl)-naphthalene (0.25 g, 0.67 mmol), 4-bromobiphenyl (0.17 g, 0.73 mmol), triethylamine (0.45 mL, 3.23 mmol), lithium chloride (0.088 g, 2.07 mmol), and bis (triphenylphosphine) palladium chloride (0.025 g, 0.036 mmol) in DMF (12.5 mL) with a heating time of 1 hour at 100 to 115° C. The product obtained was 0.14 g (56%) in yield. A sample was obtained by recrystallization from ether/hexane for analysis: mp 138.5°–139.5° C. Analysis calculated for $C_{27}H_{26}N_2$: C, 85.67; H, 6.92; N, 7.40. Found: C, 85.12; H, 6.97; N, 7.44.

EXAMPLE 47

7-(3-Methoxycarbonylphenyl)-1-(4-methyl-1-piperazinyl)-naphthalene

The title product was prepared following the procedure of example 41 from 7-trimethylstannyl-1-(4-methyl-1-piperazinyl)-naphthalene (0.25 g, 0.67 mmol), 3-methoxycarbonyl-1-bromobenzene (0.16 g, 0.74 mmol), triethylamine (0.45 mL, 3.23 mmol), lithium chloride (0.088 g, 2.07 mmol), and bis (triphenylphosphine) palladium chloride (0.025 g, 0.036 mmol) in DMF (12.5 mL) with a heating time of 1.5 hours at 120 to 130° C. The product obtained was 0.15 g (63%) in yield as an oil which was converted to a hydrochloride salt with HCl gas in ether. The solid was collected under a nitrogen atmosphere and recrystallized from chloroform/ether for analysis: mp 201°–203° C.; $^{13}$C NMR δ 167.05, 147.37, 141.78, 137.80, 134.08, 131.87, 130.89, 129.57, 129.07, 128.63, 128.47, 126.28, 125.76, 125.02, 120.59, 116.85, 54.30, 52.33, 49.75, 43.70.

EXAMPLE 48

7-(3-Fluorophenyl)-1-(4-methyl-1-piperazinyl)-naphthalene

The title product was prepared following the procedure of example 41 from 7-trimethylstannyl-1-(4-methyl-1-piperazinyl)-naphthalene (0.25 g, 0.67 mmol), 3-fluoro-1-bromobenzene (0.13 g, 0.74 mmol), triethylamine (0.45 mL, 3.23 mmol), lithium chloride (0.088 g, 2.07 mmol), and bis (triphenylphosphine) palladium chloride (0.025 g, 0.036 mmol) in DMF (12.5 mL) with a heating time of 2 hours at 120 to 130° C. The product obtained was 0.13 g (59%) in yield. A sample was obtained by recrystallization from ether/hexane for analysis: mp 116°–116.5° C. Analysis calculated for $C_{22}H_{21}FN_2$: C, 79.49; H, 6.37; N, 8.43. Found: C, 79.07; H, 6.46; N, 8.66.

EXAMPLE 49

7-(Benzyloxy)-1-(4-methyl-1-piperazinyl)-naphthalene

7-Hydroxy-α-tetralone (1.0 g, 6.17 mmol), benzyl bromide (0.80 mL, 6.73 mmol), and potassium carbonate (1.7 g, 12.3 mmol) were combined in acetone (50 mL) and refluxed 22 hours. The mixture was cooled to room temperature, filtered and concentrated at reduced pressure. The residue was partitioned between ethyl acetate and 1N sodium hydroxide. The phases were separated and the organic layer was washed with water and brine; then it was dried over magnesium sulfate and concentrated to a pale yellow solid. The material was recrystallized from ether/hexane to yield 0.80 g (51%) of 7-benzyloxy-α-tetralone as a cream solid: mp 84°–84.5° C. Analysis calculated for $C_{17}H_{16}O_2$: C, 80.93; H, 6.39. Found: C, 80.39; H, 6.11.

The product of the above reaction (0.75 g, 2.97 mmol) was combined with N-methylpiperazine (1.06 mL, 9.56 mmol) in dry tetrahydrofuran (THF, 50 mL) and chilled to −78° C. A solution of titanium tetrachloride (0.44 mL, 4.01 mmol) in methylene chloride (2 mL) was added dropwise over 3 minutes resulting in a milky green solution. The reaction was warmed to ambient temperature and stirred overnight; then it was quenched with 50 mL of a 2/1 mixture of water and ammonium hydroxide. The THF was removed with a stream of nitrogen. The residual aqueous phase was extracted with ethyl acetate (2 x). The organic extracts were dried over magnesium sulfate and concentrated in vacuo to give 0.93 g (94%) of 7-benzyloxy-1-(4-methyl-1-piperazinyl)-3,4-dihydronaphthalene as an orange oil which was suitable for use without further purification. 1H NMR δ 7.48–7.28 (m, 5H), 7.08–7.05 (m, 2H), 6.79 (dd, J=2.7, 8.2 Hz, 1H), 5.30 (t, J=4.7 Hz), 5.10 (s, 2H), 2.84 (br s, 4H), 2.64–2.50 (t, J=7.5 Hz overlapping with br s centered at δ 2.54, 6H total), 2.37 (s, 3H), 2.25–2.17 (m, 2H).

The product of the above reaction (0.93 g, 2.78 mmol) was combined with 10% palladium on carbon (0.65 g, predried) in dry toluene (30 mL) and refluxed overnight. The reaction was cooled to room temperature and filtered through celite, The pad was rinsed well with ethyl acetate. Concentration yielded a yellow oil which was purified by flash chromatography on silica gel (1×4 inches). Elution with 50% ethyl acetate/hexane gave unweighed recovered starting material. Continued elution with 75% ethyl acetate/hexane gave 0.18 g of 7-benzyloxy-1-(4-methyl-1-piperazinyl)naphthalene as a colorless oil. Recrystallization from ether gave 0.09 g (9.8%) of the tile product as a white solid: mp 81.5°–82.5° C. Analysis calculated for $C_{22}H_{24}N_2O$: C, 79.48; H, 7.28; N, 8.43. Found: C, 79.29; H, 7.41; N, 8.30. Further elution with ethyl acetate gave 0.47 g of 7-hydroxy-1-(4-methyl-1-piperazinyl)-naphthalene.

EXAMPLE 50

7-(3,4-Dichlorobenzyloxy)-1-(4-methyl-1-piperazinyl)-naphthalene

7-Hydroxy-α-tetralone (1.0 g, 6.17 mmol), 3,4-dichlorobenzyl bromide (1.48, 6.18 mmol), and potassium carbonate (1.7 g, 12.3 mmol) were combined in acetone (50 mL) and refluxed 21.5 hours. The mixture was cooled to room temperature, filtered and concentrated at reduced pressure. The reside was partitioned between ethyl acetate and 1N sodium hydroxide. The phases were separated and the organic layer was washed with water and brine; then it was dried over magnesium sulfate and concentrated to a pale yellow solid. This material was recrystallized from ether to yield 1.04 g (53%) of 7-(3,4-dichlorobenzyloxy-α-tetralone as a fluffy white solid: mp 122.5°–123° C. Analysis calculated for $C_{17}H_{14}Cl_2O_2$: C, 63.57; H, 4.39. Found: C, 63.36; H, 4.21.

The product of the above reaction (0.90 g, 2.8 mmol) was combined with N-methylpiperazine (1.0 mL, 9.01 mmol) in dry tetrahydrofuran (THF, 50 mL) and chilled to -78° C. A solution of titanium tetrachloride (0.42 mL, 3.83 mmol) in methylene chloride (2 mL) was added dropwise over 3 minutes resulting in a milky green solution. The reaction was warmed to ambient temperature and stirred overnight; then it was quenched with 50 mL of a 2/1 mixture of water and ammonium hydroxide. The THF was removed with a stream of nitrogen. The residual aqueous phase was extracted with ethyl acetate (2x). The organic extracts were dried over magnesium sulfate and concentrated in vacuo to give 1.08 g (96%) of 7-(3,4-dichlorobenzyloxy-1-(4-methyl-1-piperazinyl)-3,4-dihydronaphthalene as a yellow oil which was suitable for use without further purification. $^1$H NMR δ 7.55 (d, J=2 Hz, 1H), 7.45 (d, J=8.2 Hz, 1H), 7.29–7.25 (m, 1H), 7.07 (d, J=8.2 Hz, 1H), 7.00 (d, J=2.7 Hz, 1H), 6.75 (dd, J=2.7, 8.2 Hz, 1H), 5.30 (t, J=4.7 Hz, 1H), 5.05 (s, 2H), 2.80 (br s, 4H), 2.63–2.43 (m, 6H), 2.36 (s, 3H), 2.30–2.16 (m, 2H).

The product of the above reaction (1.08 g, 2.68 mmol) was combined with 10% palladium on carbon (0.65 g, predried) in dry toluene (30 mL) and refluxed overnight. The reaction was cooled to room temperature and filtered through celite. The pad was rinsed well with ethyl acetate. Concentration yielded a brown oil which was purified by flash chromatography on silica gel (1×4 inches). Elution with 75% ethyl acetate/hexane gave an unweighted forerun. Continued elution with ethyl acetate gave 0.22 g of light yellow solid. Recrystallization from ether gave 0.148 g (14%) of the title product as a straw colored solid: mp 113°–114° C. Analysis calculated for $C_{22}H_{22}Cl_2N_2O$: C, 65.84; H, 5.53; N, 6.98. Found: C, 66.18; H, 5.63; N, 7.02.

EXAMPLE 51

7-(4-Trifluoromethylbenzyloxy)-1-(4-methyl-1-piperazinyl)-naphthalene

To a mixture of 7-hydroxy-1-(4-methyl-1-piperazinyl)-naphthalene (0.20 g, 0.83 mmol), triphenylphosphine (0.32 g, 1.22 mmol), and 4-trifluoromethylbenzyl alcohol (0.17 mL, 1.26 mmol) in dry THF (4 mL) was added diethyl azodicarboxylate in THF (1 mL). The mixture was stirred overnight at ambient temperature; then it was concentrated at reduced pressure. The residue was partitioned between ethyl acetate and 1N sodium hydroxide. The organic layer was washed with water and brine; then it was dried over magnesium sulfate and concentrated onto silica gel for flash chromatographic purification (1×6 inches). Elution with 75% ethyl acetate/hexane gave 0.24 g (72%) of the title compound as a nearly colorless oil. The oil was treated with HCl in ether to form the hydrochloride salt (0.23 g) which was recrystallized from chloroform/ether to give 0.14 g of a white solid thereof: mp 205°–206° C. Analysis calculated for $C_{23}H_{23}F_3N_2O \cdot HCl \cdot 0.25 H_2O$: C, 62.58; H, 5.59; N, 6.35. Found: C, 62.59; H, 5.63; N, 6.40.

EXAMPLE 52

7-Benzoyloxy-1-(4-methyl-1-piperazinyl)-naphthalene

A mixture of 7-hydroxy-1-(4-methyl-1-piperazinyl)-naphthalene (0.065 g, 0.268 mmol) and benzoyl chloride (0.035 mL, 0.302 mmol) in methylene chloride (1 mL) and saturated sodium bicarbonate (1 mL) was stirred at room temperature. After several hours, a second equivalent of benzoyl chloride was added with continued stirring overnight. The reaction was diluted with ethyl acetate and the phases were separated. The organic layer was washed with 1N sodium hydroxide, water and brine; then it was dried over magnesium sulfate and concentrated to an oil which solidified (0.065 g, 69%). A sample recrystallized from ether/hexane as a light pink solid was submitted for analysis: mp 82°–82.5° C. Analysis calculated for $C_{22}H_{22}N_2O_2 \cdot 0.25 H_2O$: C, 75.30; H, 6.46; N, 7.98. Found: C, 75.51; H, 6.29; N, 7.97.

EXAMPLE 53

7-(4-Chlorobenzoyloxy)-1-(4-methyl-1-piperazinyl)-naphthalene

The title product was obtained following the procedure of example 30 from 7-hydroxy-1-(4-methyl-1-piperazinyl)-naphthalene (0.065 g, 0.268 mmol) and 4-chlorobenzoyl chloride (0.035 mL, 0.275 mmol) in methylene chloride (1 mL) and saturated sodium bicarbonate (1 mL) with a second equivalent of 4-chlorobenzoyl chloride added after several hours of stirring at room temperature. The title product was obtained in a yield of 0.058 g (57%) after recrystallization from ether/hexane: mp 110°–111° C. Analysis calculated for $C_{22}H_{21}ClN_2O_2$: C, 69.38; H, 5.56; N, 7.36. Found: C, 69.31; H, 5.61; N, 7.35.

EXAMPLE 54

7-(3-Chlorobenzyloxy)-1-(4-methyl-1-piperazinyl)-naphthalene

A mixture of 3-chlorobenzyl bromide (1.27 g, 6.18 mmol), 7-hydroxy-α-tetralone (1.0 g, 6.17 mmol), and potassium carbonate (1.7 g, 12.3 mmol) in acetone (30 mL) was refluxed overnight. The reaction was cooled, filtered, and concentrated at reduced pressure. The residue was partitioned between ethyl acetate and 1N sodium hydroxide. The organic phase was washed with water and brine, dried over magnesium sulfate, and concentrated to a yellow solid. Recrystallization from ether/hexane gave 0.87 g (49%) of 7-(3-chlorobenzyloxy)-α-tetralone as a cream colored solid: mp 77°–78° C. Analysis calculated for $C_{17}H_{15}ClO_2$: C, 71.20; H, 5.27. Found: C, 71.25; H, 5.09.

A solution of 7-(3-chlorobenzyloxy)-α-tetralone (0.8 g, 2.79 mmol) and 1-methylpiperazine (1.0 mL, 4.0 mmol) in dry THF (50 mL) was cooled to −78° C. and treated with titanium tetrachloride (0.42 mL, 3.83 mmol) in methylene chloride (2 mL). The reaction was stirred 10 minutes at −78° C., then warmed to room temperature and stirred overnight. The mixture was quenched with 50 mL of 5N ammonia and extracted with ethyl acetate (2x). This combined organic layer was dried over magnesium sulfate and concentrated to a colorless oil (0.98 g, 95%). This enamine was used directly in the next step.

A mixture of the enamine (1.0 g, 2.71 mmol) and sulfur (1.1 g, 34.31 mmol) in decalin (10 mL) was lowered into an oil bath preheated to 170° C. The mixture was stirred 20 minutes; then it was cooled and the decalin was removed by short path distillation. The residue was dissolved in carbon disulfide and flash chromatographed on silica gel (1×6 inches). Elution with carbon disulfide removed residual sulfur. Continued elution with 50% ethyl acetate/hexane and finally with pure ethyl acetate gave 0.09 g of brown oil. The product was combined with 0.03 g of product from a previous preparation and treated with decolorizing carbon in ether. Recrystallization from hexane gave 0.026 g (2.6%) of the title product as a light yellow solid: mp 67.5°–68° C. Analysis calculated for $C_{22}H_{23}ClN_2O$: C, 72.02; H, 6.32; N, 7.64. Found: C, 71.95; H, 6.32; N, 7.47.

EXAMPLE 55

7-Trifluoromethylsulfonyloxy-1-(4-methyl-1-piperazinyl)-naphthalene

7-Hydroxy-1-(4-methyl-1-piperazinyl)-naphthalene (4.1 g, 16.9 mmol) and triethylamine (12.8 mL, 91.8 mmol) were dissolved in methylene chloride (150 mL) and cooled to −78° C. Triflic anhydride (3.04 mL, 18.1 mmol) was added via syringe and the reaction was warmed to room temperature and stirred overnight. The reaction was again chilled to −78° C. and additional triflic anhydride (1 mL) and triethylamine (2 mL) were added but after 2 hours stirring at ambient temperature, no further reaction occurred. Saturated ammonium chloride was added and the mixture was concentrated. The residue was partitioned between ethyl acetate and water. The organic layer was washed with water and brine, dried over magnesium sulfate and concentrated to a brown oil which was purified by silica gel flash chromatography (2×6 inches). Elution with 75% ethyl acetate/hexane gave 4.49 g (71%) of the title product as a light brown solid: mp 70°–71° C. Analysis calculated for $C_{16}H_{17}F_3N_2O_3S$: C, 51.33; H, 4.58; N, 7.48. Found: C, 51.35; H, 4.46; N, 7.49.

EXAMPLE 56

7-Benzamido-1-(4-methyl-1-piperazinyl)-naphthalene

7-Benzamido-1-(4-methyl-1-piperazinyl)-3,4-dihydronaphthalene (0.795 g, 2.29 mmol, an intermediate from Example 1), freshly distilled dicyclopentadiene (70° C. at 1 Torr, 0.909 g, 6.87 mmol), and 10% palladium on carbon (0.2 g, predried) were combined in xylene (25 mL) and refluxed 4 hours. The mixture was cooled and additional palladium on carbon (0.3 g) was added. The reaction was refluxed vigorously and xylene was distilled out of the reaction until the volume of the reaction was reduced to about 10 mL. The reaction was refluxed overnight, cooled, and filtered through celite. The filtrate was concentrated on silica gel and flash chromatographed on silica gel. Gradient elution with from 50% to 100% ethyl acetate/hexane gave a forerun containing an unweighed amount of 7-benzamido-α-tetralone. Continued gradient elution with 2% to 10% methanol/ethyl acetate gave 0.49 g (62%) of the title product: mp 172°–173.5° C.

Alternatively, [2,2,2]bicyclooctene was used in place of dicyclopentadiene in the above dehydrogenation reaction to produce the title product in 66% yield after recrystallization from ethyl acetate/hexane.

EXAMPLE 57

7-Amino-1-(1-methyl-4-piperidinyl)-naphthalene

The following reaction was run in two side by side reactions and the crude products were combined for work up and purification. A mechanically stirred solution of 8-bromo-2-(dibenzylamino)-naphthalene (10.0 g, 24.9 mmol from Preparation 4) in tetrahydrofuran (200 mL) was cooled to –95° C. (hexane/liquid nitrogen) and butyllithium (10.39 mL, 24.9 mmol, 2.4 M) was added dropwise. The orange solution was stirred 7 min, then 1-methyl-4-piperidone (2.82 g, 24.9 mmol) was added dropwise over 10 minutes with a 10 mL tetrahydrofuran rinse. The orange color faded while stirring was continued 20 minutes at -100° C. The reaction was allowed to warm to room temperature and quenched with water. The solvent was removed and the residue was partitioned between methylene chloride and water (at this point the two reactions were combined). The phases were separated and the organic layer was washed with brine, dried, and concentrated onto silica gel. Flash chromatography (4×4 inches silica gel) proceeded as follows: methylene chloride (1 L) and 2% methanol/methylene chloride (1.6 L) unweighed white solid 7-dibenzylaminonaphthalene; 15% methanol / methylene chloride (1 L), 25% methanol/methylene chloride (1 L) and 30% methanol/methylene chloride/0.2% ammonium hydroxide (4 L) product contaminated with water. The combined eluents were concentrated and redissolved in methylene chloride. The solution was dried and concentrated to afford 15.09 g (69%) of 7-dibenzylamino-1-(4-hydroxy-1-methyl-4-piperidinyl)-naphthalene as a light tan foam. A sample recrystallized from ethyl acetate had mp 173°–174° C. Analysis calculated for $C_{30}H_{32}N_2O$: C, 82.53; H, 7.39; N, 6.42. Found: C, 82.42; H, 7.44; N, 6.38.

The product from the above reaction (15.0 g, 34.38 mmol), p-toluenesulfonic acid (7.85 g, 41.26 mmol) and toluene (500 mL) were combined and refluxed 4 hours with azeotropic removal of water. The mixture was allowed to stand at room temperature 48 hours, then additional p-toluenesulfonic acid (1.4 g) was added and the mixture was refluxed 5 hours more. The reaction was concentrated at reduced pressure and the residue was taken up in methylene chloride. This organic phase was washed with 1 N sodium hydroxide (2 x) and brine, then it was dried over calcium sulfate and concentrated to give 7-dibenzylamino-1-(1-methyl-1,2,5,6-tetrahydropyrid-4-yl)-naphthalene as a brown oil which crystallized on standing (13.8 g, 96%). This material was suitable for use in the next reaction. A sample recrystallized from ethyl acetate had mp 124°–126° C. The analytical sample was recrystallized from isopropanol. Analysis calculated for $C_{30}H_{30}N_2 \cdot 0.5\ H_2O$: C, 84.27; H, 7.31; N, 6.69. Found: C, 83.85; H, 6.97; N, 6.39.

A mixture of 7-dibenzylamino-1-(1-methyl-1,2,5,6-tetrahydropyrid-4-yl)-naphthalene (2.85 g, 6.81 mmol) and palladium hydroxide (20% on carbon, 2.06 g) in glacial acetic acid (60 mL) was hydrogenated 22 hours (starting pressure approximately 50 psi). Additional palladium hydroxide (1 g) was added and hydrogenation was continued 13 hours more. The reaction was filtered through celite. The filtrate was neutralized with 4N sodium hydroxide and extracted with methylene chloride. This organic phase was washed with brine, dried and concentrated to 1.3 g of brown oil. Crystallization from isopropanol gave 0.544 g (33%) of 7-amino-1-(1-methyl-4-piperidinyl)-naphthalene as light brown crystals. mp 169.5°–171° C. Analysis calculated for $C_{16}H_{20}N_2$; C, 79.96; H, 8.39; N, 11.66. Found: C, 80.14; H, 8.42; N, 11.52.

EXAMPLE 58

7-(3-nitro-2-pyridylamino)-1-(1-methyl-4-piperidinyl)-naphthalene

A mixture of the product from Example 57 (0.338 g, 1.4 mmol), 2-chloro-3-nitropyridine (0.446 g, 2.81 mmol), and 4-dimethylaminopyridine (0.172 g, 1.4 mmol) in dimethylformamide (6 mL) was refluxed 5 hours. The solvent was removed at reduced pressure and the residue was taken up in methylene chloride. The organic phase was washed with 1N sodium hydroxide and brine, then it was concentrated onto silica gel and flash chromatographed (1×4 inches silica gel). The elution proceeded as follows: 75% methylene chloride/hexane (175 mL) nil; methylene chloride (250 mL) unweighed excess 2-chloro-3-nitropyridine; 2% methanol/methylene chloride (200 mL) nil, (550 mL) 0.373 g of crude product contaminated with 4-dimethylamino-pyridine. This material was triturated with ether and filtered to give 0.17 g of title product as orange crystals. $^1$H NMR δ 10.34 (br s, 1 H), 8.59 (dd, J=2, 8.5 Hz, 1 H), 8.54–8.50 (m, 2 H), 7.88 (d, J=9 Hz, 1 H), 7.72–7.70 (m, 1 H), 7.66 (dd, J=2, 9 Hz, 1H), 7.45–7.41 (m, 2 H), 6.89 (dd, J=4.5, 8.5 Hz, 1 H), 3.27 (tt, J=4, 11.5 Hz, 1 H), 3.11 (long range coupled d, J=11.5 Hz, 1 H), 2.41 (s, 3 H), 2.27 (dt, J=2.5, 11.5 Hz, 2 H), 2.09–1.89 (m, 4 H).

EXAMPLE 59

7-(Imidazolo[4,5-b]pyridin-1-yl)-1-(1-methyl-4-piperidinyl)-naphthalene

A mixture of the product from Example 58 (0.18 g, 0.5 mmol) and 10% palladium on carbon (0.04 g)in ethanol (35 mL) and ethyl acetate (15 mL) was hydrogenated at 45 psi for 4 hours. The mixture was filtered through celite and concentrated to give 7-(3-amino-2-pyridylamino)-1-(1-methyl-4-piperidinyl)-naphthalene which was suitable for further reaction; $^1$H NMR δ 8.07 (d, J=2 Hz, 1 H), 7.89 (dd, J=1.5, 5 Hz, 1 H), 7.79 (d, J=9 Hz, 1 H), 7.64 (d, J=7.5 Hz, 1 H), 7.45 (dd, J=2, 9 Hz, 1 H), 7.36–7.26 (m, 2H with CHCl$_3$ from NMR solvent overlapping), 7.07 (dd, J=1.5, 7.5 Hz, 1 H), 6.82 (dd, J=5, 7.5 Hz, 1 H), 6.51 (br s, 1 H), 3.49 (br s, 2 H), 3.18 (tt, J=4, 12 Hz, 1H), 3.03 (long range coupled d, J=13.5 Hz, 2 H), 2.39 (s, 3 H), 2.23 (dt, J=2.5, 11.5 Hz, 2H), 2.08–1.87 (m, 4 H). HRMS m/e calculated for $C_{21}H_{24}N_4$: 332.1996. Observed m/e 332.2003.

The product from the above reaction and ethoxymethylenemalononitrile (0.079 g, 0.646 mmol) were combined in glacial acetic acid (7 mL) were refluxed 4 hours. The solvent was removed at reduced pressure and the residue was taken up in methylene chloride. The organic phase was washed with 1N sodium hydroxide and brine, then it was dried and concentrated. This residue was flash chromatographed on silica gel (1×3.5 inches). Gradient elution with from 50% ethyl acetate/hexane to pure ethyl acetate and then with from 2% to 5% methanol/ethyl acetate gave no product. Continued elution with from 15% to 40% methanol/ethyl acetate gave a tan foam product. Treatment with charcoal in methylene chloride, filtration and concentration gave 0.155 g of product. Recrystallization from ethyl acetate gave 0.04 g (23%) of the title compound as off white crystals. mp 118°–120° C. Analysis calculated for $C_{22}H_{22}N_4$: C, 77.16; H, 6.48; N, 16.36. Found: C, 76.99, H, 6.45; N, 16.27.

EXAMPLE 60

7-(4-Chlorobenzamido-1-(1-methyl-4-piperidinyl)-naphthalene

The product from Example 57 (0.202 g, 0.845 mmol), triethylamine (0.124 mL, 0.93 mmol) and 4-chlorobenzoyl chloride (0.118 mL, 0.93 mmol) were combined in acetonitrile (10 mL) at 0° C. The mixture was allowed to come to room temperature and stir overnight. The reaction was chilled back to 0° C. and a second equivalent of acid chloride and triethylamine were added. The mixture was heated to 90° C. overnight. The solvent was removed at reduced pressure and the residue was taken up in methylene chloride. The organic phase was washed with brine, dried, concentrated onto silica gel and flash chromatographed (0.5×3.5 inches), Elution proceeded as follows: methylene chloride then gradient elution with from 2% to 4% methanol/methylene chloride was unproductive. Continued elution with from 4% to 6% methanol/methylene chloride gave 0.214 g of white foam. Recrystallization from chloroform/ether gave 0.115 g of the title compound as tan crystals. mp 162°–164° C. The compound was converted to its hydrochloride salt with HCl in ether. Analysis calculated for $C_{23}H_{23}ClN_2O \cdot HCl$: C, 66.51; H, 5.82; N, 6.74. Found: C, 66.12; H, 5.76; N, 6.41.

EXAMPLE 61

7-Amino-1-(1-methyl-3-piperidinyl)-naphthalene

A solution of 8-bromo-2-(dibenzylamino)-naphthalene (9.75 g, 24.3 mmol product of Preparation 4) in tetrahydrofuran (270 mL) was cooled to -78° C. and butyllithium (9.72 mL, 24.4 mmol, 2.4 M) was added dropwise. The orange solution was stirred 20 minutes, then 1-t-butoxycarbonyl-3-piperidone (4.84 g, 24.3 mmol dissolved in 5 mL tetrahydrofuran) was added dropwise with a 5 mL tetrahydrofuran rinse. The reaction was stirred 30 minutes at −78° C., then allowed to warm to room temperature and stir 1 hour. The solvent was removed and the residue was partitioned between methylene chloride and water. The phases were separated and the organic layer was washed with brine, dried over calcium sulfate, and concentrated onto silica gel. Flash chromatography (3×3 inches silica gel) proceeded as follows: 5% ethyl acetate/hexane (1.4 L) and 10% ethyl acetate/hexane (1 L) unweighed white solid 7-dibenzylaminonaphthalene; 25 % ethyl acetate/hexane (1.5 L) 6.46 g (51%) of 7-dibenzylamino-1-(1-t-butoxycarbonyl-3-hydroxy-3-piperidinyl)-naphthalene which was suitable for use without further purification. A sample recrystallized from ethyl acetate/hexane had mp 145°–147° C.

The product of the above reaction (1.0 g, 1.9 mmol) and dry benzene (20 mL) were chilled to 0° C. and Burgess salt (0.958 g, 4.02 mmol) was added. The mixture was heated to 55° C. for 2 hours, then allowed to stir at ambient temperature overnight. Water was added and after stirring an additional 15 minutes, the phases were separated. The organic layer was washed with brine and the combined aqueous washes were back extracted with ethyl acetate. The combined organic layer was dried over calcium sulfate, concentrated onto silica gel and flash chromatographed (1×3 inches). Elution 2% to 4% ethyl acetate/hexane gave 0.68 g (70%) of a mixture of both possible dehydration products (7-dibenzylamino-1-(1-t-butoxycarbonyl-1,4,5,6-tetrahydropyrid-3-yl)-naphthalene and 7-dibenzylamino-1-(1-t-butoxycarbonyl-1,2,5,6-tetrahydropyrid-3-yl)-naphthalene). The products could be separated by careful chromatography but were carried as a mixture in this sequence.

A slurry of lithium aluminum hydride (0.172 g, 4.52 mmol) in tetrahydrofuran (20 mL) was chilled to 0° C. and the product of the above reaction (0.568 g, 1.13 mmol in 5 mL tetrahydrofuran) was added with a tetrahydrofuran rinse (2×2.5 mL). The mixture was refluxed 4 hours, chilled to 0° C. and quenched with sodium sulfate decahydrate. The reaction was filtered and the filter cake was rinsed well with methylene chloride. The filtrate was concentrated and the residue was taken up in methylene chloride. This organic phase was washed with water and brine, dried and concentrated to give 0.455 g of a 2:1 mixture of olefin products (7-dibenzylamino-1-(1-methyl-1,4,5,6-tetrahydropyrid-3-yl)-naphthalene and 7-dibenzylamino-1-(1-methyl-1,2,5,6-tetrahydropyrid-3-yl)-naphthalene) as judged by integration of the methyl signals in the NMR spectrum (2.52 ppm - major and 2.27 ppm - minor). This material was carried on without further purification or characterization.

The product mixture from the above reaction (4.0 g, 9.56 mmol) and palladium hydroxide (20% on carbon, 3.75 g) in glacial acetic acid (141 mL) and ethanol (141 mL) was hydrogenated 4 hours (starting pressure approximately 50 psi). Additional palladium hydroxide (0.8 g) was added and hydrogenation was continued 5 hours more. The reaction was filtered through celite. The filtrate was neutralized with 4N sodium hydroxide and extracted with methylene chloride. This organic phase was washed with brine, dried, concentrated onto silica gel and flash chromatographed (2×3 inches). Elution proceeded as follows: 75% ethyl acetate/hexane (400 mL), ethyl acetate (400 mL), and 2% methanol/ethyl acetate (400 mL), nil; 2% triethylamine/5% methanol/ethyl acetate (400 mL), 0.45 g of an unidentified brown foam; 2% triethylamine/6% methanol/ethyl acetate (500 mL) and 3% triethylamine/8% methanol/ethyl acetate (500 mL), 1.35 g (54%) of brown foam title product. Further purification by treatment with activated charcoal followed by trituration in ether gave 0.362 g of the title compound as pink crystals which had mp 117°–120° C. HRMS m/e calculated for $C_{16}H_{20}N_2$:240.1622. Observed m/e 240.1623. Analysis calculated for $C_{16}H_{20}N_2$: C, 79.96; H, 8.39; N, 11.66. Found: C, 80.02; H, 8.22; N, 11.10.

EXAMPLE 62

7-(3-Nitro-2-pyridylamino)-1-(1-methyl-3-piperidinyl)-naphthalene

A mixture of 7-amino-1-(1-methyl-3-piperidinyl)-naphthalene (0.252 g, 1.05 mmol from Example 61 ), 2-chloro-3-nitropyridine (0.333 g, 2.1 mmol) and collidine (0.139 mL, 1.05 mmol) in dimethylformamide (10 mL) was refluxed overnight. The reaction was concentrated at reduced pressure and the residue was taken up in methylene chloride. The organic phase was washed with 0.5N sodium hydroxide and brine, dried, concentrated onto silica gel and flash chromatographed (1×3 inches). Elution proceeded as follows: 50% ethyl acetate/hexane (500 mL) unweighed forrun; 75% ethyl acetate/hexane (400 mL) and ethyl acetate (100 mL) 0.151 g (51%) of red oil product. A sample crystallized from ether gave the title compound as red crystals. mp 107°–108° C. Analysis calculated for $C_{21}H_{22}N_4O_2$; C, 69.59; H, 6.12; N, 15.46. Found: C, 69.30; H, 5.91; N, 14.92.

EXAMPLE 63

7-(Imidazolo[4,5-b]pyridin-1-yl)1-(1-methyl-3-piperidinyl)-naphthalene

A mixture of the 7-(3-nitro-2-pyridylamino)-1-(1-methyl-3-piperidinyl)-naphthalene (0.12 g, 0.33 mmol from Example 62) and 10% palladium on carbon (0.03 g) in ethanol (10 mL) and methanol (20 mL) was hydrogenated at 50 psi for 4 hours. The reaction was filtered through celite and concentrated to the brown oil product (7-(3-amino-2-pyridylamino)-1-(1-methyl-3-piperidinyl)-naphthalene) which was suitable for use without further purification. $^1$H NMR δ 7.89–7.83 (m, 2 H), 7.78 (d, J=9 Hz, 1 H), 7.64 (dd, J =2, 9 Hz, 2 H), 7.33–7.23 (m, 2 H, partially obscurred by NMR solvent), 7.02 (dd, J=1.5, 7.5 Hz, 1 H), 6.78 (dd, J=5, 7.5 Hz, 1 H), 6.55 (br s, 1 H), 3.54 (long range coupled t, J=11.5 Hz, 1 H), 3.18 (long range coupled dd, J=1.5, 11 Hz, 1 H), 2.99 (long range coupled d, J=10.5 Hz, 1 H), 2.34 (s, 3 H), 2.17–1.97 (m, 3 H), 1.94–1.81 (sym m, 2 H), 1.69–1.51 (m, 1H). HRMS m/e calculated for $C_{21}H_{24}N_4$; m/e 332.2000. Observed m/e 332.2002.

A mixture of 7-(3-amino-2-pyridylamino)-1-(1-methyl-3-piperidinyl)-naphthalene (0.104 g, 0.313 mmol) and ethoxymethylenemalononitrile (0.056 g, 0.459 mmol) in glacial acetic acid (5 mL) was refluxed 6 hours. The reaction was cooled, neutralized with 4N sodium hydroxide and extracted with methylene chloride. The organic phase was washed with brine, dried over calcium sulfate, concentrated onto silica gel and flash chromatographed (1×2 inches). Elution proceeded as follows: 50% ethyl acetate/hexane (200 mL), 75% ethyl acetate/hexane (200 mL), ethyl acetate (200 mL) and 1% methanol/1% triethylamine/ethyl acetate (300 mL) nil; 3% methanol/3% triethylamine/ethyl acetate (300 mL) 0.075 g (70%) of 7-(imidazolo[4,5-b]pyridin-1-yl)-1-(1-methyl-3-piperidinyl)-naphthalene as a faint green oil, The product was characterized as its HCl salt which crystallized from isopropanol. mp>250° C. $^1$H NMR ($D_2O$) δ 9.30 (br s, 1 H), 8.51 (d, J=5 Hz, 1H), 8.40 (s, 1H), 8.32 (d, J=7.5 Hz, 1 H), 8.11 (d, J=9 Hz, 1 H), 7.94 (d, J=8 Hz, 1 H), 7.73 (dd, J=2, 9 Hz, 1H), 7.68–7.53 (m, 3 H), 3.77 (long range coupled t, J=11.5 Hz, 1 H), 3.62 (br t, J=10.5 Hz, 2 H), 3.22 (t, J=12.5 Hz, 1 H), 3.07 (sym m, 1 H), 2.87 (s, 3 H), 2.23–2.05 (m, 2H), 2.04–1.78 (sym m, 2 H). Analysis calculated for $C_{22}H_{22}N_4 \cdot 2HCl \cdot H_2O$: C, 60.97; H, 6.05; N, 12.93. Found: C, 60,89; H, 6.00; N, 12.61.

EXAMPLE 64

7-Benzamido-1-(1-methyl-3-piperdinyl)-naphthalene

A mixture of 7-amino-1-(1-methyl-3-piperidinyl)-naphthalene (0.203 g, 0.845 mmol, product of example 61) and triethylamine (0.141 mL, 1.01 mmol) in tetrahydrofuran (5 mL) was chilled to 0° C. and benzoyl chloride (0.118 mL, 1.01 mmol) was added. The mixture was warmed to room temperature and stirred overnight. The reaction was concentrated at reduced pressure and the residue was taken up in methylene chloride. The organic phase was extracted with 0.5N sodium hydroxide and brine, dried, concentrated onto silica gel and flash chromatographed (1×2 inches). Elution proceeded as follows: 50% ethyl acetate/hexane (225 mL), 75% ethyl acetate/hexane (150 mL) nil; 75% ethyl acetate/ hexane (400 mL) and ethyl acetate (200 mL) 0.198 g of pink foam. This product was converted to an HCl salt in methanol, treated with activated carbon, and filtered. The filtrate was concentrated and triturated with ether to give 0.091 g (31%) of the title compound as an amorphous solid with a melting range of 140°–170° C. $^1$H NMR (DMSO $d_6$) δ 10.59 (s, 1 H), 10.34 (br s, 1 H), 8.73 (s, 1H), 8.06 (d, J=7 Hz, 2 H), 7.94 (distorted t, J=10 Hz, 1H), 7.82 (d, J=7 Hz, 1H), 7.63–7.53 (m, 3 H), 7.47–7.39 (m, 2 H), 3.78 (br t, J=12 Hz, 1 H), 3.56 (br t, J=11 Hz, 2 H), 3.05 (br s, 1 H), 2.83 (br s, 3 H), 2.15–1.97 (m0 2 H), 1.71 (br s, 1 H). HRMS m/e calculated for $C_{23}H_{24}N_2O$; m/e 344.1883. Observed m/e 344.1886.

EXAMPLE 65

7-(4-Chlorobenzamido)-1-(4-methoxyethyl-1-piperazinyl)-naphthalene

A mixture of 7-(4-chlorobenzamido)-1-(1-piperazinyl)-naphthalene (0.15 g, 0.41 mmol, product of example 12), sodium iodide (0.064 g, 0.431 mmol), triethylamine (0.164 mL, 0.431 mmol) and 2-bromoethyl methyl ether (0.040 mL, 0.431 mmol) in acetonitrile (7 mL) was refluxed overnight. The reaction was cooled and concentrated at reduced pressure. The residue was taken up in methylene chloride and washed with 1N sodium hydroxide and brine, dried, concentrated onto silica gel and flash chromatographed (1×2.5 inches). Elution proceeded as follows: 50% ethyl acetate hexane (100 mL) and 75% ethyl acetate/hexane (100 mL), nil; 75% ethyl acetate/hexane (100 mL) and ethyl acetate (150 mL), 0.121 g (69%) of 7-(4-chlorobenzamido)-1-(4-methoxyethyl-1-piperazinyl)-naphthalene as an oil. This oil was converted to the HCl salt from an ether solution. An amorphous white powder hydrochloride salt of the title compound was obtained. mp 134°–148° C. $^1$H NMR δ 8.54 (br s, 1 H), 8.05 (br s, 1 H), 7.84 (long range coupled t, J=9 Hz, 3 H), 7.66 (dd, J -2, 9 Hz, 1 H), 7.55–7.43 (m, 3 H), 7.36 (t, J=8 Hz, 1 H), 7.11 (dd, J=1, 7.5 Hz, 1 H), 3.57 (t, J=5.5 Hz, 2H), 3.38 (s, 3 H), 3.19 (br s, 4 H), 2.83 (br s, 4 H), 2.70 (t, J=5.5 Hz, 2 H). Analysis calculated for $C_{24}H_{26}ClN_3O_2 \cdot 2HCl \cdot 1.5H_2O$: C, 55.02; H, 5.96; N, 8.02. Found: C, 55.53; H, 6.31; N, 7.78.

EXAMPLE 66

7-(4-Chlorobenzamido)-1-(4-propyl-1-piperazin yl)-naphthalene

A mixture of 7-(4-chlorobenzamido)-1-(1-piperazinyl)-naphthalene (0.20 g, 0.547 mmol, the product of Example 12), propionaldehyde (0.041 mL, 0.563 mmol) and sodium cyanoborohydride (0.103 g, 1.64 mmol)in methanol (12 mL) and acetic acid (1.2 mL) was stirred at ambient temperature for 20 hours. The solvent was removed at reduced pressure and the residue was partitioned between methylene chloride and saturated aqueous sodium bicarbonate. Phases were separated and the organic layer was washed with brine, dried, concentrated onto silica gel and flash chromatographed (1×3 inches). Elution proceeded as follows: ethyl acetate (50 mL) unweighed forrun; ethyl acetate (250 mL) 0.164 g of yellow foam. The foam was triturated with pentane and 0.079 g (28%) of the title compound was collected as a white solid. mp 130°–132° C. Analysis calculated for $C_{24}H_{26}ClN_3O$: C, 70.66; H, 6.42; N, 10.30. Found: C, 70.91; H, 6.66; N, 10.50.

EXAMPLE 67

7-(4-Chlorobenzamido)-1-(4-methyl-1-piperazipyl)-naphthalene

A solution of 7-(4-chlorobenzamido)-1-(1-piperazinyl)-naphthalene (0.197 g, 5.39 mmol, the product of Example 12) in tetrahydrofuran (14 mL) was chilled to −78° C. and butyllithium (0.454 mL, 1.13 mmol, 2.5 M) was added in three portions. The yellow solution was stirred 5 minutes, then ethyl iodide (0.045 mL, 0.566 mmol) was added and the reaction was allowed to warm to room temperature. The mixture was treated with saturated aqueous ammonium chloride and the solvent was removed at reduced pressure. The residue was taken up in methylene chloride and extracted with saturated aqueous sodium bicarbonate and brine, dried, concentrated onto silica gel and flash chromatographed (1×2.5 inches). Elution proceeded as follows: 75% ethyl acetate/hexane (150 mL), nil; 90% ethyl acetate/hexane (200 mL) and ethyl acetate (200 mL), 0.135 g of a light yellow foam. This foam was triturated with pentane and 0.112 g (52%) of the title compound was collected as a white powder. mp 173°–174.5° C. Analysis calculated for C$_{23}$H$_{24}$ClN$_3$O: C, 70.13; H, 6.14; N, 10.67. Found: C, 70.21; H, 6.32; N, 10.79.

EXAMPLE 68

7-Amino-1-(1-methyl-3-pyrrolidinyl)-naphthalene

A solution of 8-bromo-2-(dibenzylamino)-naphthalene (2.035 g, 5.07 mmol, preparation 4) in tetrahydrofuran (50 mL) was chilled to −78° C. and butyllithium (2.03 mL, 5.07 mmol, 2.5 M) was added dropwise. The dark solution was stirred 10 minutes, then 1-t-butoxycarbonyl-3-pyrrolidinone (0.939 g, 5.07 mmol in 4 mL tetrahydrofuran) was added dropwise with a 4 mL tetrahydrofuran rinse. The reaction was allowed to warm to room temperature and the solvent was removed. The residue was taken up in methylene chloride and washed with water, saturated aqueous ammonium chloride, saturated aqueous sodium bicarbonate, and brine. The organic phase was dried over calcium sulfate, concentrated onto silica gel and flash chromatographed (1.5×3 inches). Elution proceeded as follows: 5% ethyl acetate/hexane (700 mL), unweighed forrun; 10% ethyl acetate/hexane (200 mL), nil; 25% ethyl acetate/hexane (300 mL), 0.94 g of 7-dibenzylamino-1-(1-t-butoxycarbonyl-3-hydroxy-3-pyrrolidinyl)-naphthalene as a yellow oil which was suitable for use without further purification. A sample crystallized from ethyl acetate had mp 114°–117° C. $^1$H NMR δ 7.69 (d, J=9 Hz, 1 H), 7.63 (d, J=8 Hz, 1 H), 7.51 (d, J=2 Hz, 1 H), 7.42–7.33 (m, 8 H), 7.32–7.22 (m, 3H, partially obscured by NMR solvent), 7.21–7.06 (m, 2 H), 4.81 (t, J=21 Hz, 4 H), 3.99 (sym m, 1 H), 3.75 (sym m, 1 H), 3.58–3.35 (m, 1 H), 3.34–3.17 (m, 1 H), 2.29–2.10 (m, 1 H), 2.02–1.88 (m, 1 H), 1.90 (s, 1 H), 1.49 (s, 9 H).

A solution of 7-dibenzylamino-1-(1-t-butoxycarbonyl-3-hydroxy-3-pyrrolidinyl)-naphthalene (1.0 g, 1.97 mmol) in benzene (20 mL) was chilled on wet ice (precipitate) and Burgess salt (0.89 g, 3.74 mol) was added all at once. The mixture was heated to 55° C. for 2 hours. The reaction was cooled and extracted with water and brine. The combined aqueous phase was back extracted with ethyl acetate and the combined organic layer was dried over calcium sulfate. The organic layer was concentrated onto silica gel and flash chromatographed (1×2.5 inches). Elution with 5% ethyl acetate/hexane (1300 mL) gave 0.764 g (79%) of a brown solid which was a mixture of two dehydration products which were used directly in the next reaction.

A slurry of lithium aluminum hydride (1.78 g, 46.92 mmol) in tetrahydrofuran (220 mL) was chilled to 0° C. and the product of the above reaction (5.75 g, 11.73 mmol) was added in tetrahydrofuran (10 mL with 2×10 mL rinses). The mixture was refluxed 5 hours, chilled to 0° C. and carefully quenched with sodium sulfate decahydrate. The reaction was filtered and the filter cake was rinsed well with methylene chloride. The filtrate was concentrated at reduced pressure and the residue was taken up in methylene chloride. The organic phase was washed with brine, dried, and concentrated to give 4.58 g of a brown oil which was a 2:1 mixture of olefinic products as judged by integration of the methyl singlet at 2.48 ppm (major) and 2.31 ppm (minor) from the NMR spectrum. The mixture was used directly in the next step.

A mixture of the product of the above reaction (4.58 g) and 20% palladium hydroxide on carbon (4.7 g) in ethanol (161 mL) and acetic acid (161 mL) was hydrogenated at about 50 psi for 5.5 hours. The reaction was filtered through celite and the filtrate was concentrated at reduced pressure. The residue was neutralized with 4N sodium hydroxide and extracted with methylene chloride. The organic phase was washed with brine, dried over calcium sulfate, concentrated onto silica gel and flash chromatographed (2×3.25 inches). Elution proceeded as follows: ethyl acetate (200 mL), nil; 1% triethylamine/1% methanol/ethyl acetate (500 mL) and 2% triethylamine/2% methanol/ethyl acetate (500 mL), nil; 5% triethylamine/5% methanol/ethyl acetate (500 mL) and 10% triethylamine/10% methanol/ethyl acetate (400 mL), 0.90 g of the title compound as a brown oil. $^1$H NMR δ 7.66 (d, J=8.5 Hz, 1 H), 7.56 (d, J=8 Hz, 1 H), 7.41 (d, J=7 Hz, 1 H), 7.24 (s, 1 H, partially obscured by NMR solvent), 7.19 (t, J=7.5 Hz, 1 H), 6.94 (dd, J=2.5, 8.5 Hz, 1 H), 4.20–3.96 (m, 1 H), 3.87 (br s, 2 H), 3.08 (t, J=8.5 Hz, 1 H), 2.91–2.70 (m, 3 H), 2.45 (s, 3 H). This material was suitable for use without further purification.

EXAMPLE 69

7-Benzamido-1-(1-methyl-3-pyrrolidinyl)-naphthalene

A solution of 7-amino-1-(1-methyl-3-pyrrolidinyl)-naphthalene (0.139 g, 0.615 mmol, product of Example 68) and triethylamine (0.103 mL, 0.738 mmol) in tetrahydrofuran (5 mL) was chilled to 0° C. and benzoyl chloride (0.086 mL, 0.738 mmol) was added. The reaction was warmed to room temperature and stirred overnight. The solvent was removed at reduced pressure and the residue was taken up in methylene chloride. The organic layer was washed with 0.5N sodium hydroxide and brine, dried, concentrated onto silica gel and flash chromatographed (1×2 inches). Elution proceeded as follows: 50% to 75% ethyl acetate/hexane (375 mL), nil; ethyl acetate (200 mL), nil; 2% triethylamine/2% methanol/ethyl acetate (200 mL), 0.14 g of brown oil which partially crystallized. Recrystallization from ethyl acetate gave 0.058 g, (28%) of the title compound as white crystals. mp 137°–145° C.; $^1$H NMR δ 8.57 (d, J=2 Hz, 1 H), 8.06 (br s, 1 H), 7.95 (dd, J=1.5, 8 Hz, 2 H), 7.86 (d, J=9 Hz, 1 H), 7.71–7.64 (m, 2 H), 7.59–7.49 (m, 4 H), 7.40 (t, J=7.5 Hz, 1 H), 4.15 (sym m, 1 H), 3.04 (t, J=9 Hz, 1 H), 2.93–2.81 (m, 2 H), 2.80–2.68 (m, 1 H), 2.66–2.50 (m, 1 H), 2.47 (s, 3H), 2.08–1.96 (m, 1 H). Analysis calculated for C$_{22}$H22N2O: C, 79.97; H, 6.71; N, 8.48. Found: C, 79.36; H, 6.72; N, 7.94.

EXAMPLE 70

7-Amino-1-(1-t-butoxycarbonyl-pyrrolidin-2-(R)-ylmethyl)-naphthalene

A solution of 8-bromo-2-(dibenzylamino)-naphthalene (5.0 g, 12.0 mmol, preparation 4) in tetrahydrofuran (300 mL) was chilled to −78° C. and butyllithium (5.0 mL, 12.5 mmol, 2.5 M) was added dropwise to generate a dark red solution. A tetrahydrofuran solution (40 mL) of 1-t-butoxycarbonyl-R-prolinal (2.61 g, 13 mmol) was added dropwise with a 10 mL tetrahydrofuran rinse. The reaction was stirred an additional 10 minutes, then carbon disulfide (0.95 mL, 16 mmol, predried over calcium sulfate) was added. The reaction color changed from green to brown and finally to orange. After stirring 30 minutes at −78° C., methyl iodide (0.82 mL, 13 mmol) was added and the reaction was allowed to warm to ambient temperature and stir 2 hours. Aqueous ammonium chloride and ether were added and the phases were separated. The organic layer was washed with water and brine, dried over magnesium sulfate, concentrated onto silica gel and flash chromatographed (2×6 inches). Elution proceeded as follows: 2% ether/hexane (1 L), unweighed impurity; 5% ether/hexane (1000 mL), 10% ether/hexane (1000 mL), and 20% ether/hexane (1000 mL), 5.74 g (78%) of the xanthate intermediate as a mixture of diastereomers which was used directly in the next step.

A solution of the xanthate from the above reaction (5.74 g, 9.37 mmol) in toluene (300 mL) was heated to reflux and AIBN (0.26 g) (AIBN=azo(bis) isobutyronitrile) and tributyltin hydride (11.7 mL, 43.5 mmol) were added in three portions first at initial reflux and then after 1 and 2 hours of reflux. The reaction was refluxed an additional 1.5 hours, cooled to room temperature and allowed to stir overnight. The reaction was concentrated onto silica gel and flash chromatographed (2×8 inches). Elution proceeded as follows: hexane (1000 mL), unweighed tin impurities; 2% ether/hexane (2 L) and 3% ether/hexane (2 L), unweighed impurities; 5% ether/hexane (3 L), 3.07 g (65%) of 7-dibenzylamino-1-(1-t-butoxycarbonyl-pyrrolidin-2-(R)-ylmethyl)- naphthalene as a hard yellow-green foam.

A mixture of 7-dibenzylamino-1-(1-t-butoxycarbonyl-pyrrolidin-2-(R)-ylmethyl)-naphthalene (0.68 g, 1.34 mmol) and 20% palladium hydroxide on carbon (0.25 g) in ethanol (20 mL) and acetic acid (20 mL) was hydrogenated at 50 psi for 8 hours. Additional 20% palladium hydroxide on carbon (0.25 g) was added and hydrogenation was continued overnight. The catalyst (0.3 g) was added a third time and hydrogenation was continued 24 hours more. The reaction was filtered through celite and the pad was washed with ethanol. The filtrate was concentrated and the residue was taken up in ether. This organic phase was extracted with saturated aqueous sodium bicarbonate, water and brine, then it was dried and concentrated to give 0.368 g (84%) of the title compound as a tan foam. A sample recrystallized from ether/hexane as a light tan solid had mp 157°–158.5° C. Analysis calculated for $C_{20}H_{26}N_2O_2$: C, 73.59; H, 8.03; N, 8.58. Found: C, 73.47; H, 7.93; N, 8.37.

The S enantiomer of the title compound of Example 70 was prepared using the same procedure set forth in Example 70, except that 1-t-butoxycarbonyl-(S)-prolinal was used in place of 1-t-butoxycarbonyl-(R)-prolinal.

EXAMPLE 71

7-(4-Chlorobenzamido)-1-(pyrrolidin-2-(R)-ylmethyl)-naphthalene

A solution of 7-amino-1-(1-t-butoxycarbonyl-pyrrolidin-2-(R)-ylmethyl)-naphthalene (0.10 g, 0.306 mmol, product of Example 70) and triethylamine (0.085 mL, 6.1 mmol) in tetrahydrofuran (5 mL) was chilled to 0° C. and 4-chlorobenzoyl chloride (0.043 mL, 0.338 mmol) was added. The mixture was allowed to warm to room temperature and stir 2 hours. Ether was added and the reaction was extracted with saturated aqueous sodium bicarbonate, water, and brine. The organic phase was concentrated onto silica gel and flash chromatographed (1×6 inches). Elution proceeded as follows: 20% ether/hexane, unweighed forrun; 30% ether/hexane (200 mL) 0.096 g (68%) of 7-(4-chlorobenzamido)-1-(1-t-butoxycarbonyl-pyrrolidin-2-(R)-ylmethyl)-naphthalene as a white powder. A sample recrystallized from ether/hexane had mp 136.5°–137° C.; $[\alpha]_D$ =−75.4°, c=0.195 (chloroform). Analysis calculated for $C_{27}H_{29}ClN_2O_3$: C, 69.74; H, 6.29; N, 6.02. Found: C, 69.75; H, 6.00; N, 6.00.

To a solution of 7-(4-chlorobenzamido)-1-(1-t-butoxycarbonyl-pyrrolidin-2-(R)-ylmethyl)-naphthalene ((0.09 g, 0.19 mmol)in ether (10 mL) was added ether saturated with gaseous hydrogen chloride (27 mL) in portions over several hours. The mixture was stirred overnight and concentrated. The residue was triturated with ether and 0.063 g (80%) of the title compound was collected as a faint pink solid salt. mp 230°–231.5° C.; $[\alpha]_D$=−46.8°, c=0.280 (methanol). Analysis calculated for $C_{22}H_{21}ClN_2O \cdot HCl \cdot 0.5\ H_2O$: C, 64.39; H, 5.90; N, 6.83. Found: C, 64.49; H, 5.38; N, 6.70.

The S enantiomer of the title compound of example 71 was prepared using the same procedure set forth in Example 71, except that 7-amino-1-(1-t-butoxycarbonylpyrrolidin-2-(S)-ylmethyl)-naphthalene was used in place of 7-(4-chlorobenzamido)-1-(1-t-butoxycarbonyl-pyrrolidin-2-(R)-ylmethyl)-naphthalene.

EXAMPLE 72

7-Formamido-1-(pyrrolidin-2-(R)-ylmethyl)-naphthalene hydrochloride

A mixture of 7-amino-1-(1-t-butoxycarbonyl-pyrrolidin-2-(R)-ylmethyl)-naphthalene (0.096 g, 0.294 mmol, product of example 70), triethylamine (0.055 mL, 0.395 mmol) and acetyl formyl anhydride (0.050 mL, 0.373 mmol) in tetrahydrofuran (5 mL) was refluxed 2 hours. Additional acetyl formyl anhydride (0.020 mL) was added and the reaction was stirred 1 hour more. The reaction was diluted with ether and extracted with water and brine. The organic phase was dried, concentrated, and flash chromatographed on silica gel (1×4 inches). Elution proceeded as follows: 10% ethyl acetate/hexane (100 mL), nil; 20% ethyl acetate/hexane (350 mL), nil; 25% ethyl acetate/hexane (750 mL), 0.076 g (73%) of 7-formamido-1-(1-t-butoxycarbonyl-pyrrolidin-2-(R)-ylmethyl)-naphthalene as a pale pink oil.

The oil from the above reaction (0.076 g, 0.214 mmol) was dissolved in ether and ether saturated with hydrogen chloride (10 mL) was added in 2 mL portions over 1 hour. The mixture was stirred overnight at ambient temperature. The mixture was concentrated under a nitrogen stream and the residue was slurried in ether (20 mL). The slurry was gently refluxed 1 hour and the material was triturated to yield the title compound as a light tan powder. mp 223.5°–224° C.; $[\alpha]_D$=−51.5°, c=0.295 (methanol). Analysis calculated for $C_{16}H_{18}N_2O \cdot HCl \cdot 1.5\ H_2O$: C, 60.47; H, 6.98; N, 8.81. Found: C, 60.65; H, 6.69; N, 8.72.

EXAMPLE 73

7-Amino-1-(1-piperazinyl)-naphthalene

The product of Example 11 (7-benzamido-1-(1-piperazinyl)-naphthalene, (0.063 g, 0.19 mmol) was combined with hydrochloric acid in ethanol (4 mL) and refluxed 16 hours. The reaction was concentrated at reduced pressure and the residue was neutralized with 4 N sodium hydroxide and extracted with methylene chloride. The organic phase was washed with brine, dried and concentrated to a tan solid (0.041 g). The solid was recrystallized from ethyl acetate/hexane to give 0.020 g (47%) of the title compound as light tan crystals. mp 184°–186° C. HRMS m/e calculated for $C_{14}H_{17}N_3$: 227.1419. Observed m/e 227.1405.

EXAMPLE 74

7-(Imidazolo-[4,5-b]-pyridin-1-yl)-1-(1-piperazinyl)-naphthalene

A two phase mixture of methylene chloride (50 mL) and water (100 mL) containing 7-amino-1-(1-piperazinyl)-naphthalene (5.05 g, 22.23 mmol) and sodium carbonate (2.36 g, 22.23 mmol) was treated with di-tert-butyl dicarbonate (4.85 g, 22.23 mmol, in 40 mL methylene chloride) dropwise with a 10 mL methylene chloride rinse. The reaction was stirred overnight, then the phases were separated. The organic layer was washed with brine, dried, concentrated onto silica gel and flash chromatographed (1.5×3.5 inches). Elution proceeded as follows: 10% ethyl acetate/hexane (700 mL), 1.62 g of 7-tert-butoxycarbonylamino-1-(4-tert-butoxycarbonyl-1-piperazinyl)-naphthalene as a yellow foam; 10% ethyl acetate/hexane (200 mL) and 30% ethyl acetate/hexane (500 mL), 4.18 g of 7-amino-1-(4-tert-butoxycarbonyl-1-piperazinyl)-naphthalene as a brown foam which had $^1$H NMR δ 7.67 (d, J=8.5 Hz, 1 H), 7.46 (d, J=8 Hz, 1 H), 7.35 (d, J=2.5 Hz, 1 H), 7.17 (t, J=7.5 Hz, 1 H), 7.01 (dd, J=1, 7.5 Hz, 1 H), 6.95 (dd, J=2.5, 8.5 Hz, 1 H), 3.90 (br s, 2 H), 3.05 (br s, 8 H), 1.51 (s, 9 H).

A mixture of 7-amino-1-(4-tert-butoxycarbonyl-1-piperazinyl)-naphthalene (0.523 g, 1.60 mmol, product of the above reaction), 2-chloro-3-nitropyridine-N-oxide (0.335 g, 1.92 mmol, product of preparation 5) and 4-dimethylaminopyridine (0.195 g, 1.60 mmol) in ethanol (40 mL) was refluxed 2 hours. The solvent was removed at reduced pressure and the residue was taken up in methylene chloride. The organic solution was washed with saturated aqueous sodium bicarbonate and brine and the aqueous washes were back extracted (5x) with methylene chloride. The combined organic phase was dried, concentrated onto silica gel and flash chromatographed (1×3 inches). Elution proceeded as follows: 50% ethyl acetate/hexane (200 mL) and 75% ethyl acetate/hexane (200 mL), nil; 70% ethyl acetate/hexane (100 mL) and ethyl acetate (300 mL), 0.458 g (61%) of 7-(3-nitro-1-oxido-2-pyridylamino)-1-(4-tert-butoxycarbonyl-1-piperazinyl)-naphthalene as a dark red foam which was suitable for use without further purification. A sample recrystallized from ether/hexane as orange crystals had mp 191°–193° C. Analysis calculated for $C_{24}H_{27}N_5O_5$: C, 61.92; H, 5.85; N, 15.04. Found: C, 61.59; H, 5.79; N, 14.54.

A mixture of 7-(3-nitro-1-oxido-2-pyridylamino)-1-(4-tert-butoxycarbonyl-1-piperazinyl)-naphthalene (0.40 g, 0.86 mmol, product of the above reaction), ammonium formate (1.0 g, 17.2 mmol), and 10% palladium on carbon (0.15 g) in ethanol (30 mL) was refluxed 4 hour while continually returning sublimed ammonium formate back into the reaction. The solvent was removed at reduced pressure and the residue was taken up in methylene chloride. The organic solution was washed with water and brine, dried over calcium sulfate, and concentrated. The residue was flash chromatographed on silica gel (1×3 inches), Elution proceeded as follows: 25% ethyl acetate/hexane (100 mL), nil; 35% ethyl acetate/hexane (250 mL), 0.25 g of product. The product was treated with activated carbon, filtered, and concentrated. The residue was recrystallized from ethyl acetate/ether to give 0.11 g (30%) of 7-(3-amino-2-pyridylamino)-1-(4-tert-butoxycarbonyl-1-piperazinyl)-naphthalene as white crystals which were sensitive to air (turn brown on air exposure) and had mp 183°–184° C. Analysis calculated for $C_{24}H_{29}N_5O_2$: C, 68.71; H, 6.97; N, 16.69. Found: C, 68.76; H, 6.58; N, 16.56.

A mixture of 7-(3-amino-2-pyridylamino)-1-(4-tert-butoxycarbonyl-1-piperazinyl)-naphthalene (0.124 g, 0.296 mmol, product of the above reaction) and ethoxymethylenemalononitrile (0.47 g, 0.385 mmol) in isopropanol (7 mL) was refluxed 4 hour. Additional ethoxymethylenemalononitrile (0.035 g) was added and the reaction was refluxed overnight. The reaction was concentrated onto silica gel and flash chromatographed (1×3.5 inches). Elution proceeded as follows: 10% ethyl acetate/hexane (400 mL), nil; 20% ethyl acetate/hexane (300 mL), unweighed isopropoxymethylenemalononitrile; 20% ethyl acetate/hexane (50 mL) and 40% ethyl acetate/hexane (300 mL), 0.082 g (65%) of 7-(imidazolo-[4,5-b]-pyridin-1-yl)-1-(4-tert-butoxycarbonyl-1-piperazinyl)-naphthalene as a tan oily foam which was suitable for use as obtained which had $^1$H NMR δ 8.76 (d, J=2 Hz, 1 H), 8.51–8.48 (m, 2 H), 8.20 (dd, J=1.5, 8 Hz, 1 H), 8.04 (d, J=9 Hz, 1 H), 7.84 (dd, J=5, 8 Hz, 1 H), 7.65 (d, J=8 Hz, 1 H), 7.49 (t, J=8 Hz, 1 H), 7.36 (d, J=5, 8 Hz, 1 H), 7.17 (d, J=7.5 Hz, 1 H), 4.20–3.30 (br coelesced signal, 4 H), 3.16 (br s, 4 H), 1.51 (s, 9 H).

A solution of 7-(imidazolo-[4,5-b]-pyridin-1-yl)-1-(4-tert-butoxycarbonyl-1-piperazinyl)-naphthalene (0.076 g, 0.177 mmol) in ethanol (6 mL) was treated with hydrogen chloride saturated dioxane (4 mL). The mixture was stirred 10 hours at room temperature and a fine precipitate formed. The solvent was removed at reduced pressure and the residue was dissolved in hot methanol and filtered. The filtrate was concentrated to about 4 mL at the boil and treated with ethanol (3 mL). The white crystals obtained on cooling were collected and washed with cold ethanol to give 0.022 g (33%) of the dihydrochloride of the title compound. mp >250° C. Analysis calculated for $C_{20}H_{19}N_5$·2 HCl: C, 59.71; H, 5.26; N, 17.41. Found: C, 59.72; H, 5.29; N, 16.62.

EXAMPLE 75

7-(1,2,3-Triazolo-[4,5-b]-pyridin-1-yl)-1-(1-piperazinyl)-naphthalene

A mixture of 7-(3-amino-2-pyridylamino)-I-(4-tert-butoxycarbonyl-1-piperazinyl)-naphthalene (0.038 g, 0.0906 mmol, intermediate of example 74) in 5% sulfuric acid (1.5 mL, precooled to 0° C) was treated with sodium nitrite (0.0066 g, 0.095 mmol) in water (0.1 mL) with a water rinse (2×0.1 mL). The heterogeneous mixture was stirred 40 minutes at 0° C. The reaction was diluted with ice and neutralized with 1N sodium hydroxide. The reaction was extracted with methylene chloride and this organic phase was washed with saturated aqueous sodium bicarbonate and brine, dried, and concentrated to yield 7-(1,2,3-triazolo-[4,5-b]-pyridin-1-yl)-1-(4-tert-butoxycarbonyl-1-piperazinyl)-naphthalene as a brown oil (0.034 g, 87%) which was suitable for use without purification. A sample treated with activated carbon in methylene chloride and then recrystallized from ether/hexane had mp 173°–175° C. Analysis calculated for $C_{24}H_{26}N_6O_2$: C, 66.96; H, 6.09; N, 19.52. Found: C, 66.61; H, 6.18; N, 19.28.

A solution of 7-(1,2,3-triazolo-[4,5-b]-pyridin-1-yl)-1-(4-tert-butoxycarbonyl-1-piperazinyl)naphthalene (0.075 g, 0.174 mmol, product of the above reaction) in ethanol (4 mL) was treated with hydrogen chloride saturated dioxane (4 mL) and the mixture was stirred at room temperature 10 hours. The solvent was removed at reduced pressure and the residue was dissolved in hot methanol. The methanol solution was filtered hot and the filtrate was concentrated at the boil to about 1 mL. Yellow crystals formed on cooling. These crystals were collected to give 0.031 g (48%) of the hydrochloride the title compound. mp >250° C. Analysis calculated for $C_{19}H_{18}N_6$·HCl: C, 62.21; H, 5.22; N, 22.91. Found: C, 62.11; H, 5.11; N, 22.53.

EXAMPLE 76

1-(4-Methylpiperazin-1-yl)-7-(pyrimid-5-yl)naphthalene

A mixture of 7-trifluoromethylsulfonyloxy-1-(4-methylpiperazin-1-yl)naphthalene (0.250 g, 0.67 mmol), bis-(triphenylphosphine)palladium[11]chloride (0.025 g, 0.036 mmol), 5-trimethylstannylpyrimidine (0.178 g, 0.74 mmol, from Preparation 6), triethylamine (0.45 mL, 3.23 mmol), lithium chloride (0.088 g, 2.07 mmol), 2,6-di-tert-butyl-4-methylphenol (approximately 0.01 g), and N, N-dimethylformamide (12.5 mL) was heated between 100° C. to 115° C. under nitrogen for 45 minutes. The resulting mixture was concentrated via evaporation under reduced pressure, and the residue was column chromatographed using silica gel (approximately 25 g) and elution with 9:1:0.1 [methylene chloride/methanol/ammonium hydroxide] to afford the title compound (0.060 g, 0.20 mmol, 29%) as a pale yellow foam: $R_f$=0.15 in 20% methanol in ethyl acetate; $^{13}$C NMR (CDCl$_3$) δ 157.3, 155.0, 149.8, 134.6, 134.5, 130.8, 129.9, 129.0, 127.1, 124.0, 123.4, 122.1, 116.0, 55.4, 52.7, 45.9; LRMS (m/z, relative intensity) 304 (M$^+$, 7), 240 (100), 225 (15), 196 (16), 169 (44), 155 (33), 141 (16); HRMS m/e calculated for C$_{19}$H$_{20}$N$_4$ 304.1690. Observed m/e 304.1689.

EXAMPLE 77

7-(5-Cyanopyrid-3-yl)-1-(4-methylpiperazin-1-yl)naphthalene

A mixture of 7-trifluoromethylsulfonyloxy-1-(4-methylpiperazin-1-yl)naphthalene (0.527 g, 1.53 mmol), bis-(triphenylphosphine)palladium[II]chloride (0.537 g, 0.77 mmol), 5-cyano-3-trimethylstannylpyridine (0.0.450 g, 1.69 mmol, from preparation 7), triethylamine (1.02 mL, 7.34 mmol), lithium chloride (0.194 g, 4.59 mmol), 2,6-di-tert-butyl-4-methylphenol (approximately 0.01 g), and N,N-dimethylformamide (6 mL) was heated between 100° C. to 115° C. under nitrogen for 1.5 hours. The resulting mixture was concentrated via evaporation under reduced pressure, and the residue was column chromatographed using silica gel (approximately 25 g) and elution with 5% methanol in ethyl acetate to afford the title compound (0.170 g, 0.52 mmol, 34%) as a pale yellow foam: $R_f$=0.40 in 5% methanol in ethyl acetate; $^1$H (CD$_3$OD) δ 9.08 (d, J=2.2 Hz, 1H), 8.82 (d, J=2.2 Hz, 1H), 8.43 (t, J=2.0 Hz, 1H), 8.36 (br s, 1H), 7.92 (d, J=8.5 Hz, 1H), 7.70 (dd, J=1.8 and 8.5 Hz, 1H), 7.57 (br d, J=8.2 Hz, 1H), 7.44 (t, J=7.8 Hz, 1H), 7.17 (d, J=7.3 Hz, 1H), 3.20–3.00 (br s, 4H), 2.85–2.65 (br s, 4H), 2.40 (s, 3H); LRMS (m/z, relative intensity) 328 (M$^+$, 100); HRMS m/e calculated for C$_{21}$H$_{20}$N$_4$ 328.1690. Observed m/e 328.1715

EXAMPLE 78

General procedure for the synthesis of (1-piperazinyl)naphthyl-7-yl ethers.

To a flame dried round bottom flask was added 7-hydroxy-1-(4-methyl-1-piperazinyl)naphthalene (0.30 g, 1.23 mmol), anhydrous N,N-dimethylformamide (3 mL), and 60% dispersion of sodium hydride in mineral oil (0.060 g; 1.47 mmol, 1.2 eq). The resulting suspension was heated for twenty minutes at 40° C., and the resulting reaction mixture was then allowed to cool to room temperature. A suspension of the appropriate alkylating agent or appropriate electrophile (1.35 mmol, 1.1 eq), anhydrous DMF (1 mL) and 60% sodium hydride (0.075 grams 0.00183 moles) was then added slowly over 30 minutes in three portions to the reaction mixture, and the resulting mixture was heated at 80° C. The progress of the reaction was monitored by TLC, and reaction completion was determined by consumption of 7-hydroxy-1-(4-methyl-1-piperazinyl)naphthalene as determined by TLC. Upon determination of reaction completion, DMF was then removed in vacuo, and the residue was partitioned between methylene chloride (40 mL) and saturated sodium bicarbonate solution (40 mL). The organic layer was removed, dried (Na$_2$SO$_4$), and concentrated in vacuo. The resulting residue was purified by flash column chromatography using silica gel (15 grams) and elution with 12:1:0.04 [CH$_2$Cl$_2$: methanol: NH$_4$OH] to afford the title compound.

Using the above general procedure, the following compounds were prepared:

A. 2-[8-(Methylpiperazin-1-yl)napthalen-2-yloxy]nicotinonitrile

2-Chloro-3-cyanopyridine was the electrophile. Chromatography afforded the title compound (33%) as an amorphous solid: HRMS m/e calculated for C$_{21}$H$_{20}$N$_4$O 344.1637. Observed m/e 344.1618; $^{13}$C NMR (CDCl$_3$) δ 46.2, 52.9, 55.6, 97.7, 114.6, 115.0, 115.7, 118.1, 121.1, 123.4, 125.8, 129.9, 130.1, 132.7, 143.5, 149.6, 150.0, 151.5, 163.9.

EXAMPLE 79

8-(4-Methylpiperazin-1-yl) naphthalene-2-carboxylic acid phenylamide

To a flame dried 3-neck flask were added 7-trifluoromethylsulfonyloxy-1-(4-methylpiperazin-1-yl)naphthalene (0.95g, 2.54 mmol), aniline (0.35 mL, 3.81 mmol), and triethylamine (0.39 mL, 2.79 mmol). A balloon of carbon monoxide provided a CO atmosphere above the reaction mixture via the reflux condenser. The reaction contents were heated at 100° C. for ten minutes. The solution was then cooled to 70° C., and bis(triphenylphosphine)palladium(11) chloride (0.036 g, 0.05 mmol, 2 mol%) was added to the reaction solution. The resulting reaction mixture was stirred at 100° C. for 19 hours. Then the CO balloon was refilled with CO, additional triethylamine (approx. 0.5 mL) was added, and this mixture was stirred at 100° C. for 5 hours. Ethyl acetate (25 mL) was added to the cooled reaction mixture, and this mixture was then filtered through Celite®. The filtrate was concentrated in vacuo. The residue was purified using flash column chromatography using silica gel (30 g) and elution with 5% methanol in ethyl acetate to afford the title compound (0.090 g, 10%) as an amorphous solid: $R_f$=0.42 in 9:1:0.1 methylene chloride/methanol/ammonium hydroxide; HRMS m/e calculated for C$_{22}$H$_{23}$N$_3$O 345.1843. Observed m/e 345.1873; $^{13}$C NMR (CDCl$_3$) δ 46.0, 52.9, 55.4, 115.9, 120.3, 123.2, 123.3, 123.7, 124.6, 128.0, 128.1; 129.1, 131.5, 136.2, 138.1, 150.5, 167.0.

EXAMPLE 80

8-(4-Methylpiperazin-1-yl) naphthalene-2-carboxylic acid 4-chlorobenzylamide

A mixture of 7-trifluoromethylsulfonyloxy-1-(4-methylpiperazin-1-yl)naphthalene (9.0 g, 24 mmol), bis (triphenylphosphine) palladium chloride (0.36 g, 0.51 mmol) and methanol (90 mL) was warmed to 60° C. under a balloon of carbon monoxide for 96 hours. The reaction was cooled to room temperature and charged with additional catalyst (0.28g, 0.396 mmol). The mixture was again placed under a carbon monoxide atmosphere and refluxed 40 hours. The reaction was cooled filtered and concentrated to a brown oil. This residue was flash chromatographed on silica gel (300 g). Elution was 30:1:0.03 ethyl acetate, methanol, ammonium hydroxide to afford 2.7 g (39.5%) of methyl 8-(4-methylpiperazin-1-yl) naphthalene-2-carboxylate as a light yellow solid: tlc: $R_f$=0.32 (10: 0.5: 0.05, ethyl acetate, methanol, ammonium hydroxide), $^{13}$C NMR δ 167.36, 150.32, 136.85, 128.64, 128.39, 127.83, 126.58, 125.89, 125.19, 123.37, 115.57, 55.22, 52.33, 52.17, 45.54, HRMS m/e calculated for C$_{17}$H$_{20}$N$_2$O$_2$: 284.152. Observed m/e: 284.1513.

A mixture of the above ester (1.56 g, 5.48 mmol), methanol (50 mL) and lithium hydroxide (1.15 g, 27.4 mmol) was refluxed 22 hours. The reaction was concentrated and the residual solid was treated with hydrochloric acid in dioxane (32.9 mL, 32.9 mmol, 1N). Water (3 mL) was added to yield a clear solution which was concentrated in vacuo to afford 8-(4-methylpiperazin-1-yl)naphthalene-2-carboxylic acid hydrochloride as a solid which also contained lithium hydrochloride. This material was used without purification and assumed to be a quantitative yield reaction. HRMS m/e calculated for $C_{16}H_{18}N_2O_2$: 270.1370. Observed m/e: 270.1360.

A mixture of the above acid (0.25 g, 0.82 mmol), methylene chloride (4 mL), N-methylmorpholine (0.31 mL, 2.87 mmol), 1-hydroxy benzotriazole hydrate (0.12 g, 0.9 mmol), 4-chlorobenzylamine (0.1 mL, 0.82 mmol) and 1-cyclohexyl-3-(7-morpholinoethyl) carbodiimide p-toluenesulfonate (0.69 g, 1.62 mmol) was stirred 17 hours at ambient temperature. The reaction was diluted with water (10 mL) and methylene chloride (10 mL) and adjusted to pH 9 by addition of saturated aqueous sodium carbonate. The phases were separated and the organic layer was dried over sodium sulfate and concentrated to a yellow solid. This material was purified by flash chromatography on silicon gel (6 g). Elution with 12: 1: 0.04, methylene chloride, methanol, ammonium hydroxide gave 0.07 g (21.8%) of the title compound as a solid: mp 72°–74° C.; tlc: $R_f$=0.28 (12: 1: 0.04, methylene chloride, methanol, ammonium hydroxide); $^{13}$C NMR δ 168.04, 150.69, 137.09, 136.16, 133.17, 130.82, 129.01, 128.90, 128.77, 128.18, 127.91, 123.84, 123.30, 123.07, 115.61, 55.47, 53.10, 46.13, 43.34. HRMS m/e calculated for $C_{23}H_{24}ClN_3O$: 393.1607. Observed m/e: 393.1642.

EXAMPLE 81

7-(3-Methoxyphenyl)-1-(4-methylpiperazin-1-yl)naphthalene

A mixture of 3-methoxy-1-bromobenzene (0.089 mL, 0.71 mmol), 7-trimethylstannyl-1-(4-methylpiperazin-1-yl) naphthalene (0.25 g, 0.64 mmol), bis(acetonitrile) palladium chloride (0.0085 g, 0.032 mmol), tri(3-methoxyphenyl)phosphine (0.023 g, 0.064 mmol), and butylated hydroxytoluene (BHT, about 0.001 g, antioxidant) in dimethyl formamide (12 mL) was warned to 110° C. for 2 hours. The reaction was cooled to room temperature and diluted with 1N aqueous lithium chloride (25 mL) and 1 N sodium hydroxide (2 mL); then extracted with ether (3X). The combined ether layer was washed with 1N aqueous lithium chloride and brine. The organic phase was dried over calcium sulfate and concentrated. The residue was purified by flash chromatography on silica gel (1×2.5 inches). Elution proceeded as follows: 75% ethyl acetate/hexane, 200 mL, nil; 2% methanol/ethyl acetate 200 mL and 10% methanol/ ethyl acetate, 200 mL, 0.084 g of an oil. This oil was further purified by kugelrohr distillation (1 mm Hg). The distillation proceeded as follows: 110°–130° C., 0.014 g of a mixture of the title product and 7-methyl-1-(4-methylpiperazin-1-yl) naphthalene: 200°–220° C., 0.062 g (23%) of the title compound as a yellow oil: $^1$H NMR δ 8.43 (incompletely resolved dd, J=1.2Hz, 1 h), 7.90 (d, J=9 Hz, 1 H), 7.74 (dd, J=2, 8.5 Hz, 1 H), 7.58 (d, J=8 Hz, 1 H), 7.43 (sym m, 2 H), 7.34 (dt, J=1.5, 7.5 Hz, 1 H), 7.29 (S, J=2 Hz, 1 H), 7.14 (dd, J=1, 7.5 Hz, 1 H), 6.96 (ddd, J=1,2.5, 8 Hz, 1H), 3.92 (s, 3 H) 3.20 (br s, 4 H), 2.75 (br s, 4 H), 2.44 (s, 3 H). The product was dissolved in chloroform and HCl gas was bubbled through the solution to form the hydrochloride salt. Concentration of this solution to about 1 mL. at the boil and addition of about 1 mL of ether caused the white crystalline product to precipitate. The hydrochloride salt weighted 0.057 g: mp 236°–238° C. Analysis calculated for $C_{22}H_{24}N_2O \cdot HCl$: C, 71.63; H, 6.83; N, 7.59. Found: C, 71.31; H, 6.92; N, 7.59.

EXAMPLE 82

1-(1-Methylpiperidin-4-yl)-7-naphthalene carboxylic acid 4-chlorobenzylamide

A mixture of 1-(1-methylpiperidin-4-yl)-7-trifluoromethylsulfonyloxynaphthalene (1.0 g, 2.69 mmol), 4-chlorobenzylamine (0.59 mL, 4.84 mmol) and bis (triphenylphosphine)palladium chloride (0.095 g, 0.13 mmol), and triethylamine (0.56 mL, 4.04 mmol) was blanketed with an atmosphere of carbon monoxide (with the aid of a balloon) and heated to 110°–120° C. for 2 hours. Additional 4-chlorobenzylamine (0.2 mL) was added and the reaction was heated under carbon monoxide for 17 hours more. The reaction was cooled to room temperature and taken up in ethyl acetate. The mixture was extracted with water and brine, dried over calcium sulfate, and concentrated. The residue was flash chromatographed on silica gel (1.5×2.5 inches). Elution proceeded as follows: ethyl acetate, 350 mL, nil; 2% methanol/ethyl acetate, 300 mL, nil; 4% methanol/1% triethylamine/ethyl acetate, 200 mL, 0.085 g of impure product. Continued elution with 4% methanol/1% triethylamine/ethyl acetate, 200 mL, 0.266 g (25%) of the title compound as a yellow oil. $^1$H NMR (DMSO$_{d6}$) δ 8.74 (s, 1H), 7.90 (d, J=8.5 Hz, 1H), 7.73 (dt, J=1.5, 8.5 Hz, 2H), 7.58–7.48 (m, 2H), 7.35 (s, 4H), 6.63 (br t, J=6 Hz, 1H), 4.70 (d, J=6 Hz, 2H), 3.42 (quintuplet, J=8 Hz, 1H), 3.05 (br d, J=12 Hz, 2H), 2.38 (s, 3H), 2.23 (sym m, 2H), 1.99–1.92 (m, 4H). HRMS m/e calculated for $C_{24}H_{25}C_1N_2O$: 393.1733. Observed m/e: 393.1747.

Synthesis of intermediates used in the above Examples are described in the preparations below.

PREPARATION 1

7-hydroxy-1-(4-methyl-1-piperazinyl)-3,4-dihydronaphthalene

7-Hydroxy-α-tetralone (1.0 g, 6.17 mmol, Corey and Estreicher, Tetrahedron Lett., 1981,22,603) and 1-methylpiperazine (2.2 mL, 19.83 mmol) were dissolved in dry THF (90 mL) and chilled to 0° C. Titanium tetrachloride (0.91 mL, 8.3 mmol) was allowed to run down the side of the reaction vessel into the reaction via syringe to give a vigorous reaction which caused the solution to turn orange-red. The mixture was allowed to warm to ambient temperature and stir 1.5 hours. A 2:1 mixture of water and concentrated ammonium hydroxide (90 mL) was added and the mixture was extracted with ethyl acetate. The organic phase was dried over calcium sulfate and concentrated to give 1.48 g of crude enamine which was used immediately without characterization. (This enamine was not stable to chromatography but did show a characteristic signal in the $^1$H NMR for the enamine vinyl proton at 5.28 ppm with a 4.7 Hz coupling constant).

PREPARATION 2

7-Hydroxy-1-(4-methyl-1-piperazinyl)-naphthalene

10% Palladium on carbon (1.16 g) and 7-hydroxy-1-(4-methyl-1-piperazinyl)-2,3-dihydronaphthalene (1.48 g, 6.06 mmol) were slurried in toluene (100 mL) and refluxed 16.5 h. The mixture was cooled, filtered, and concentrated. The product was purified by flash chromatography on silica gel (1×6 inches). Elution with 50% ethyl acetate/hexane followed by 100% ethyl acetate gave 0.51 g (34%) of the title product as a light pink foam. A sample was recrystallized from ether to give a cream colored solid for analysis: mp 184°–185° C. Analysis calculated for $C_{15}H_{18}N_2O$: C, 74.35; H, 7.49; N, 11.56. Found: C, 74.05; H, 7.03; N, 11.42.

PREPARATION 3

7-Trimethylstannyl-1-(4-methyl-1-piperazinyl)-naphthalene 7-trifluoromethylsulfonyloxy-1-(4-methyl-1-piperazinyl)-naphthalene (2.0 g, 5.34 mmol), hexamethylditin (1.92 g, 5.86 mmol), lithium chloride (0.68 g, 16 mmol), tetra (triphenylphosphine) palladium (0.24 g, 0.21 mmol) and butylated hydroxytoluene (a few crystals, antioxidant) were combined in dry dioxane (50 mL) and refluxed 45 minutes. The mixture was cooled and quenched with saturated ammonium chloride (50 mL). The mixture was extracted with ether (2x) and the combined organic phase was washed with brine, dried over magnesium sulfate, and concentrated to a brown oil. Flash chromatography on silica gel (2×4 inches) with 50% ethyl acetate/hexane elution gave 0.77 g (37%) of the title product as a light brown oil which slowly solidified. The product was suitable for use in subsequent reactions but was not analytically pure: $^1$H NMR δ 8.36 (s with Sn coupling, 1H), 7.80 (d, J=8 Hz, 1H), 7.61–7.51 (m, 2H), 7.40 (t, J=8 Hz, 1H), 7.09 (dd, J=1, 7.5 Hz, 1H), 3.2 (br s, 4H), 2.75 (br s, 4H), 2.46 (s, 3H), 0.39 (s with Sn coupling of 55.0 and 52.5 Hz, 9H).

PREPARATION 4

8-Bromo-2-(dibenzylamino)-naphthalene

A mixture of dibenzylamine (70.8 mL, 0.368 mol), 8-bromo-2-tetralone (82.86 g, 0.368 mol, U.S. Pat. No. 4,897,405 A), dry toluene (1000 mL), and p-toluenesulfonic acid (0.83 g, 4.36 mmol) was refluxed 2 days with azeotropic removal of water. Most of the toluene was distilled away from the reaction and the residual material was dried in vacuo about 12 hours. The crude enamine was obtained as an orange oil and was used directly in the next step. $^1$H NMR δ 7.41–7.17 (m, 13 H), 6.97 (d, J=7.3 Hz, 1 H), 6.72 (t, J=7.6 Hz, 1 H), 5.83 (s, 1 H), 4.54 (s, 4 H), 2.86 (t, J=7.8 Hz, 2 H), 2.55 (dd, J=8.5, 6.6 Hz, 2 H).

The enamine from the above reaction was dissolved in tetrahydrofuran (2000 mL) and chilled to 0° C. Chloranil (90.48 g, 0.368 mol) was added in portions over 10 minutes. The black solution was stirred 1.45 hours at 0° C., then the solvent was removed at reduced pressure. The residue was taken up in methylene chloride (750 mL) and filtered through celite to remove an insoluble yellow material (discarded). Saturated sodium carbonate (500 mL) was added to the filtrate and the two phase mixture was vigorously stirred 15 minutes. The mixture was again filtered through celite to remove a greenish solid (discarded). The phases were separated from the filtrate and the organic layer was washed with saturated sodium carbonate and then brine. The solution was dried over calcium sulfate and concentrated onto silica gel and applied to a flash chromatography column (4×4 inches silica gel). Elution proceeded as follows: hexane (500 mL, nil); 5% ether/hexane (2 L, nil); 5% ether/hexane (12 L, unweighed orange oil product). The oil was triturated with 50% ether:hexane (500 mL) to yield the tan product, 8-bromo-2-(dibenzylamino)-naphthalene (72.15 g). The residues from the trituration were rechromatographed as above to afford an additional 18.95 g of product. The combined yield was 91.1 g, 61%. mp 102.5°–103° C.; $^1$H NMR δ 7.64–7.60 (m, 3 H), 7.37–7.24 (m, 11 H), 7.13 (dd, J=9, 2.5 Hz, 1 H), 7.00 (t, J=7.8 Hz, 1 H), 4.80 (s, 4 H). Analysis calculated for $C_{24}H_{20}BrN$: C, 71.65; H, 5.01; N, 3.48. Found: C, 71.24; H, 4.65; N, 3.49.

PREPARATION 5

2-Chloro-3-nitropyridine-N-oxide

2-Chloro-3-nitropyridine (0.69 g, 4.35 mmol) was chilled to 0° C. and trifluoroacetic acid (9 mL) was slowly added followed by 30% hydrogen peroxide (1 mL). The solution was warmed to 70° C. for 1.5 hours, cooled to 0° C. and excess peroxide was decomposed by dropwise addition of dimethylsulfide (1 mL) and stirring 0.5 hours. The reaction was concentrated at reduced pressure onto silica gel and flash chromatographed (1×3 inches). Elution proceeded as follows: 50% ethyl acetate/hexane (175 mL), nil; 75% ethyl acetate/hexane (175 mL), 0.589 g (77%) of 2-chloro-3-nitropyridine-N-oxide as an orange solid suitable for use without further purification. A sample recrystallized from ethyl acetate/hexane had mp 98°–100° C. Analysis calculated for $C_5H_3ClN_2O_3$: C, 34.41; H, 1.73; N, 16.05. Found: C, 34.75; H, 1.67; N, 15.80.

PREPARATION 6

5-Trimethylstannylpyrimidine

A mixture of 5-bromopyrimidine (4.00 g, 25.16 mmol), hexamethylditin (9.06 g, 27.67 mmol), lithium chloride (1.27 g, 30.19 mmol), tetrakis(triphenylphosphine) palladium (1.13 g, 0.981 mmol), 2,6-di-tert-butyl-4-methylphenol (approximately 0.01 g), and dioxane (45 mL) was heated at reflux under nitrogen for 7 hours. The resulting mixture was concentrated via evaporation under reduced pressure, and the residue was column chromatographed using silica gel (approximately 200 g) and elution with ethyl acetate/hexanes [1:1] to afford the title compound (4.75 g, 19.6 mmol, 78%) as a clear, colorless liquid: $R_f$=0.6 in ethyl acetate/hexanes[1:1]; $^1$H NMR (CDCl$_3$) δ 9.11 (s, 1H), 8.70 (s, 2H), 0.38 (s, 9H); $^{13}$C NMR (CDCl$_3$) δ 162.8, 158.5, 134.4,°–9.6.

PREPARATION 7

5-Cyano-3-trimethylstannylpyridine

A mixture of 3-bromo-5-cyanopyridine (5.84 g, 31.91 mmol), hexamethylditin (11.49 g, 35.10 mmol), lithium chloride (1.62 g, 38.29 mmol), tetrakis(triphenylphosphine) palladium (1.44 g, 1.24 mmol), 2,6-di-tert-butyl-4-methylphenol (approximately 0.01 g), and dioxane (60 mL) was heated at reflux under nitrogen for 8 hours. The resulting mixture was concentrated via evaporation under reduced pressure, and the residue was column chromatographed using silica gel (approximately 200 g) and elution with ether/hexanes [1:1] to afford the title compound (1.98 g, 7.41 mmol, 23%) as a pale yellow solid: mp, 77.0°–79.0° C.; $R_f$=0.65 in ether/hexanes [1:1]; $^1$H NMR (CDCl$_3$) δ 8.80 (dd, J=1.5 and 2.4 Hz, 2H), 8.03 (dd, J=1.5 and 2.1 Hz, 1H), 0.39 (s, 9H).

The compounds of formula I of the present invention described in the above Examples were assayed for 5-HT$_{1A}$ and 5-HT$_{1D}$ affinity using the aforementioned procedures with IC$_{50}$s of less than 0.60 μM for at least one of the above affinities.

We claim:

1. A pharmaceutical composition for treating or preventing disorders arising from deficient or excessive serotonergic neurotransmission in a mammal, comprising:

a) a pharmaceutically acceptable carrier;

b) a compound of the formula

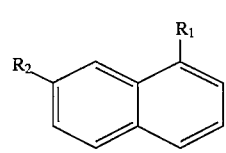

I where $R_1$ is of the formula

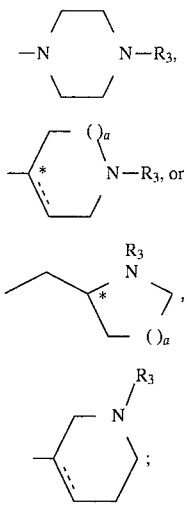

$R_2$ is $-R_4$, $-O-R_4$, $-O-S(O)_2-R_4$, $-NR_4R_5$, $R_4-(CH_2)_b-NH(C=X)-(CH_2)_c-$, $R_4-(CH_2)_b-O(C=O)NH-(CH_2)_c-(C=O)NH-$, $R_4-(C=O)NH-(C=O)NH-$, $-(CH_2)_b-NH(C=X)-(CH_2)_c-R_4$, $R_4-(CH_2)_b-O(C=O)-(CH_2)_c-$, $-(CH_2)_b-O(C=O)-(CH_2)_c-R_4$, $-NH(C=X)NH-R_4$, $R_4-O(C=O)O-$, $-O(C=L)NH-R_4$, $R_4-O(C=O)NH-$, $-(CH_2)_b-(C=O)-(CH_2)_c-R_4$, $-NH-S(O)_2-R_4$, $-C(OH)R_4R_5$, $-CH(OH)-R_4$, $-(C=O)-NR_4R_5$, $-CN$, $-NO_2$, substituted $C_1$ to $C_6$ alkyl, substituted or unsubstituted $C_1$ to $C_6$ alkenyl, or substituted or unsubstituted $C_1$ to $C_6$ alkynyl, said substituted moieties substituted with a moiety of the formulae $-R_4$, $-R_4R_5$, $-O-R_4$, or $-S(O)_d-R_4$;

$R_3$ is hydrogen, $CH_3OCH_2CH_2$, $C_1$ to $C_6$ alkyl, $C_1$ to $C_6$ alkylaryl, or aryl;

$R_4$ and $R_5$ are each, independently,

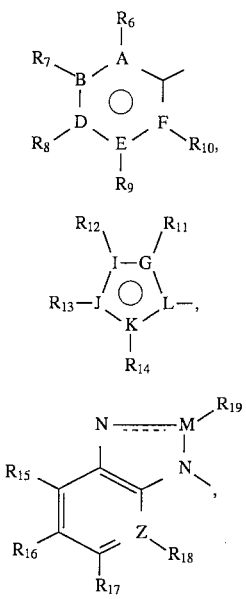

hydrogen, $-CF_3$, $C_1$ to $C_6$ alkyl, or $C_1$ $C_6$ alkylaryl, with the proviso that when $R_2$ is $-R_4$ or $-OR_4$, $R_4$ is not hydrogen or $C_1$ to $C_6$ alkyl;

$R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are each independently H, halogen, $-CF_3$, $-(C=O)R_{20}$, $-CN$, $-OR_{20}$, $-NR_{20}R_{21}$, $-NR_{20}SO_2R_{22}$, $-N_{20}CO_2R_{22}$, $-N=C-N(CH_3)_2$, $-S(O)_eR_{20}$, $-SO_2NR_{20}R_{21}$, $-NO_2$, aryl, $C_1$ to $C_6$ alkylaryl, $-(C=O)OR_{20}$, $-(C=O)NR_{20}R_{21}$, $C_1$ to $C_6$ alkyl, $C_1$ to $C_6$ alkenyl, and $C_1$ to $C_6$ alkynyl;

$R_6$ and $R_7$, $R_7$ and $R_8$, $R_8$ and $R_9$, $R_9$ and $R_{10}$, $R_{11}$ and $R_{12}$, $R_{12}$ and $R_{13}$, $R_{13}$ and $R_{14}$, $R_{16}$ and $R_{16}$, $R_{16}$ and $R_{17}$, and $R_{17}$ and $R_{18}$ may be taken together to form a five-to-seven-membered alkyl ring, a six-membered aryl ring, a five to seven membered heteroalkyl ring having one heteroatom of N, O, or S, or a five-to six-membered heteroaryl ring have 1 to 2 heteroatoms of N, O, or S;

$R_{19}$ is hydrogen or $C_1$ to $C_3$ alkyl;

$R_{20}$ and $R_{21}$ are each independently hydrogen, $C_1$ to $C_6$ alkyl, aryl, or $C_1$ to $C_6$ alkylaryl, or may be taken together to form a $C_4$ to $C_7$ alkyl ring;

$R_{22}$ is $C_1$ to $C_6$ alkyl, aryl, or $C_1$ to $C_6$ alkylaryl;

A, B, D, E, and F are each, independently, C, N, or (C=O);

G, I, J, and K are each, independently, C, N, O, S, or (C=O), with the proviso that there is at most one of O, (C=O), and S per ring;

L and Z are each, independently, C or N;

M is C, N, or (C=O);

X is O or S;

a is 0, 1 or 2;

e is 0, 1 or 2;

d is 0, 1, or 2;

b and c are each, independently, 0, 1, 2, 3, 4, 5, or 6, with b+c being at most 6;

a broken line indicates the presence optionally of a double bond and the above aryl groups and the aryl moieties of the above alkylaryl groups are independently selected from the group consisting of phenyl and substituted phenyl, wherein said substituted phenyl may be substituted with one to three groups selected from the group consisting of $C_1$ to $C_4$ alkyl, halogen, hydroxy, cyano, carboxamido, intro, and $C_1$ to $C_4$ alkoxy;

and the pharmaceutically acceptable salts thereof; and c) a 5-HT re-uptake inhibitor or a pharmaceutically acceptable salt thereof; wherein the active compounds "b" and "c" are present in amounts that render said pharmaceutical composition effective in treating or preventing such condition.

2. A method for treating or preventing disorders arising from deficient or excessive serotonergic neurotransmission in a mammal, comprising administering to said mammal requiring such treatment or prevention:

a) a compound of the formula

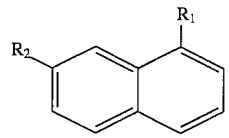

where $R_1$ is of the formulae

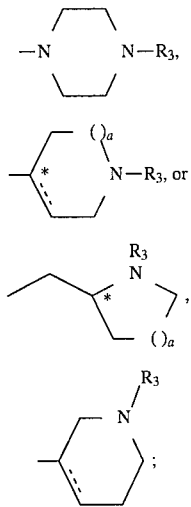

$R_2$ is —$R_4$, —O—$R_4$, —O—S(O)$_2$—$R_4$, —N$R_4R_5$, $R_4$—(CH$_2$)$_b$—NH(C=X)—(CH$_2$)$_c$—, $R_4$—(CH$_2$)$_b$—O(C=O)NH—(CH$_2$)$_c$—(C=O)NH—, $R_4$—(C=O)NH—(C=O)NH—, —(CH$_2$)$_b$—NH(C=X)—(CH$_2$)$_c$—$R_4$, $R_4$—(CH$_2$)$_b$—O(C=O)—(CH$_2$)$_c$—, —(CH$_2$)$_b$—O(C=O)—(CH$_2$)$_c$—$R_4$, —NH(C=X)NH—$R_4$, $R_4$—O(C=O)O—, —O(C=L)NH—$R_4$, $R_4$—O(C=O)NH—, —(CH$_2$)$_b$—(C=O)—(CH$_2$)$_c$—$R_4$, —NH—S(O)$_2$—$R_4$, —C(OH)$R_4R_5$, —CH(OH)—$R_4$, —(C=O)—N$R_4R_5$, —CN, —NO$_2$, substituted $C_1$ to $C_6$ alkyl, substituted or unsubstituted $C_1$ to $C_6$ alkenyl, or substituted or unsubstituted $C_1$ to $C_6$ alkynyl, said substituted moieties substituted with a moiety of the formulae —$R_4$, —$R_4R_5$, —O—$R_4$, or —S(O)$_d$—$R_4$;

$R_3$ is hydrogen, CH$_3$OCH$_2$CH$_2$, $C_1$ to $C_6$ alkylaryl, or aryl;

$R_4$ and $R_5$ are each, independently,

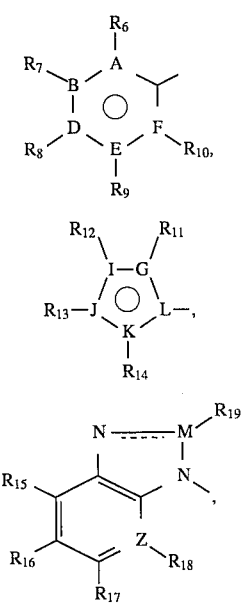

hydrogen, —CF$_3$, $C_1$ to $C_6$ alkyl, or $C_1$ $C_6$ alkylaryl, with the proviso that when $R_2$ is —$R_4$ or —O$R_4$, $R_4$ is not hydrogen or $C_1$ to $C_6$ alkyl;

$R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are each independently H, halogen, —CF$_3$, —(C=O)$R_{20}$, —CN, —O$R_{20}$, —N$R_{20}R_{21}$, —N$R_{20}$SO$_2R_{22}$, —N$_{20}$CO$_2R_{22}$, —N=C—N(CH$_3$)$_2$, —S(O)$_eR_{20}$, —SO$_2$N$R_{20}R_{21}$, —NO$_2$, aryl, $C_1$ to $C_6$ alkylaryl, —(C=O)O$R_{20}$, —(C=O)N$R_{20}R_{21}$, $C_1$ to $C_6$ alkyl, $C_1$ to $C_6$ alkenyl, and $C_1$ to $C_6$ alkynyl;

$R_6$ and $R_7$, $R_7$ and $R_8$, $R_8$ and $R_9$, $R_9$ and $R_{10}$, $R_{11}$ and $R_{12}$, $R_{12}$ and $R_{13}$, $R_{13}$ and $R_{14}$, $R_{16}$ and $R_{16}$, $R_{16}$ and $R_{17}$, and $R_{17}$ and $R_{18}$ may be taken together to form a five-to-seven-membered alkyl ring, a six-membered aryl ring, a five to seven membered heteroalkyl ring having one heteroatom of N, O, or S, or a five-to six-membered heteroaryl ring have 1 to 2 heteroatoms of N, O, or S;

$R_{19}$ is hydrogen or $C_1$ to $C_3$ alkyl;

$R_{20}$ and $R_{21}$ are each independently hydrogen, $C_1$ to $C_6$ alkyl, aryl, or $C_1$ to $C_6$ alkylaryl, or may be taken together to form a $C_4$ to $C_7$ alkyl ring;

$R_{22}$ is $C_1$ to $C_6$ alkyl, aryl, or $C_1$ to $C_6$ alkylaryl;

A, B, D, E, and F are each, independently, C, N, or (C=O);

G, I, J, and K are each, independently, C, N, O, S, or (C=O), with the proviso that there is at most one of O, (C=O), and S per ring;

L and Z are each, independently, C or N;

M is C, N, or (C=O);

X is O or S;

a is 0, 1 or 2;

e is 0, 1 or 2;

d is 0, 1, or 2;

b and c are each, independently, 0, 1, 2, 3, 4, 5, or 6, with b+c being at most 6;

a broken line indicates the presence optionally of a double bond and the above aryl groups and the aryl moieties of the above alkylaryl groups are independently selected from the group consisting of phenyl and substituted phenyl, wherein said substituted phenyl may be substituted with one to three groups selected from the group consisting of $C_1$ to $C_4$ alkyl, halogen, hydroxy, cyano, carboxamido, intro, and $C_1$ to $C_4$ alkoxy, and pharmaceutically acceptable salts thereof; and c) a 5-HT re-uptake inhibitor or a pharmaceutically acceptable salt thereof; wherein the active compounds "a" and "b" are used in amounts that render said method effective in treating or preventing such condition.

3. A pharmaceutical composition for treating or preventing a condition selected from the group consisting of mood disorders, anxiety disorders; agoraphobia, avoidant personality disorder; social phobia, obsessive compulsive disorder; post-traumatic stress disorder; memory disorders; disorders of eating behavior; obesity; cluster headache; migraine; pain; Alzheimer's disease; chronic paroxysmal hemicrania; headache associated with vascular disorders; Parkinson's disease; endocrine disorders; vasospasm; hypertension; disorders in the gastrointestinal tract where changes in motility and secretion are involved; sexual dysfunction; and chemical dependencies in a mammal, comprising:

a) a pharmaceutically acceptable carrier;

b) a compound of the formula

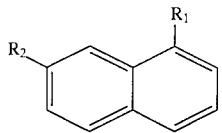   I where $R_1$ is of the formulae

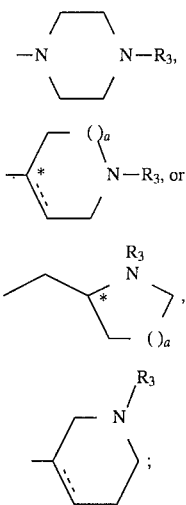

II

III

IV

V $R_2$ is —$R_4$, —O—$R_4$, —O—$S(O)_2$—$R_4$, —$NR_4R_5$, $R_4$—$(CH_2)_b$—NH(C=X)—$(CH_2)_c$—, $R_4$—$(CH_2)_b$—O(C=O)NH—$(CH_2)_c$—(C=O)NH—, $R_4$—(C=O)NH—(C=O)NH—, —$(CH_2)_b$—NH(C=X)—$(CH_2)_c$—$R_4$, $R_4$—$(CH_2)_b$—O(C=O)—$(CH_2)_c$—, —$(CH_2)_b$—O(C=O)—$(CH_2)_c$—$R_4$, —NH(C=X)NH—$R_4$, $R_4$—O(C=O)O—, —O(C=L)NH—$R_4$, $R_4$—O(C=O)NH—, —$(CH_2)_b$—(C=O)—$(CH_2)_c$—$R_4$, —NH—$S(O)_2$—$R_4$, —C(OH)$R_4R_5$, —CH(OH)—$R_4$, —(C=O)—$NR_4R_5$, —CN, —$NO_2$, substituted $C_1$ to $C_6$ alkyl, substituted or unsubstituted $C_1$ to $C_6$ alkenyl, or substituted or unsubstituted $C_1$ to $C_6$ alkynyl, said substituted moieties substituted with a moiety of the formulae —$R_4$, —$R_4R_5$, —O—$R_4$, or —$S(O)_d$—$R_4$;

$R_3$ is hydrogen, $CH_3OCH_2CH_2$, $C_1$ to $C_6$ alkyl, $C_1$ to $C_6$ alkylaryl, or aryl;

$R_4$ and $R_5$ are each, independently,

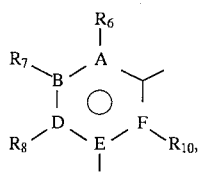   XV

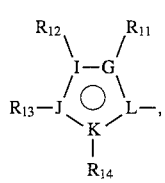   XVI

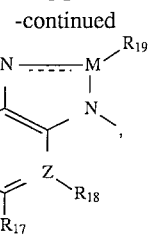   XVII hydrogen, —$CF_3$, $C_1$ to $C_6$ alkyl, or $C_1$ $C_6$ alkylaryl, with the proviso that when $R_2$ is —$R_4$ or —$OR_4$, $R_4$ is not hydrogen or $C_1$ to $C_6$ alkyl;

$R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ are each independently H, halogen, —$CF_3$, —(C=O)$R_{20}$, —CN, —$OR_{20}$, —$NR_{20}R_{21}$, —$NR_{20}SO_2R_{22}$, —$N_{20}CO_2R_{22}$, —N=C—N(CH_3)_2, —$S(O)_eR_{20}$, —$SO_2NR_{20}R_{21}$, —$NO_2$, aryl, $C_1$ to $C_6$ alkylaryl, —(C=O)$OR_{20}$, —(C=O)$NR_{20}R_{21}$, $C_1$ to $C_6$ alkyl, $C_1$ to $C_6$ alkenyl, and $C_1$ to $C_6$ alkynyl;

$R_6$ and $R_7$, $R_7$ and $R_8$, $R_8$ and $R_9$, $R_9$ and $R_{10}$, $R_{11}$ and $R_{12}$, $R_{12}$ and $R_{13}$, $R_{13}$ and $R_{14}$, $R_{16}$ and $R_{16}$, $R_{16}$ and $R_{17}$, and $R_{17}$ and $R_{18}$ may be taken together to form a five-to-seven-membered alkyl ring, a six-membered aryl ring, a five to seven membered heteroalkyl ring having one heteroatom of N, O, or S, or a five-to six-membered heteroaryl ring have 1 to 2 heteroatoms of N, O, or S;

$R_{19}$ is hydrogen or $C_1$ to $C_3$ alkyl;

$R_{20}$ and $R_{21}$ are each independently hydrogen, $C_1$ to $C_6$ alkyl, aryl, or $C_1$ to $C_6$ alkylaryl, or may be taken together to form a $C_4$ to $C_7$ alkyl ring;

$R_{22}$ is $C_1$ to $C_6$ alkyl, aryl, or $C_1$ to $C_6$ alkylaryl;

A, B, D, E, and F are each, independently, C, N, or (C=O);

G, I, J, and K are each, independently, C, N, O, S, or (C=O), with the proviso that there is at most one of O, (C=O), and S per ring;

L and Z are each, independently, C or N;

M is C, N, or (C=O);

X is O or S;

a is 0, 1 or 2;

e is 0, 1 or 2;

d is 0, 1, or 2;

b and c are each, independently, 0, 1, 2, 3, 4, 5, or 6, with b+c being at most 6;

a broken line indicates the presence optionally of a double bond and the above aryl groups and the aryl moieties of the above alkylaryl groups are independently selected from the group consisting of phenyl and substituted phenyl, wherein said substituted phenyl may be substituted with one to three groups selected from the group consisting of $C_1$ to $C_4$ alkyl, halogen, hydroxy, cyano, carboxamido, intro, and $C_1$ to $C_4$ alkoxy, and the pharmaceutically acceptable salts thereof; and c) sertraline or a pharmaceutically acceptable salt or polymorph thereof; wherein the active agents "b" and "c" are present in amounts that render said pharmaceutical composition effective in treating or preventing such condition.

4. A pharmaceutical composition for treating or preventing disorders arising from deficient or excessive serotonergic neurotransmission according to claim 1 wherein said 5-HT re-uptake inhibitor is sertraline or a pharmaceutically acceptable salt or polymorph thereof.

5. A method for treating or preventing a condition selected from the group consisting of mood disorders, anxiety disorders; agoraphobia, avoidant personality disorder; social phobia; obsessive compulsive disorder; post-traumatic stress disorder; memory disorders; disorders of eating behaviour; obesity; cluster headache; migraine; pain; Alzheimer's disease; chronic paroxysmal hemicrania; headache associated with vascular disorders; Parkinson's disease, endocrine disorders; vasospasm; hypertension; disorders in the gastrointestinal tract where changes in motility and secretion are involved; sexual dysfunction; and chemical dependencies in a mammal, comprising administering to said mammal requiring such treatment or prevention;

a) a compound of formula I, as defined in claim 1, or a pharmaceutically acceptable salt thereof; and sertraline or a pharmaceutically acceptable salt or polymorph thereof; wherein the amounts of the active agents "a" and "b" are used in amounts that render said method effective in treating or preventing such condition.

6. A method for treating or preventing disorders arising from deficient or excessive serotonergic neurotransmission according to claim 1 wherein said 5-HT re-uptake inhibitor is sertraline or a pharmaceutically acceptable salt or polymorph thereof.

7. A pharmaceutical composition for treating or preventing a condition selected from the group consisting of mood disorders, anxiety disorders; agoraphobia, avoidant personality disorder; social phobia; obsessive compulsive disorder; post-traumatic stress disorder; memory disorders; disorders of eating behavior; obesity; cluster headache; migraine; pain; Alzheimer's disease; chronic paroxysmal hemicrania; headache associated with vascular disorders; Parkinson's disease; endocrine disorders; vasospasm; hypertension; disorders in the gastrointestinal tract where changes in motility and secretion are involved; sexual dysfunction; and chemical dependencies in a mammal, comprising:

a) a pharmaceutically acceptable carrier;

b) a serotonin 1 ($5\text{-}HT_1$) receptor agonizing or antagonizing effective amount of a compound of formula I, as defined in claim 1, or a pharmaceutically acceptable salt thereof; and a serotonin re-uptake inhibiting effective amount of sertraline or a pharmaceutically acceptable salt or polymorph thereof.

8. A method of treating or preventing a condition selected from the group consisting of mood disorders, anxiety disorders; agoraphobia, avoidant personality disorder; social phobia; obsessive compulsive disorder; post-traumatic stress disorder; memory disorders; disorders of eating behavior; obesity; cluster headache; migraine; pain; Alzheimer's disease; chronic paroxysmal hemicrania; headache associated with vascular disorders; Parkinson's disease; endocrine disorders; vasospasm; hypertension; disorders in the gastrointestinal tract where changes in motility and secretion are involved; sexual dysfunction; and chemical dependencies in a mammal, comprising administering to said mammal;

a) a serotonin 1 ($5\text{-}HT_1$) receptor agonizing or antagonizing effective amount of a compound of formula I, as defined in claim 1, or a pharmaceutically acceptable salt thereof; and a serotonin re-uptake inhibiting effective amount of sertraline or a pharmaceutically acceptable salt or polymorph thereof.

9. A composition according to claim 3, wherein said compound of formula I is a compound wherein $R_1$ is formula II; $R_2$ is $-R_4$, $-OR_4$, $R_4-(CH_2)_b-NH(C=X)-(CH_2)_c-$, or $-(CH_2)_b-NH(C=O)-(CH_2)_c-R_4$; $R_3$ is hydrogen or $C_1$ to $C_6$ alkyl; $R_4$ is formula XV or formula XVII; A, B, D, E, and F are each independently C or N; $R_6$, $R_7$, $R_8$, $R_9$, $R_{10}$, $R_{15}$, $R_{16}$, $R_{17}$, $R_{18}$, and $R_{19}$ are each independently hydrogen, halogen, $-CN$, or $-OR_{20}$; and $R_{20}$ is $C_1$ to $C_6$ alkyl.

10. A composition according to claim 3, wherein said compound of formula I is a compound wherein $R_1$ is formula III; $R_2$ is $R_4$, $-OR_4$, $R_4-(CH_2)_b-NH(C=X)-(CH_2)_c-$, or $-(CH_2)_b-NH(C=O)-(CH_2)_c-R_4$; $R_4$ is formula XV or formula XVII; $R_3$ is hydrogen or $C_1$ to $C_6$ alkyl; A, B, D, E, and F are each independently C or N; $R_6$, $R_7$, $R_8$, $R_9$, $R_{10}$, $R_{15}$, $R_{16}$, $R_{17}$, $R_{18}$, and $R_{19}$ are each independently hydrogen, halogen, $-CN$, or $-OR_{20}$; and $R_{20}$ is $C_1$ to $C_6$ alkyl.

11. A composition according to claim 3, wherein said compound of formula I is a compound wherein $R_1$ is

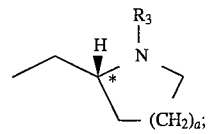

$R_2$ is $-R_4$, $-OR_4$, $R_4-(CH_2)_b-NH(C=X)-(CH_2)_c-$, or $-(CH_2)_b-NH(C=O)-(CH_2)_c-R_4$; $R_3$ is hydrogen or $C_1$ to $C_6$ alkyl; $R_4$ is formula XV or formula XVII; A, B, D, E, and F are each independently C or N; $R_6$, $R_7$, $R_8$, $R_9$, $R_{10}$, $R_{15}$, $R_{16}$, $R_{17}$, $R_{18}$, and $R_{19}$ are each independently hydrogen, halogen, $-CN$, or $-OR_{20}$; and $R_{20}$ is $C_1$ to $C_6$ alkyl.

12. A composition according to claim 3, wherein said compound of formula I is a compound wherein $R_1$ is formula II, formula III, or formula IV; $R_2$ is $-R_4$; $R_3$ is hydrogen or $C_1$ to $C_6$ alkyl; $R_4$ is formula XVII; G, I, J, and K are each independently C, N, or O; L is C; $R_{11}$, $R_{12}$, $R_{13}$, and $R_{14}$ are each independently hydrogen, $C_1$ to $C_6$ alkyl, or $C_1$ to $C_6$ alkylaryl.

13. A composition according to claim 3, wherein said compound of formula I is a compound selected from the group consisting of:

7-(Imidazolo[4,5-b]pyridin-1-yl)-1-(1-methylpyrrolidin-3-yl)naphthalene;

7-(4-Chlorobenzamido)-1-(pyrrolidin-2-(R)-ylmethyl)naphthalene;

2-[3-(4-Methylpiperazin-1-yl)naphthalen-2-yloxy]nicotinonitrile;

1-(4-Methoylpiperazin-1-yl)-7-pyrimidin-5-yl)naphthalene;

7-(5-cyanopyridin-3-yl)-1-(4-methylpiperazin-1-yl)naphthalene;

1-(Piperazin-1-yl)-7-(pyrimidin-5-yl)naphthalene;

7-(4-Chlorobenzamido-1-(4-methylpiperazin-1-yl)naphthalene;

7-(3-Methoxyphenyl)1-(4-methylpiperazin-1-yl)naphthalene;

7-(Imidazolo[4,5-b]pyridin-1-yl)-1-(4-methylpiperazin-1-yl)naphthalene;

8-(4-Methylpiperazin-1-yl)naphthalene-2-carboxylicacid 4-chlorobenzylamide;

7-(4-Methoxyphenyl)-1-(4-methylpiperazin-1-yl)naphthalene;

7-Pyrimidin-2-yloxy-1-(4-methylpiperazin-1-yl)naphthalene;

7-(Benzimidazol-1-yl)-1-(4-methylpiperazin-1-yl)naphthalene; and 8-(1-Methylpiperidin-4-yl)naphthalene-2-carboxylicacid 4-chlorobenzylamide.

* * * * *